US008046171B2

(12) United States Patent
Ecker et al.

(10) Patent No.: US 8,046,171 B2
(45) Date of Patent: Oct. 25, 2011

(54) METHODS AND APPARATUS FOR GENETIC EVALUATION

(75) Inventors: David J. Ecker, Encinitas, CA (US); Richard H. Griffey, Vista, CA (US); Rangarajan Sampath, San Diego, CA (US); Steven A. Hofstadler, Oceanside, CA (US); John McNeil, La Jolla, CA (US); Stanley T. Crooke, Carlsbad, CA (US); Dino J. Sofianos, San Diego, CA (US); Karl H. Rudnick, Solana Beach, CA (US); Duane J. Knize, La Jolla, CA (US); Roland B. Stoughton, San Diego, CA (US); Cecil L. Basham, Jr., Del Mar, CA (US); Clifford T. Lewis, San Diego, CA (US); Brons M. Larson, Santee, CA (US); Jonathan R. Bar-on, San Diego, CA (US); Dennis P. Murray, Culver City, CA (US); David W. Robbins, San Diego, CA (US); John P. Penhune, La Jolla, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 536 days.

(21) Appl. No.: 10/418,514

(22) Filed: Apr. 18, 2003

(65) Prior Publication Data

US 2004/0209260 A1 Oct. 21, 2004

(51) Int. Cl.
*G01N 33/50* (2006.01)
*G01N 24/00* (2006.01)
*B01D 59/44* (2006.01)

(52) U.S. Cl. .................... 702/19; 436/173; 250/281
(58) Field of Classification Search .................. None
See application file for complete search history.

(56) References Cited

U.S. PATENT DOCUMENTS

| | | | |
|---|---|---|---|
| 4,075,475 A | 2/1978 | Risby et al. |
| 4,683,195 A | 7/1987 | Mullis et al. |
| 4,683,202 A | 7/1987 | Mullis et al. |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor et al. |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |

(Continued)

FOREIGN PATENT DOCUMENTS

AU 2003245488 6/2002

(Continued)

OTHER PUBLICATIONS

Keller et al. (Analytical Chemistry (2002) vol. 74, pp. 5383-5392).*
Yao et al. (Analytical Chemistry (2002) vol. 74, pp. 2529-2534).*
Hurst (Rapid Communications in Mass Spectrometry (1996) vol. 10, pp. 377-382).*
Johnson et al. (Journal of Microbiological Methods (2000) vol. 40, pp. 241-254).*
Aaserud, et al., "Accurate base composition of double-stranded DNA by mass spectrometry," J. Am. Soc. Mass Spec. (1996) 7:1266-1269.
Muddiman and Smith, "Sequencing and characterization of larger oligonucleotides by electrospray ionization fourier transform ion cyclotron resonance mass spectrometry," Rev. Anal. Chem. (1998) 17:1-60.

(Continued)

*Primary Examiner* — Lori A Clow
(74) *Attorney, Agent, or Firm* — Casimir Jones S.C.; Christopher C. Sappenfield

(57) ABSTRACT

Rapid and definitive bioagent detection and identification can be carried out without nucleic acid sequencing. Analysis of a variety of bioagents and samples, such as air, fluid, and body samples, can be carried out to provide information useful for industrial, medical, and environmental purposes. Nucleic acid samples of unknown or suspected bioagents may be collected, optimal primer pairs may be selected, and the nucleic acid may be amplified. Expected mass spectra signal models may be generated and selected, the actual mass spectra of the amplicons may be obtained. The expected mass spectra most closely correlating with the actual mass spectra may be determined using a joint maximum likelihood analysis, and base counts for the actual mass spectra and the expected mass spectra may be obtained. The most likely candidate bioagents may then be determined.

16 Claims, 19 Drawing Sheets

U.S. PATENT DOCUMENTS

| | | | |
|---|---|---|---|
| 5,712,125 A | 1/1998 | Uhlen | |
| 5,716,825 A | 2/1998 | Hancock et al. | |
| 5,727,202 A | 3/1998 | Kucala | |
| 5,745,751 A | 4/1998 | Nelson et al. | |
| 5,747,246 A | 5/1998 | Pannetier et al. | |
| 5,747,251 A | 5/1998 | Carson et al. | |
| 5,753,467 A | 5/1998 | Jensen et al. | |
| 5,753,489 A | 5/1998 | Kistner et al. | |
| 5,759,771 A | 6/1998 | Tilanus | |
| 5,763,169 A | 6/1998 | Sandhu et al. | |
| 5,763,588 A | 6/1998 | Matteucci et al. | |
| 5,770,367 A | 6/1998 | Southern et al. | |
| 5,777,324 A | 7/1998 | Hillenkamp | |
| 5,814,442 A | 9/1998 | Natarajan et al. | |
| 5,822,824 A | 10/1998 | Dion | |
| 5,828,062 A | 10/1998 | Jarrell et al. | |
| 5,830,653 A | 11/1998 | Froehler et al. | |
| 5,830,655 A | 11/1998 | Monforte et al. | |
| 5,830,853 A | 11/1998 | Backstrom et al. | |
| 5,832,489 A | 11/1998 | Kucala | |
| 5,834,255 A | 11/1998 | vanGemen et al. | |
| 5,845,174 A | 12/1998 | Yasui et al. | |
| 5,849,492 A | 12/1998 | Rogan | |
| 5,849,497 A | 12/1998 | Steinman | |
| 5,849,901 A | 12/1998 | Mabilat et al. | |
| 5,851,765 A | 12/1998 | Koster | |
| 5,856,174 A | 1/1999 | Lipschutz et al. | |
| 5,864,137 A | 1/1999 | Becker et al. | |
| 5,866,429 A | 2/1999 | Bloch | |
| 5,869,242 A | 2/1999 | Kamb | |
| 5,871,697 A | 2/1999 | Rothberg et al. | |
| 5,872,003 A | 2/1999 | Koster | |
| 5,876,936 A | 3/1999 | Ju | |
| 5,876,938 A | 3/1999 | Stolowitz et al. | |
| 5,885,775 A | 3/1999 | Haff et al. | |
| 5,900,481 A | 5/1999 | Lough et al. | |
| 5,928,905 A | 7/1999 | Stemmer et al. | |
| 5,928,906 A | 7/1999 | Koster | |
| 5,965,363 A | 10/1999 | Monforte et al. | |
| 5,965,383 A | 10/1999 | Vogel et al. | |
| 5,972,693 A | 10/1999 | Rothberg et al. | |
| 5,976,798 A | 11/1999 | Parker et al. | |
| 5,981,176 A | 11/1999 | Wallace | |
| 5,981,190 A | 11/1999 | Israel | |
| 5,994,066 A | 11/1999 | Bergeron et al. | |
| 6,001,564 A | 12/1999 | Bergeron et al. | |
| 6,005,096 A | 12/1999 | Matteucci et al. | |
| 6,007,690 A | 12/1999 | Nelson et al. | |
| 6,007,992 A | 12/1999 | Lin et al. | |
| 6,015,666 A | 1/2000 | Springer et al. | |
| 6,018,713 A | 1/2000 | Coli et al. | |
| 6,024,925 A | 2/2000 | Little et al. | |
| 6,028,183 A | 2/2000 | Lin et al. | |
| 6,043,031 A | 3/2000 | Koster et al. | |
| 6,046,005 A | 4/2000 | Ju | |
| 6,051,378 A | 4/2000 | Monforte et al. | |
| 6,054,278 A | 4/2000 | Dodge et al. | |
| 6,055,487 A | 4/2000 | Margery et al. | |
| 6,060,246 A | 5/2000 | Summerton et al. | |
| 6,061,686 A | 5/2000 | Gauvin et al. | |
| 6,063,031 A | 5/2000 | Cundari et al. | |
| 6,074,823 A | 6/2000 | Koster | |
| 6,074,831 A | 6/2000 | Yakhini et al. | |
| 6,090,558 A | 7/2000 | Butler et al. | |
| 6,104,028 A | 8/2000 | Hunter et al. | |
| 6,110,710 A | 8/2000 | Smith et al. | |
| 6,111,251 A | 8/2000 | Hillenkamp | |
| 6,133,436 A | 10/2000 | Koster et al. | |
| 6,140,053 A | 10/2000 | Koster | |
| 6,146,144 A | 11/2000 | Fowler et al. | |
| 6,146,854 A | 11/2000 | Koster et al. | |
| 6,153,389 A | 11/2000 | Haarer et al. | |
| 6,159,681 A | 12/2000 | Zebala | |
| 6,180,339 B1 | 1/2001 | Sandhu et al. | |
| 6,180,372 B1 | 1/2001 | Franzen | |
| 6,187,842 B1 | 2/2001 | Kobayashi et al. | |
| 6,194,144 B1 | 2/2001 | Koster | |
| 6,197,498 B1 | 3/2001 | Koster | |
| 6,214,555 B1 | 4/2001 | Leushner et al. | |
| 6,218,118 B1 | 4/2001 | Sampson et al. | |
| 6,221,587 B1 | 4/2001 | Ecker et al. | |
| 6,221,598 B1 | 4/2001 | Schumm et al. | |
| 6,221,601 B1 | 4/2001 | Koster et al. | |
| 6,221,605 B1 | 4/2001 | Koster | |
| 6,225,450 B1 | 5/2001 | Koster | |
| 6,235,476 B1 | 5/2001 | Bergmann et al. | |
| 6,235,478 B1 | 5/2001 | Koster | |
| 6,235,480 B1 | 5/2001 | Shultz et al. | |
| 6,238,871 B1 | 5/2001 | Koster | |
| 6,238,927 B1 | 5/2001 | Abrams et al. | |
| 6,239,159 B1 | 5/2001 | Brown et al. | |
| 6,258,538 B1 | 7/2001 | Koster et al. | |
| 6,261,769 B1 | 7/2001 | Everett et al. | |
| 6,265,716 B1 | 7/2001 | Hunter et al. | |
| 6,265,718 B1 | 7/2001 | Park et al. | |
| 6,266,131 B1 | 7/2001 | Hamada et al. | |
| 6,266,144 B1 | 7/2001 | Li | |
| 6,268,129 B1 | 7/2001 | Gut et al. | |
| 6,268,131 B1 | 7/2001 | Kang et al. | |
| 6,268,144 B1 | 7/2001 | Koster | |
| 6,268,146 B1 | 7/2001 | Shultz | |
| 6,270,973 B1 | 8/2001 | Lewis et al. | |
| 6,270,974 B1 | 8/2001 | Shultz et al. | |
| 6,274,726 B1 | 8/2001 | Lugharn, Jr. et al. | |
| 6,277,573 B1 * | 8/2001 | Koster | 435/6 |
| 6,277,578 B1 | 8/2001 | Shultz et al. | |
| 6,277,634 B1 | 8/2001 | McCall et al. | |
| 6,300,076 B1 | 10/2001 | Koster | |
| 6,303,297 B1 | 10/2001 | Lincoln et al. | |
| 6,312,893 B1 | 11/2001 | Van Ness et al. | |
| 6,312,902 B1 | 11/2001 | Shultz et al. | |
| 6,322,970 B1 | 11/2001 | Little et al. | |
| 6,361,940 B1 | 3/2002 | Van Ness et al. | |
| 6,372,424 B1 | 4/2002 | Brow et al. | |
| 6,389,428 B1 | 5/2002 | Rigault et al. | |
| 6,391,551 B1 | 5/2002 | Shultz et al. | |
| 6,393,367 B1 | 5/2002 | Tang et al. | |
| 6,419,932 B1 | 7/2002 | Dale | |
| 6,423,966 B2 | 7/2002 | Hillenkamp et al. | |
| 6,428,955 B1 | 8/2002 | Koster et al. | |
| 6,428,956 B1 | 8/2002 | Crooke et al. | |
| 6,432,651 B1 | 8/2002 | Hughes et al. | |
| 6,436,635 B1 | 8/2002 | Fu et al. | |
| 6,436,640 B1 | 8/2002 | Simmons et al. | |
| 6,453,244 B1 | 9/2002 | Oefner | |
| 6,458,533 B1 | 10/2002 | Felder et al. | |
| 6,468,743 B1 | 10/2002 | Romick et al. | |
| 6,468,748 B1 | 10/2002 | Monforte et al. | |
| 6,475,143 B2 | 11/2002 | Iliff | |
| 6,475,736 B1 | 11/2002 | Stanton, Jr. | |
| 6,475,738 B2 | 11/2002 | Shuber et al. | |
| 6,479,239 B1 | 11/2002 | Anderson et al. | |
| 6,500,621 B2 | 12/2002 | Koster | |
| 6,553,317 B1 | 4/2003 | Lincoln et al. | |
| 6,558,902 B1 | 5/2003 | Hillenkamp | |
| 6,563,025 B1 | 5/2003 | Song et al. | |
| 6,566,055 B1 | 5/2003 | Monforte et al. | |
| 6,568,055 B1 | 5/2003 | Tang et al. | |
| 6,582,916 B1 | 6/2003 | Schmidt et al. | |
| 6,586,584 B2 | 7/2003 | McMillian et al. | |
| 6,589,485 B2 | 7/2003 | Koster | |
| 6,602,662 B1 | 8/2003 | Koster et al. | |
| 6,605,433 B1 | 8/2003 | Fliss et al. | |
| 6,610,492 B1 | 8/2003 | Stanton et al. | |
| 6,613,509 B1 | 9/2003 | Chen | |
| 6,613,520 B2 | 9/2003 | Ashby | |
| 6,623,928 B2 | 9/2003 | Van Ness et al. | |
| 6,638,714 B1 | 10/2003 | Linnen et al. | |
| 6,680,476 B1 | 1/2004 | Hidalgo et al. | |
| 6,682,889 B1 | 1/2004 | Wang et al. | |
| 6,705,530 B2 | 3/2004 | Kiekhaefer | |
| 6,706,530 B2 | 3/2004 | Hillenkamp | |
| 6,716,634 B1 | 4/2004 | Myerson | |
| 6,783,939 B2 | 8/2004 | Olmsted et al. | |
| 6,800,289 B2 | 10/2004 | Nagata et al. | |
| 6,813,615 B1 | 11/2004 | Colasanti et al. | |
| 6,836,742 B2 | 12/2004 | Brekenfeld | |

| | | |
|---|---|---|
| 6,852,487 B1 | 2/2005 | Baraney et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Koster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Koster et al. |
| 7,501,251 B2 | 3/2009 | Koster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Krstyanne et al. |
| 2002/0045178 A1 | 4/2002 | Cantor et al. |
| 2002/0055101 A1 | 5/2002 | Bergereon et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1* | 2/2003 | Ecker et al. ............... 435/6 |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0084483 A1 | 5/2003 | Simpson et al. |
| 2003/0101172 A1 | 5/2003 | Ecker et al. |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0129589 A1 | 7/2003 | Koster et al. |
| 2003/0134312 A1 | 7/2003 | Burgyone et al. |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marmellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1* | 9/2004 | Ecker et al. ............... 435/5 |
| 2004/0185438 A1 | 9/2004 | Ecker et al. |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Michelevich et al. |
| 2005/0130196 A1 | 6/2005 | Hofstadler |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0057605 A1 | 3/2006 | Sampath et al. |
| 2006/0121520 A1 | 6/2006 | Ecker et al. |
| 2006/0172330 A1 | 8/2006 | Osborn et al. |
| 2006/0205040 A1 | 9/2006 | Sampath et al. |
| 2006/0240412 A1 | 10/2006 | Hall et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster et al. |
| 2009/0092977 A1 | 4/2009 | Koster et al. |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| CN | 1202204 | 12/1998 |
| DE | 19732086 | 1/1999 |
| DE | 19802905 | 7/1999 |
| DE | 19824280 | 12/1999 |
| DE | 19852167 | 5/2000 |

| | | | | | | |
|---|---|---|---|---|---|---|
| DE | 19943374 | 3/2001 | | WO | WO 01/07648 | 2/2001 |
| DE | 10132147 | 2/2003 | | WO | WO 01/12853 | 2/2001 |
| EP | 0281390 | 9/1988 | | WO | WO0120018 A2 | 3/2001 |
| EP | 0620862 | 10/1994 | | WO | WO 01/23604 | 4/2001 |
| EP | 0633321 | 11/1995 | | WO | WO 01/23608 | 4/2001 |
| EP | 620862 B1 | 4/1998 | | WO | WO 01/32930 | 5/2001 |
| EP | 1035219 | 9/2000 | | WO | WO 01/40497 | 6/2001 |
| EP | 1138782 | 10/2001 | | WO | WO 01/46404 | 6/2001 |
| EP | 1234888 | 8/2002 | | WO | WO 01/51661 | 7/2001 |
| EP | 1308506 | 5/2003 | | WO | WO 01/51662 | 7/2001 |
| EP | 1310571 | 5/2003 | | WO | WO 01/57263 | 8/2001 |
| EP | 1333101 | 8/2003 | | WO | WO 01/57518 | 8/2001 |
| EP | 1365031 | 11/2003 | | WO | WO 01/73119 | 10/2001 |
| EP | 1748072 | 1/2007 | | WO | WO 01/73199 | 10/2001 |
| FR | 2811321 | 1/2002 | | WO | WO 01/77392 | 10/2001 |
| GB | 2325002 | 11/1998 | | WO | WO0196388 A2 | 12/2001 |
| GB | 2339905 | 2/2000 | | WO | WO 02/02811 | 1/2002 |
| JP | 5-276999 | 10/1993 | | WO | WO 02/10186 | 2/2002 |
| JP | 11137259 A | 5/1999 | | WO | WO 02/10444 | 2/2002 |
| JP | 2004-200 | 1/2004 | | WO | WO 02/18641 | 3/2002 |
| JP | 2004-24206 | 1/2004 | | WO | WO 02/21108 | 3/2002 |
| JP | 2004-201641 | 7/2004 | | WO | WO 02/22873 | 3/2002 |
| JP | 2004-201679 | 7/2004 | | WO | WO 02/24876 | 3/2002 |
| WO | WO 88/03957 | 6/1988 | | WO | WO 02/50307 | 6/2002 |
| WO | WO 90/15157 | 12/1990 | | WO | WO 02/057491 | 7/2002 |
| WO | WO 92/08117 | 5/1992 | | WO | WO 02/070664 | 9/2002 |
| WO | WO 92/09703 | 6/1992 | | WO | WO 02/070728 | 9/2002 |
| WO | WO 92/05182 | 11/1992 | | WO | WO02070737 A2 | 9/2002 |
| WO | WO 92/19774 | 11/1992 | | WO | WO 02/077278 | 10/2002 |
| WO | WO 93/03186 | 2/1993 | | WO | WO 02/099034 | 12/2002 |
| WO | WO9305182 A1 | 3/1993 | | WO | WO 02/099095 | 12/2002 |
| WO | WO 93/08297 | 4/1993 | | WO | WO 02/099129 | 12/2002 |
| WO | WO 94/16101 | 7/1994 | | WO | WO 02/099130 | 12/2002 |
| WO | WO 94/19490 | 9/1994 | | WO | WO 03/002750 | 1/2003 |
| WO | WO 94/21822 | 9/1994 | | WO | WO 03/008636 | 1/2003 |
| WO | WO 95/04161 | 2/1995 | | WO | WO03001976 A2 | 1/2003 |
| WO | WO 95/11996 | 5/1995 | | WO | WO 03/012058 | 2/2003 |
| WO | WO 95/13395 | 5/1995 | | WO | WO 03/012074 | 2/2003 |
| WO | WO 95/13396 | 5/1995 | | WO | WO 03/014382 | 2/2003 |
| WO | WO 95/31997 | 11/1995 | | WO | WO 03/016546 | 2/2003 |
| WO | WO9606187 A1 | 2/1996 | | WO | WO 03/020890 | 3/2003 |
| WO | WO 96/16186 | 5/1996 | | WO | WO03018636 A2 | 3/2003 |
| WO | WO 96/29431 | 9/1996 | | WO | WO 03/033732 | 4/2003 |
| WO | WO 96/32504 | 10/1996 | | WO | WO 03/054162 | 7/2003 |
| WO | WO 96/35450 | 11/1996 | | WO | WO 03/054755 | 7/2003 |
| WO | WO 96/37630 | 11/1996 | | WO | WO 03/060163 | 7/2003 |
| WO | WO97/33000 | 9/1997 | | WO | WO 03/075955 | 9/2003 |
| WO | WO 97/34909 | 9/1997 | | WO | WO 03/088979 | 10/2003 |
| WO | WO97/37041 | 10/1997 | | WO | WO 03/093506 | 11/2003 |
| WO | WO 97/47766 | 12/1997 | | WO | WO 03/097869 | 11/2003 |
| WO | WO 98/03684 | 1/1998 | | WO | WO 03/100035 | 12/2003 |
| WO | WO98/12355 | 3/1998 | | WO | WO 03/100068 | 12/2003 |
| WO | WO 98/14616 | 4/1998 | | WO | WO 03/102191 | 12/2003 |
| WO | WO 98/15652 | 4/1998 | | WO | WO 03/104410 | 12/2003 |
| WO | WO 98/20020 | 5/1998 | | WO | WO03106635 A2 | 12/2003 |
| WO | WO 98/20157 | 5/1998 | | WO | WO 2004/003511 | 1/2004 |
| WO | WO98/20166 | 5/1998 | | WO | WO2004009849 A1 | 1/2004 |
| WO | WO 98/26095 | 6/1998 | | WO | WO 2004/011651 | 2/2004 |
| WO | WO 98/31830 | 7/1998 | | WO | WO 2004/013357 | 2/2004 |
| WO | WO 98/35057 | 8/1998 | | WO | WO 2004/040013 | 5/2004 |
| WO | WO 98/40520 | 9/1998 | | WO | WO 2004/044123 | 5/2004 |
| WO | WO 98/54751 | 12/1998 | | WO | WO 2004/044247 | 5/2004 |
| WO | WO9854571 A1 | 12/1998 | | WO | WO 2004/052175 | 6/2004 |
| WO | WO 99/05319 | 2/1999 | | WO | WO 2004/053076 | 6/2004 |
| WO | WO 99/12040 | 3/1999 | | WO | WO 2004/053141 | 6/2004 |
| WO | WO 99/13104 | 3/1999 | | WO | WO 2004/053164 | 6/2004 |
| WO | WO99/14375 | 3/1999 | | WO | WO 2004/060278 | 7/2004 |
| WO | WO 99/29898 | 6/1999 | | WO | WO 2004/070001 | 8/2004 |
| WO | WO99/31278 | 6/1999 | | WO | WO 2004/072230 | 8/2004 |
| WO | WO 00/63362 | 10/1999 | | WO | WO 2004/072231 | 8/2004 |
| WO | WO 99/57318 | 11/1999 | | WO | WO 2004/101809 | 11/2004 |
| WO | WO 99/58713 | 11/1999 | | WO | WO 2005/003384 | 1/2005 |
| WO | WO 99/60183 | 11/1999 | | WO | WO 2005/012572 | 2/2005 |
| WO | WO0032750 A1 | 6/2000 | | WO | WO2005009202 A2 | 2/2005 |
| WO | WO0038636 A1 | 7/2000 | | WO | WO 2005/024046 | 3/2005 |
| WO | WO 00/66789 | 11/2000 | | WO | WO2005036369 A2 | 4/2005 |
| WO | WO0066762 A2 | 11/2000 | | WO | WO 2005/053141 | 6/2005 |
| WO | WO0077260 A1 | 12/2000 | | WO | WO 2005/054454 | 6/2005 |
| WO | WO0100828 A2 | 1/2001 | | WO | WO2005086634 A2 | 9/2005 |

| WO | WO 2005/075686 | 10/2005 |
| WO | WO 2005/091971 | 10/2005 |
| WO | WO 2005/098047 | 10/2005 |
| WO | WO2005116263 A2 | 12/2005 |
| WO | WO 2006/089762 | 8/2006 |
| WO | WO 2006/094238 | 9/2006 |
| WO | WO 2006/116127 | 11/2006 |
| WO | WO2006135400 A2 | 12/2006 |
| WO | WO2007014045 A2 | 2/2007 |
| WO | WO 2007/086904 | 8/2007 |
| WO | WO2008104002 A2 | 8/2008 |
| WO | WO 2008/118809 | 10/2008 |

OTHER PUBLICATIONS

Hurst. et al., "Detection of bacterial DNA polymerase chain reaction products by matrix-assisted laser desorption/ionization mass spectrometry," Rapid Comm Mass Spec. (1996) 10;377-382.

Wunschel, et al., "Heterogeneity in *Bacillus cereus* PCR products detected by ESI-FTICR mass spectrometry," Anal. Chem. (1998) 70:1203-1207.

Muddiman, et al., "Precise mass measurement of double-stranded 500 base pair (309 kDa) polymerase chain reaction product by negative ion electrospray ionization fourier transform ion cyclotron resonance mass spectroscopy." Rapid Comm. Mass Spec. (1999) 13:1201-1204.

Muddiman, et al., "Length and base composition of PCR-amplified nucleic acids using mass measurements from electrospray ionization mass spectrometry," Anal. Chem. (1997) 69:1543-1549.

Aaserud et al., "DNA sequencing with balckbody infrared radioactive dissociation of electrosprayed ions" Int. J. Mass. Spectrom. Ion Processes, (1997) 167-168: 705-712.

Adam et al., Molecular structure of the two-dimensional hexon crystalline array and of adenovirus capsid: *Acta Microbiol. Immuno. Hung.* (1998) 45:305-310.

Adam et al., "Intertype specific epitope structure of adenovirus hexon" *Acta Microbiol. Immuno. Hung.* (1998) 45:311-316.

Adam et al., "Characterization of intertype specific epitopes on adenovirus hexons" *Arch. Virol.* (1998) 143:1669-1682.

Adrian et al., "DNA restriction analysis of adenovirus prototypes 1 to 41" *Arch. Virol.* (1986) 91:277-290.

Adzhar et al., "Universal oligonucleotides for the detection of infectious bronchitis virus by the polymerase chain reaction" Avian Pathology (1996) 25:817-836.

Agostini et al. "Complete genome of a JC virus genotype Type 6 from the brain of an African American with progressive multifocal leukoencephalopathy" (1998) 1:267-272.

Akalu et al., "Rapid identification of subgenera of human adenovirus by serological and PCR assays" *J. Virol Methods* (1998) 71:187-196.

Allaouchiche et al., "Clinical Impact of Rapid Oxacillin Susceptibility Testing Using a PCR Assay in *Staphylococcus aureus* Bactaeremia" J. Infect. (1999) 39(3):198-204.

Allawi, H.T. & Santa Lucia J., Jr. Thermodynamics and NMR of internal G.T. mismatches in DNA, Biochemistry, 36, 10581-94 (1997).

Altschul et al., J. Mol. Biol., 215, 403-410 (1990).

Altschul et al., Nucl. Acid Res., 25:3389-3402 (1997).

Alves-Silva, J. et al., "The Ancestry of Brazilian mtDNA Lineages," *Am. J. Hum. Genet.* (2000) 67:444-461.

Amano et al., "Detection of influenza virus: traditional approaches and development of biosensors" Anal. Bioanal. Chem. (2005) 381:156-164.

Amexis et al., "Quantititative mutant analysis of viral quasispecies by chip-based matrix-assisted laser desorption/ionization of time-of-flight mass spectrometry" PNAS (2001) 98(21):12097-12102; Correction: 98(24):14186.

Anderson et al., "Sequence and organization of the human mitochondrial genome," *Nature* (1981) 290:457-465.

Anderson and Young, Quantitative Filter Hybridization in Nucleic Acid Hybridization (1985).

Andreasson et al., "Mitochondrial Sequence Analysis for Forensic Identification Using Pyrosequencing Technology" *BioTechniques* (2002) 32:124-133.

Anthony et al., "Use of the Polymerase Chain Reaction for Rapid Detection of High-Level Mupirocin Resistance in *Staphylococci*" Eur. J. Clin. Microbiol. Infect. Dis. (1999) 18(1):30-34.

Application for Grant by David Mitchell Lubmann dated Oct. 25, 1992 and Oct. 29, 1992.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Continuation Grant by David Mitchell Lubmann dated Jun. 4, 1996 and Jun. 14, 1996.

U.S. Appl. No. 09/798,007 Office Communication Mailed Apr. 16, 2002.

U.S. Appl. No. 09/798,007 Office Communication Mailed Jun. 20, 2002.

U.S. Appl. No. 09/798,007 Office Communication Mailed Nov. 6, 2002.

U.S. Appl. No. 09/798,007 Office Communication Mailed Jan. 8, 2003.

U.S. Appl. No. 09/798,007 Office Communication Mailed Jan. 31, 2003.

U.S. Appl. No. 09/798,007 Office Communication Mailed Feb. 27, 2003.

U.S. Appl. No. 09/798,007 Office Communication Mailed May 20, 2003.

U.S. Appl. No. 09/798,007 Office Communication Mailed May 28, 2003.

U.S. Appl. No. 09/798,007 Office Communication Mailed Jul. 11, 2003.

U.S. Appl. No. 09/798,007 Office Communication Mailed Sep. 22, 2003.

U.S. Appl. No. 09/798,007 Office Communication Mailed Nov. 9, 2003.

U.S. Appl. No. 09/798,007 Office Communication Mailed Jun. 30, 2004.

U.S. Appl. No. 09/798,007 Office Communication Mailed Aug. 10, 2004.

U.S. Appl. No. 09/798,007 Office Communication Mailed Feb. 10, 2005.

U.S. Appl. No. 09/891,793 Office Communication Mailed Dec. 18, 2002.

U.S. Appl. No. 09/891,793 Office Communication Mailed May 19, 2003 interview summary report.

U.S. Appl. No. 09/891,793 Office Communication Mailed May 23, 2003.

U.S. Appl. No. 09/891,793 Office Communication Mailed Aug. 26, 2003.

U.S. Appl. No. 09/891,793 Office Communication Mailed Nov. 13, 2003.

U.S. Appl. No. 09/891,793 Office Communication Mailed Mar. 9, 2004.

U.S. Appl. No. 09/891,793 Office Communication Mailed Jun. 14, 2004.

U.S. Appl. No: 09/891,793 Office Communication Mailed Jul. 13, 2004.

U.S. Appl. No. 09/891,793 Office Communication Mailed Aug. 10, 2004.

U.S. Appl. No. 09/891,793 Office Communication Mailed Oct. 20, 2004.

U.S. Appl. No. 09/891,793 Office Communication Mailed Mar. 8, 2005.

U.S. Appl. No. 09/891,793 Office Communication Mailed May 19, 2005.

U.S. Appl. No. 09/891,793 Office Communication Mailed Aug. 11, 2005.

U.S. Appl. No. 09/891,793 Office Communication Mailed Mar. 16, 2006.

U.S. Appl. No. 09/891,793 Office Communication Mailed Jul. 12, 2006.

U.S. Appl. No. 09/891,793 Office Communication Mailed Sep. 13, 2006.

U.S. Appl. No. 09/891,793 Office Communication Mailed Nov. 20, 2006.

U.S. Appl. No. 09/891,793 Office Communication Mailed Jul. 22, 2008.
U.S. Appl. No. 10/156,608 Office Communication Mailed Apr. 1, 2004.
U.S. Appl. No. 10/156,608 Office Communication Mailed Aug. 10, 2004.
U.S. Appl. No. 10/156,608 Office Communication Mailed Oct. 14, 2004.
U.S. Appl. No. 10/156,608 Office Communication Mailed Nov. 19, 2004.
U.S. Appl. No. 10/156,608 Office Communication Mailed Dec. 9, 2004.
U.S. Appl. No. 10/156,608 Office Communication Mailed May 23, 2005.
U.S. Appl. No. 10/156,608 Office Communication Mailed May 26, 2005.
U.S. Appl. No. 10/156,608 Office Communication Mailed Jul. 20, 2005.
U.S. Appl. No. 10/156,608 Office Communication Mailed Sep. 15, 2005.
U.S. Appl. No. 10/156,608 Office Communication Mailed Jun. 2, 2006.
U.S. Appl. No. 10/323,438 Office Communication Mailed Nov. 20, 2003.
U.S. Appl. No. 10/323,438 Office Communication Mailed Jul. 26, 2004.
U.S. Appl. No. 10/325,527 Office Communication Mailed Dec. 3, 2003.
U.S. Appl. No. 10/325,527 Office Communication Mailed Aug. 16, 2004.
U.S. Appl. No. 10/325,527 Office Communication Mailed Mar. 11, 2005.
U.S. Appl. No. 10/326,642 Office Communication Mailed Nov. 21, 2003.
U.S. Appl. No. 10/326,642 Office Communication Mailed Jul. 14, 2004.
U.S. Appl. No. 10/660,122 Office Communication Mailed Mar. 17, 2006.
U.S. Appl. No. 10/660,122 Office Communication Mailed Jul. 6, 2006.
U.S. Appl. No. 10/660,122 Office Communication Mailed Sep. 19, 2006.
U.S. Appl. No. 10/660,122 Office Communication Mailed Apr. 20, 2007.
U.S. Appl. No. 10/660,122 Office Communication Mailed Sep. 19, 2007.
U.S. Appl. No. 10/660,122 Office Communication Mailed Mar. 21, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,996 Office Communication Mailed Feb. 28, 2006.
U.S. Appl. No. 10/660,996 Office Communication Mailed May 30, 2006.
U.S. Appl. No. 10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,996 Office Communication Mailed Jul. 10, 2007 with associated Information Disclosure Statement filed Feb. 21, 2007.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,997 Office Communication Mailed Apr. 26, 2007 with associated Information Disclosure Statement filed Feb. 20, 2007.
U.S. Appl. No. 10/660,998 Office Communication Mailed May 1, 2006.
U.S. Appl. No. 10/660,998 Office Communication Mailed Aug. 3, 2006.
U.S. Appl. No. 10/660,998 Office Communication Mailed Jan. 24, 2007.
U.S. Appl. No. 10/660,998 Office Communication Mailed Aug. 7, 2007.
U.S. Appl. No. 10/660,998 Office Communication Mailed Dec. 11, 2007.
U.S. Appl. No. 10/660,998 Office Communication Mailed Sep. 19, 2008.
U.S. Appl. No. 10/660,998 Office Communication Mailed Apr. 7, 2009.
U.S. Appl. No. 10/728,486 Office Communication Mailed Apr. 10, 2006.
U.S. Appl. No. 10/728,486 Office Communication Mailed Jul. 27, 2006.
U.S. Appl. No. 10/728,486 Office Communication Mailed Oct. 17, 2007.
U.S. Appl. No. 10/728,486 Office Communication Mailed Dec. 20, 2006.
U.S. Appl. No. 10/728,486 Office Communication Mailed May 11, 2007.
U.S. Appl. No. 10/728,486 Office Communication Mailed Jan. 23, 2008.
U.S. Appl. No. 10/728,486 Office Communication Mailed Nov. 3, 2008.
U.S. Appl. No. 10/754,415 Office Communication Mailed Mar. 13, 2006.
U.S. Appl. No. 10/754,415 Office Communication Mailed Aug. 28, 2006.
U.S. Appl. No. 10/754,415 Office Communication Mailed Nov. 17, 2006.
U.S. Appl. No. 10/754,415 Office Communication Mailed Feb. 27, 2007.
U.S. Appl. No. 10/754,415 Office Communication Mailed Aug. 30, 2007.
U.S. Appl. No. 10/754,415 Office Communication Mailed Oct. 10, 2007.
U.S. Appl. No. 10/754,415 Office Communication Mailed Jun. 12, 2008.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/933,928 Office Communication Mailed Jun. 2, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.
U.S. Appl. No. 10/943,344 Office Communication Mailed Oct. 14, 2009.

U.S. Appl. No. 11/059,776 Office Communication Mailed Jan. 19, 2007.
U.S. Appl. No. 11/059,776 Office Communication Mailed May 29, 2007.
U.S. Appl. No. 11/059,776 Office Communication Mailed Jan. 23, 2008.
U.S. Appl. No. 11/060,135 Office Communication Mailed Dec. 21, 2006.
U.S. Appl. No. 11/060,135 Office Communication Mailed Mar. 8, 2007.
U.S. Appl. No. 11/060,135 Office Communication Mailed Jul. 24, 2007.
U.S. Appl. No. 11/060,135 Office Communication Mailed Mar. 25, 2008.
U.S. Appl. No. 11/060,135 Office Communication Mailed Jan. 2, 2009.
U.S. Appl. No: 11/060,135 Office Communication Mailed Jul. 15, 2009.
U.S. Appl. No. 11/070,634 Office Communication Mailed Jul. 23, 2009.
U.S. Appl. No. 11/136,134 Office Communication Mailed Jun. 20, 2007.
U.S. Appl. No. 11/136,134 Office Communication Mailed Mar. 26, 2008.
U.S. Appl. No. 11/136,134 Office Communication Mailed Oct. 31, 2008.
U.S. Appl. No. 11/136,134 Office Communication Mailed Feb. 12, 2009.
U.S. Appl. No. 11/136,134 Office Communication Mailed May 21, 2009.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No. 11/331,978 Office Communication Mailed Nov. 15, 2007.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,978 Office Communication Mailed Jun. 2, 2008 ( interview summary).
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Jul. 9, 2008.
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Oct. 31, 2007.
U.S. Appl. No. 11/409,535 Office Communication Mailed Apr. 16, 2008.
U.S. Appl. No. 11/491,376 Office Communication Mailed Oct. 31, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct. 24, 2008.
U.S. Appl. No. 11/582,930 Office Communication Mailed Jan. 16, 2009.
U.S. Appl. No. 11/582,930 Office Communication Mailed Jul. 2, 2009.
U.S. Appl. No. 11/685,598 Office Communication Mailed Aug. 18, 2009.
U.S. Appl. No. 11/754,163 Office Communication Mailed Jul. 28, 2009.
U.S. Appl. No. 11/754,169 Office Communication Mailed Aug. 25, 2009.
U.S. Appl. No. 11/754,174 Office Communication Mailed Aug. 3, 2009.
U.S. Appl. No. 11/754,182 Office Communication Mailed Jul. 2, 2009.
U.S. Appl. No. 12/211,641 Office Communication Mailed Apr. 17, 2009.
U.S. Appl. No. 12/326,800 Office Communication Mailed Oct. 21, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
U.S. Appl. No. 90/010,447 Office Communication Mailed Apr. 24, 2009.
U.S. Appl. No. 90/010,447 Office Communication Mailed Mar. 12, 2009.
U.S. Appl. No. 90/010,448 Office Communication Mailed Apr. 24, 2009.
U.S. Appl. No. 90/010,448 Office Communication Mailed Mar. 12, 2009.
Arbique et al., "Comparison of the Velogene Rapid MRSA Identification Assay, Denka MRSA-Screen Assay, and BBL Crystal MRSA ID System for rapid identification of methicillin-resistant *Staphylococcus aureus*" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother.* (1990) 34(9): 1720-1724.
Armstrong, P. et al., "Sensitive and Specific Colorimetric Dot Assay to Detect Eastern Equine Encephalomyelitis Viral RNA in Mosquitoes After PCR Amplification" J. Med, Entomol. (1995) 32(1):42-52.
Arnal et al., "Quantification of Hepatitis A virus in shellfish by competitive reverse transcription PCR with coextraction of standard RNA" Applied and Environmental Microbiology, American Society for Microbiology (1999) 65(1):322-326.
Aronsson et al., Persistence of the influenza A/WSN/33 virus RNA at midbrain levels of immunodefective mice, Online Publication Date: Apr. 1, 2001, Journal of the NeuroVirology 7:117-124, 2001.
Avellon et al. "Rapid and sensitive diagnosis of human adenovirus infections by a generic polymerase chain reaction" *J. Virol. Methods* (2001) 92:113-120.
Azevedo et al. "Detection of influenza, parainfluenza, adenovirus and respiratory syncytial virus during asthma attacks in children older than two years old." Allergol. Immunopathol. (2003) 31:311-317.
Baba et al., "Genome and virulence determinants of high virulence community-acquired MRSA" Lancet (2002) 359:1819-1827.

Bahrmand et al., "Polymerase chain reaction of bacterial genomes with single universal primer: application to distinguishing mycobacteria species" Molecular and Cellular Probes (1996) 10:117-122.

Bahrmand et al., "Use of restriction enzyme analysis of amplified DNA coding for the hsp65 gene and polymerase chain reaction with universal primer for rapid differentiation of mycobacterium species in the clinical laboratory" Scandinavian Journal of Infectious Diseases (1998) 30:477-480.

Bai, J, T.H. Liu and D.M.. Lubman, "Matrix-Assisted Laser Desorption/Ionization Mass Spectrometry of Restriction Enzyme-Digested Plasmid DNA Using an Active Nafion Substrate," 8 Rapid Commun. Mass Spectrom. 687-691 (1994) ( 787 reexamination).

Baker et al., "Review and re-analysis of domain-specific 16S primers" J. Microbiol. Methods (2003) 55:541-555.

Banik et al. "Multiplex PCR assay for rapid identification of oculopathogenic adenoviruses by amplification of the fiber and hexon genes" J. Clin. Microbiol (2005) 43:1064-1068.

Barbour et al. "Identification of an uncultivatable Borrelia species in the hard tick Amblyomma americanum: Possible agent of a Lyme disease-like illness" The Journal of Infectious Diseases (1996) 173:403-409.

Barns et al., "Detection of diverse new Francisella-like bacteria in environmental samples." Applied and Environmental Microbiology (2005) 71:5494-5500.

Baron, E. J., "Genetic Aspects of Methicillin Resistance in Staphylococcus aureus and Methods Used for its Detection in Clinical Laboratories in the United States," J. Chemother. (1995) 7(Suppl. 3): 87-92.

Barr et al., "An Influenza A(H3) Reassortant Was Epidemic in Australia and New Zealand in 2003" J. Med. Virol. (2005) 76:391-397.

Barski, P. et al., "Rapid assay for detection of methicillin-resistant Staphylococcus aureus using multiplex PCR," Mol. Cell Probes (1996) 10:471-475.

Bastia et al., "Organelle DNA analysis of Solanum and Brassica somatic hybrids by PCR with 'universal primers'." Theoretical and Applied Genetics (2001) 102:1265-1272.

Batey et al., "Preparation of Isotopically Labeled Ribonucleotides for Multidimensional NMR Spectroscopy of RNA" Nucleic Acids Research (1992) 20:4515-4523.

Baumer et al., "Age-related Human mtDNA Deletions: A Heterogeneous Set of Deletions Arising at a Single Pair of Directly Repeated Sequences" Am. J. Hum. Genet. (1994) 54:618-630.

Beall, B., et al. "Survey of emm Gene Sequences and T-Antigen Types from Systemic Streptococcus pyogenes Infection Isolates Collected in San Francisco, California; Atlanta, Georgia; and Connecticut in 1994 and 1995" (1997), J. Clin. Micro. 35, 1231-1235.

Beall et al., "Sequencing emm-Specific PCR Products for Routine and Accurate Typing of Group A Streptococci" (1996) J. Clin. Micro. 34, 953-958.

Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.

Benson et al., "Advantages of Thermococcus kodakaraenis (KOD) DNA polymerase for PCR-mass spectrometry based analyses" J. Am. Soc. Mass Spectrom. (2003) 14:601-604.

Berencsi, G. et al., "Molecular Biological Characterization of Adenovirus DNA", Acta Microbiol. Immunol. Hung, 1998, vol. 45, Nos. 3-4; pp. 297-304.

Bisno, A.L. (1995) "Streptococcus pyogenes," Infectious Diseases and Their Etiologic Agents in "Principles and Practice of Infectious Diseases", eds., Mandell, G.L., Bennett, J.E. & Dolin, R. (Churchill Livingston, New York), vol. 2, pp. 1786-1799.

Black et al., "Detection of trace levels of tricothecene mycotoxins in human urine by gas chromatography-mass spectrometry" J. Chromatog (1986) 367:103-115.

Blaiotta, G. et al., "PCR detection of Staphylococcal enterotoxin genes in Staphyiococcus spp. strains isolated from meat and dairy products. Evidence for new variants of seG and sel in S. aureus Ab-8802," J. Appl. Microbiol. (2004) 97:719-730.

Blast Search results (Mar. 2006).

Boivin-Jahns et al., "Bacterial Diversity in a Deep-Subsurface Clay Environment" Applied and Environmental Microbiology (1996) 62:3405-3412.

Bolton and McCarthy, Proc. Natl. Acad. Sci. U.S.A., 48, 1390 (1962).

Bont, Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chemistry, 49(4):552-561 Apr. 2003.

Borrow et al., "SiaD PCR Elisa for confirmation and identification of serogroup Y and W135 meningococcal infections" FEMS Microbiological Letters (1998) 159:209-214.

Boubaker, K. et al., "Panton-Valentine Leukocidin and Staphylococcal Skin Infections in Schoolchildren," Emerg.Infct. Dis. (2004) 10(1):121-124.

Bowen et al., "The native virulence plasmid combination affects the segregational stability of a theta-replicating shuttle vector in Bacillus anthracis var, New Hampshire" J. Appl. Microbiol. (1999) 87:270-278.

Bowers, K. M. et al., "Screening for methicillin resistance in Staphylococars aureus and coagulase-negative staphylococci: evaluation of three selective and Mastalex-MRSA latex agglutination," Br. J. Biomed. Sci. (2003) 60(2):71-74.

Brakstad, O. G, et al., "Multiplex polylnerase chain reaction for detection of genes for Staphylococcus aureus themonuclease and methicillin resistance and correlation with oxacillin resistance," APMIS (1993) 101 :681-688.

Brakstad, O. G. et al., "Direct identification of Staphylococcus aureus in blood cultures by detection of the gene, encoding the thermostable nuclease or the gene product," APMIS (1995) 103:209-218.

Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.

Brayshaw, D. P., "Methicillin-resistant Staphylococcus aureus: evaluation of detection techniques with laboratory-passaged organisms," Br. J Biorned. Sci. (1999) 56:170-176.

Brightwell et al., "Development of internal controls for PCR detection of Bacillus anthracis" Molecular and Cellular Probes (1998) 12(6):367-377.

Brightwell , G. et a., "Genetic targets for the detection and identifiaction of Venezuelan equine encephalitis viruses," Arch. Virol (1998) 143(4): 731-742.

Bronzoni, R. V. M. et al., "Multiplex nested PCR for Brazilian Alphavirus diagnosis," Trans. R. Soc. Trop. Med. Hyg. (2004) 98(8): 456-461.

Bronzoni, R. V. M. et al., "Duplex Reverse Transcription-PCR Followed by Nested PCR Assats for Detection and Identification of Brazilan Alphaviruses and Flaviviruses." J. Clin. Microbiol. (2005) 43(2): 696-702.

Brown, "Advances in Molecular Diagnostics for Avian Influenza" Dev. Biol. (2006) 124:93-97.

Brownstein et al., "Modulation of Non-Templated Nucleotide Addition by Taq DNA Polymerase: Primer Modifications that Facilitate Genotyping" BioTechniques (1996) 20:1004-1010.

Brunaud et al., "T-DNA integration into the Arabidopsis genome depends on sequences of pre-insertion sites" EMBO Rep. (2002) 3(12):1152-1157.

Buck et al., "Design Strategies and Performance of Custom DNA Sequencing Primers" Biotechniques (1999) 27:528-536.

Butel et al. "Cell and molecular biology of simian virus 40: implications for human infections and diseases" J. Natl. Cancer Institute (1999) 91(2):119-134.

Campbell et al., "Detection of California serogroup Bunyaviruses in tissue culture and mosquito pools by PCR" J. Virol. Methods (1996) 57:175-179.

Carracedo et al., "DNA commission of the international society for forensic genetics: guidelines for mitochondrial DNA typing" Forensic Science International (2000) 110:79-85.

Carroll, K. C. et al., "Rapid Detection of the Staphylococcal mecA Gene from BACTEC Blood Culture Bottles by the Polymerase Chain Reaction," Am. J. Clin. Pathol. (1996) 106:600-5.

Case et al., "Maternal inheritance of mitochondrial DNA polymorphisms in cultured human fibroblasts," *Somatic Cell Genetics* (1981) 7:103-108.

Cattoli et al., "Comparison of three rapid detection systems for type A influenza virus on tracheal swabs of experimentally and naturally infected birds" Avian Pathology (2004) 33(4):432-437.

Cavassini, M. et al., "Evaluation of MRSA-Screen, a Simple Anti-PBP 2a Slide Latex Agglutination Kit, for Rapid Detection of Methicillin Resistance in *Staphylococcus aureus*," *J. Clin. Microbial.* (1999) 37(5): 1591-1594.

Cespedes et al., "Polymerase chain reaction restriction fragment length polymorphism analysis of a short fragment of the cytochrome b gene for identification of flatfish species" *J. Food Protection* (1998) 61:1684-1685.

Chamberlin et al., "New RNA polymerase from *Escerichia coli* infected with bacteriophage T7" Nature 228:227 (1970).

Chandra, S. et al., "Virus reduction in the preparation and intravenous globulin: in vitro experiments," *Transfusion* (1999) 39(3): 249-257.

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chaves, F. et al., "Molecular Characterization of Resistance to Mupirocin in Methidlin-Susceptible and -Resistant Isolates of *Staphylococcus aureus* from Nasal Samples," *J. Clin. Microbiol.* (2004) 42(2):822-824.

Chelly et al., "Transcription of the dystrophin gene in human muscle and non-muscle tissue" Nature (1988) 333(6176):858-860.

Chen et al., "Universal primers for amplification of mitochondrial small subunit ribosomal RNA-encoding gene in scleractinian corals" *Marine Biotechnology* (2000) 2:146-153.

Chen et al., "A universal PCR primer to detect members of the Potyviridae and its use to examine the taxonomic status of several members of the family" *Archives of Virology* (2001) 146:757-766.

Chen, Y. Z. et al., "A BAC-Based STS-Content Map Spanning a 35-Mb Region of Human Chromosome 1p35-36," Genomics (2001) 74(1):55-70.

Chen, N. et al., "The genomic sequence of ectromelia virus, the causative agent of mousepox," *Virology* (2003) 317:165-186.

Chen et al., "Genetic mapping of the cold-adapted phenotype of B/Ann Arbor/1/66, the master donor virus for live attenuated influenza vaccines (FluMist)" Virology (2006) 345:416-423.

Chen, CH, K. Tang, N. Taranenko and S. Allman, "Laser Desorption Mass Spectrometry for Fast DNA Sequencing," (Nov. 1994), http://www.ornl.gove/sci/techresources/Human_Genome/publicat/94SANTA/sequencing/seqtoc.shtml (787 reexamination).

Chmielewicz, B. et al., "Development of a PCR-Based Assay for Detection, Quantification, and Genotyping of Human Adenoviruses," Clin. Chem., 2005, vol. 51, No. 8, pp. 1365-1373.

Cho et al., "Application of the ribonuclease P (RNase P) RNA gene sequence for phylogenetic analysis of the gene *Saccharomonospora*" *International Journal of Systematic Bacteriology* (1998) 48:1223-1230.

Choi et al., "Detection and subtying of swine influenza H1N1, H1N2 and H3N2 viruses in clinical samples using two multiplex RT-PCR assays" J. Virol. Methods (2002) 102:53-59.

Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426-7433.

Christel, LA et al., "Rapid, Automated Nucleic Acid Probe Assays Using Silicon Microstructures for Nucleic Acid Concentration" J. Biomech. Eng., 1999, 121, 22-27.

Claas, E.C.J. et al., "Internally Controlled Real-Time PCT Monitoring of Adenovirus DNA Load in Serum or Plasma of Transplant Recipients," J. Clin. Microbiol., 2005, vol. 43, No. 4, pp. 1738-1744.

Cloney, L. et al., "Rapid detection of *mecA* in methicillin resistant *Stuphylococcus aureus* using cycling probe technology," *Mol. Cell Probes* (1999) 13:191-197.

Conrads et al., "16S-23S rDNA internal transcribed spacer sequences for analysis of the phylogenetic relationships among species of the genus *Fusobacterium*" *International Journal of Systematic and Evolutionary Microbiology* (2002) 52:493-499.

Contreras-Salazar et al. "up regulation of the Epstein-Barr virus (EBV)-encoded membrane protein LMP in the Burkitt's lymphoma line Daudi after exposure to n-Butyrate and after EBV superinfection" J. Virol. (1990) 64(11):5441-5447.

Cornel et al., "Polymerase chain reaction species diagnostic assay for Anopheles quadrimaculatus cryptic species (Diptera: Culicidae) based on ribosomal DNA ITS2 sequences" *Journal of Medical Entomology* (1996) 33:109-116.

Couto, I. et al., "Devetopment of Methicillin Resistance in Clinical Isolates of *Staphylococcus sciuri* by Transcriptional Activation of the *mecA* Homologue Native to the Species," *J. Bacteriol.* (2003) 185(2):645-653.

Crain et al., "Applications of mass spectrometry of the characterization of oligonucleotides and nucleic acids" *Curr. Opin. Biotechnol.* (1998) 9:25-34.

Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.

Crawford-Miksza, L.K. et al., "Adenovirus Serotype Evolution is Driven by Illegitimate Recombination in the Hypervariable Regions of the Hexon Protein," Virol., 1996, vol. 224, pp. 357 367.

Crawfor-Miksza et al., "Strain variation in adenovirus serotypes 4 and 7a causing acute respiratory disease." (1999) 37:1107-1112.

Crespillo et al., "Mitochondrial DNA sequences for 118 individuals from northeastern Spain" *Int. J. Legal Med.* (2000) 114:130-132.

Cui, L. et al., "Contribution of a Thickened Cell Wall and Its Glutamine Nonamidated Component to the Vancomnycin Resistance Expressed by *Staphylococcus aureus* Mu50," *Antimicrob. Agents Chemother.* (2000) 44(9):2276-2285.

Dasen et al., "Classification and identification of Propionibacteria based on 16S ribosomal RNA genes and PCR" *Systematic and Applied Microbiology* (1998) 21:251-259.

De Sousa, M. A. et al., "Bridges from hospitals to the laboratory: genetic portraits of methicillin-resistant *Staphylococcus aureus* clones," *FEMS Immunol. Med. Microbiol.* (2004) 40:101-111.

Deforce et al., "Analysis of oligonucleotides by ESI-MS" *Advances in Chromatography* (2000) 40:539-566.

Deforce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.

De La Puente-Redondo et al., "Comparison of different PCR approaches for typing of *Francisella tularensis* strains." (2000) 38:1016-1022.

Del Blanco et al., "Genotyping of *Francisella tularensis* strains by pulsed-field gel electrophoresis, amplified fragment length polymorphism fingerprinting, and 16S rRNA gene sequencing." (2002) 40:2964-2972.

Del Vecchio, V. G. et al., "Molecular Genotyping of Methicillin-Resistant *Staphylococcus aureus* via Fluorophore-Enhanced Repetitive-Sequence PCR," *J. Clin. Microbiol.* (1995) 33(8):2141-2144.

Demesure et al., "A set of universal primers for amplification of polymorphic non-coding regions of mitochondrial and chloroplast DNA in plants" *Molecular Ecology* (1995) 4:129-131.

Denis et al., "Development of a semiquantitative PCR assay using internal standard and colorimetric detection on microwell plate for pseudorabies virus" Mol. Cell. Probes (1997) 11(6):439-448.

Deurenberg et al., "Rapid detection of Panton-Valentine leukocidin from clinical isolates of *Staphylococcus aureus* strains by real-time PCR" FEMS Microbiol. Lett. (2004) 240(2):225-228.

Deurenberg et al., "The prevalence of the *Staphylococcus aureus* tst gene among community-and hospital-acquired strains and isolates from Wegener's Granulomatosis patients" FEMS Microbiol. Lett. (2005) 245:185-189.

Dias Neto et al., "Shotgun sequencing of the human transcriptome with ORF expressed sequence tags" *PNAS* (2000) 97:3491-3496.

Di Guilmi, A.M. et al., "Human adenovirus serotype 3 (Ad3) and the Ad3 fiber p[protein bind to a 130-kDa membrane protein on HeLa cells," Virus Res., 1995, vol. 38, pp. 71-81.
Diep, B. A. et al., "Complete genome sequence of USA300, an epidemic clone of community acquired meticillin-resistant *Staphylococcus aureus*," Lancet (2006) 367:731-739.
Dinauer et al., "Sequence-based typing of HLA class II DQB1" *Tissue Anigens* (2000) 55:364-368.
Ding et al., "A high-throughput gene expression analysis technique using competitive PCR and matrix-assisted laser desorption ionization time-of-flight MS" PNAS (2003) 100(6):3059-3064.
Donehower, et al., "The use of primers from highly conserved pol regions to identify uncharacterized retroviruses by the polymerase chain reaction," J. Vir. Methods (1990) 28:33-46.
Donofrio et al., "Detection of influenza A and B in respiratory secretions with the polymerase chain reaction" PCR methods and applications, Cold Spring Harbor Lab. Press vol. 1, No. 4, (1992) pp. 263-268.
Doty et al., Proc. Natl. Acad. Sci. USA 46:461 (1960).
Drosten et al., New England Journal of Medicine, 2003, 348, 1967.
Dubernet et al., "A PCR-based method for identification of *Lactobacilli* at the genus level" *FEMS Microbiology Letters* (2002) 214:271-275.
EBI Accession No. AEM14131 (Jan. 11, 2007)—Bacterial DNA PCR PRIMER SEQ ID No. 874.
Ebner, K. et al., "Molecular Detection and Quantitative Analysis of the Entire Spectrum of Human Adenoviruses by a Two-Reaction Real-Time PCR Assay," J. Clin. Microbiol., 2005, vol. 43, No. 7, pp. 3049-3053.
Ebner et al., "Typing of human adenoviruses in specimens of immunosuppressed patients by PCR-fragment length analysis and real-time quantitative PCR" Journal of Clinical Microbiology (2006) 44:2808-2815.
Echavarria, M. et al., "PCR Method for Detection of Adenovirus in Urine of Healthy and Human Immunodeficiency Virus-Infected Individuals," J. Clin. Microbiol., 1998, vol. 36, No. 11, pp. 3323-3326.
Echavarria, M. et al., "Detection of Adenoviruses (AdV) in Culture-Negative Environmental Samples by PCR During an AdV-Associated Respiratory Disease Outbreak," J. Clin. Microbiol., 2000, vol. 38, No. 8, pp. 2982-2984.
Echavarria, M. et al., "Prediction of severe disseminated adenovirus infection by serum PCR," Lancet, 2001, vol. 358, pp. 384-385.
Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.
Echavarria, M. et al., "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.
Ecker et al., "Rapid identification and strain-typing of respiratory pathogens for epidemic surveillance" PNAS (2005) 102(22):8012-8017.
Ecker et al., "The Ibis T5000 Universal Biosensor: An Automated Platform for Pathogen Identification and Strain Typing" JALA (2006) 11:341-351.
Edwards, K.M. et al., "Adenovirus Infections in Young Children", Pediatrics, 1985, vol. 76, No. 3, pp. 420-424.
Ellis et al., "Molecular diagnosis of influenza" Rev. Med. Virol. (2002) 12(6):375-389.
Elnifro et al., "PCR and Restriction Endonuclease Analysis for Rapid Identification of Adenovirus Subgenera" *Journal of Clinical Microbiology* (2000) 38:2055-2061.
Elsayed, S. et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. (2003) 127:845-849.
EMBL Accession No. S90302, Human, Muscle, Mitochondrial Mutant, 22 nt, segment 2 of 2 (XP002436791) Nov. 26, 1993.
EMBL Accession AJ552897 (Mar. 29, 2003).
EMBL Accession AR321656 (Aug. 12, 2003).
EMBL Accession L15697 (Mar. 4, 2000).
EMBL Accession AB068711 (May 21, 2003).
EMBL Accession Z48571 (Jun. 9 1995).
Enright, M. C, et al., "Multilocus Sequence Typing for Characterization of Methicillin-Resistant and Methicillin-Susceptible Clones of *Staphylococcus aureus*," J. Clin. Microbial. (2000) 38(3): 1008-1015.
Enright, M. C. et al., "The evolutionary history of methicillin-resistant *Staphylococcus aureus* (MRSA)," PNAS(2002) 99(11): 7687-7692.
Enright, M. C. et al., "The evolution of a resistant pathogen—the case of MRSA," Curr. Opin. Pharmacol. (2003) 3:474-479.
Enright, M.C., et al., "Multilocus Sequence Typing of *Streptococcus pyogenes* and the Relationships between emm Type and Clone" Infection and Immunity, 2001, 69, 2416-2427.
Eremeeva et al., "Evaluation of a PCR Assay for Quantitation of *Rickettsia rickettsii* and Closely Related Spotted Fever Group Rickettsiae" J. Clin. Microbiol. (2003) 41(12):5466-5472.
Erlich (ed.). PCR Technology, Stockton Press (1989).
Esmans et al., "Liquid Chromatography-Mass Spectrometry in Nucleoside, nucleotide and modified nucleotide characterization" *J. of Chromatography A* (1998) 794:109-127.
European Patent Office Communication 96(2) EPC for 02709785.6 dated Nov. 20, 2006.
European Patent Office Communication for 06849755.1 dated Mar. 12, 2008.
European Patent Office Communication for 07760292.8 dated Apr. 7, 2009.
European Search Report for 02709785.6 dated Oct. 10, 2005.
European Supplemental Search Report for 03796752.8 dated Aug. 14, 2007.
European Supplemental Search Report for 03810055.8 dated Jul. 9, 2007.
European Supplemental Search Report for 02709785.6-2405 (PCT/US0206763) dated Oct. 12, 2005.
European Supplemental Search Report for 04752257.8 dated Feb. 15, 2006.
European Supplemental Search Report for 05751872.2 dated Jan. 28, 2008.
European Supplemental Search Report for 05753037 dated Aug. 28, 2009.
European Supplemental Search Report for 05856582.1 dated Nov. 10, 2008.
European Supplemental Search Report for 04775904.8 dated Jul. 25, 2008.
Facklam, R., et al., "emm Typing and Validation of Provisional M Types for Group A Streptococci" (1999) Emerging Infectious Diseases, 5, 247-253.
Fang, H. et al., "Rapid Screening and Identification of Methicillin-Resistant *Staphylococcus aureus* from Clinical Samples by Selective-Broth and Real-Time PCR Assay," J. Clin. Microbial. (2003) 41 (7):2894-2899.
Farlow et al., "*Francisella tularensis* Strain Typing Using Multiple-Locus, Variable-Number Tandem Repeat Analysis" Journal of Critical Microbiology, (2001) 39(9):3186-3192.
Farrell, D. J., "The Reliability of Microscan Conventional and Rapid Panels to Identify *Staphylococcus aureus* and Detect Methicillin Resistance: an Evaluation Using the Tube Coagulase Test and mec A PCR," *Pathology* (1997) 29:406-410.
Fedele C G et al., "Multiplex polymerase chain reaction for the simultaneous detection and typing of Polyomavirus JC, BK, and SV40 DNA in clinical samples", Journal of Virological Methods, 82(2), Oct. 1999, pp. 137-144.
Fedele C G et al., "Quantitation of Polyomavirus DNA by a competitive nested polymerase chain reaction," Journal of Virological Methods, 88(1):51-61 (Jul. 2000).
Feng, P., "Impact of molecular biology on the detection of food pathogens" Mol. Biotechnol., 1997, 7, 267-278.
Figueiredo et al., "Identification of Brazilian flaviviruses by a simplified reverse transcription-polymerase chain reaction method using *Flavivirus* universal primers" American Journal of Tropical Medicine and Hygiene (1998) 59:357-362.

Flora, et al., "Dual-micro-ESI source for precise mass determination on a quadrupole time-of-flight mass spectrometer for genomic and proteomic applications" *Anal. Bioanal. Chem.* (2002) 373:538-546.

Fong, W. K., et al., "Rapid Solid-Phase Immunoassay for Detection of Methicillin-Resistant *Staphylococcus aureus* Using Cycling Probe Technology." *J. Clin. Microbiol.* (2000) 38(7): 2525-2529.

Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.

Fox et al., "Identification of *Brucella* by Ribosomal-spacer-region PCR and differentiation of, *Brucella canis* from other *Brucella* spp. pathogenic for humans by carbohdrate profiles" *Journal of Clinical Microbiology* (1998) 36:3217-3222.

Fox et al., "Report of the 'Bioterrorism Workshop' Duke University Thomas Center on Apr. 24, 2002 organized by US Army Research Office" *Journal of Microbiological Methods* (2002) 51:247-254.

Fox, J.P. et al., "The Virus Watch Program: A Continuing Surveillance of Viral Infections in Metropolitan New York Families", Am. J. Epidemiol., 1969, vol. 89, No. 1, pp. 25-50.

Francois et al. "Sequence-specific recognition and cleavage of duplex DNA via triple-helix formation by oligonucleotides covalently linked to a phenanthroline-copper chelate" Proc. Natl. Acad. Sci. USA (1989) 86:9702-9706.

Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.

Fraser et al., "The Minimal Gene Complement of *Mycoplasma genitalium*" *Science* (1995) 270:397-403.

Freiberg et al. Genome-wide mRNA profiling: impact on compound evaluation and target identification in anti-bacterial research. Targets 1(1):20-29 (2002).

Freymuth et al., "Comparison of Multiplex PCR Assays and Conventional Techniques for the Diagnostic of Respiratory Virus Infections in Children Admitted to Hospital with an Acute Respiratory Illness" J. Med. Virol. (2006) 78(11):1498-1504.

Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol, 1997, vol. 8, pp. 31-40.

Fuerstenau et al., "Molecular Weight Determination of Megadalton DNA Electrospray Ions Using Charge Detection Time-of-flight Mass Spectrometry" *Rapid Comm. Mass Spec.* (1995) 9:1528-1538.

Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).

Fujimura, S, et al., "Characterization of the *mupA* Gene in Strains of Methicillin-Resistant *Staphylococcus aureus* with a Low Level of Resistance to Mupirocin," *Antimicrob. Agents Chemother.* (2001) 45(2):641-642.

Fujimura, S. et al., "Isoleucyl-tRNA Synthetase Mutations in *Staphylococcus aureus* Clinical Isolates and In Vitro Selection of Low-Level Mupirocin-Resistant Strains," *Antimicrob. Agents Chemother.* (2003) 47(10): 3373-3374.

Fujioka et al., "Analysis of enterovirus genotypes using single-strand conformation polymorphisms of polymerase chain reaction products" *J. Virol. Meth.* (1995) 51:253-258.

Gabriel et al., "Improved mtDNA sequence analysis of forensic remains using a "mini-primer set" amplification strategy" *Journal of Forensic Sciences* (2001) 46:247-253.

Gall, J.G.D. et al., "Construction and Characterization of Hexon-Chimeric Adenoviruses: Specification of Adenovirus Serotype", J. Virol, 1998, Vol. 72, No. 12, pp. 10260-10264.

Gammelin et al., "Two Subtypes of Nucleoproteins (NP) of Influenza A Viruses" Virology (1989) 170:71-80.

Garcia et al., "Quantitative Real-Time PCR Detection of Rift Valley Fever Virus and Its Application to Evaluation of Antiviral Compounds" J. Clin. Microbiol. (2001) 39(12):4456-61.

Gattermann et al., "Heteroplasmic Point Mutations of Mitochondrial DNA Affecting Subunit I of Cytochrome c Oxidase in Two Patients with Acquired Idiopathic Sideroblastic Anemia" *Blood* (1997) 90:4961-4972.

Gaydos, C.A. et al., "Adenovirus Vaccines in the U.S. Military", Military Med., 1995, vol. 160, No. 6, pp. 300-304.

Geha et al., "Multiplex PCR for Identification of Methicillin-Resistant Staphylococci in the Clinical Laboratory" J. Clin. Microbiol. (1994) 32:1768-1772.

GenBank accession No. AE009948.1 (gi:22535226; Aug. 8, 2002).

GenBank accession No. AE009949.1 (gi:19913450; Apr. 3, 2002).

GenBank accession No. AE015927.1 (gi:28204652; Feb. 4, 2003).

GenBank accession No. AE015929.1 (gi:27316888; Jan. 2, 2003).

GenBank accession No. AF274728 (gi:11612419; Dec. 11, 2000).

GenBank accession No. AF276257.1 (gi:1457889; Jul. 1, 2001).

GenBank Accession AF304460 (Jul. 11, 2001).

GenBank Accession No. M21150 Apr. 26, 1993.

GenBank Accession No. AF375051.1 (Jun. 26, 2001).

GenBank Accession No. BX571857.1 (gi:49243355; Jun. 25, 2004).

GenBank Accession No. Z48571 (Jun. 9, 1995).

GenBank Accession No. X84646 (Jul. 2, 1995).

GenBank GI:147581 [online] Sep. 14, 1992 [retrieved on Jul. 20, 20091 from http://www.ncbi.nlm.nih.gov/sviewer/viewer.fqi?l47581:OLDID:114614.

Genbank GI:15922990 [online] Oct. 4, 2001 [retrieved on Jun. 22, 2008] retrieved from: http://www.ncbi.nlm.nih.gov/entrez/viewer.fcgi?I5922990:OLD08:50885 (pp. 1, 12, 15, 148, 216, 476, 722, 723, 725, 881, 1251).

Genbank GI:18542231 [online] Sep. 16, 2003 [retrieved on Jun. 23, 20081 retrieved from http://www.ncbi.nlm.nih.gov/entrez/viewer.fcgi?db=nuccore&id=I8542231 (2 pages).

GenBank GI:174375 [online] Aug. 11, 1995 [retrieved on Jul. 20, 20091 retrieved from http://www.ncbi.nlm.nih.gov/nuccore/I74375.

Genbank GI:21281729 [online], publicly available at least as of May 31, 2002 [retrieved on Apr. 11, 20081, retrieved from: http://www.ncbi.nlm.nih.gov/entrez/viewer.fcgi?21281729:OLD11:599579 (pp. 1, 723 and 1137).

GenBank GI:42813 [online] Feb. 28, 1992 [retrieved on Jul. 20, 2009] retrieved from the Internet at http://www.ncbi.nlm.nih.gov/sviewer/viewer.fqi?42813:OLDID:25896.

GenBank GI:49243355 [online] Jun. 24, 2004 [retrieved on Jul. 27, 2009] retrieved from http://www.ncbi.nlm.nih.govlsviewer/viewer.fi?49243355:OLDO4:1481434.

GenBank GI:73916349 [online] Sep. 30, 2005 [retrieved on Jul. 25, 2009] retrieved from http://www.ncbi.nlm.nih.gov/nuccore/73916349.

GenBank GI:78099429 [online] Mar. 11, 2006 [retrieved on Jul. 22, 20091 retrieved from http://www.ncbi.nlm.nih.gov/sviewer/viewer.fi?78099429:NCBI:I2971731.

Gendel et al., "Computational analysis of the specificity of 16S rRNA-derived signature sequences for identifying food-related microbes" Food Microbiology (1996) 13:1-15.

Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).

Gilbert et al., "Comparison of commercial assays for the quantitation of HBV DNA load in health care workers: calibration differences" J. Virol. Methods (2002) 100(1-2):37-47.

Giles et al., "Maternal inheritance of human mitochondrial DNA," *PNAS* (1980) 77:6715-6719.

Gill, S. R. et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," *J. Bacteriol.* (2005) 187(7): 2426-2438.

Gilliland et al., "Analysis of cytokine mRNA and DNA: detectionf and quantitation by competitive polymerase chain reaction" PNAS (1990) 87(7):2725-2729.

Ginther et al., "Identifying individuals by sequencing mitochondrial DNA from teeth," *Nature Genetics* (1992) 2:135-138.

Gjoen et al., "Specific detection of coxsackie viruses A by the polymerase chain reaction" Clinical and Diagnostic Virology (1997) 8:183-188.

Golden et al., Pilot Study of COBAS PCR and Ligase Chain Reaction for Detection of Rectal Infections Due to *Chlamydia trachomatis*, J. Clin. Microbiol., 41(5):2174-2175 (May 2003).

Goto et al., "Applications of the partial 16S rDNA sequence as an index for rapid identification of species in the genus *Bacillus*" *J. Gen. Appl. Microbiol.* (2000) 46:1-8.

Gravet et al., "Characterization of a novel structural member, LukE-LukD, of the bi-component staphylococcal leucotoxins family" FEBS Lett. (1998) 436(2):202-208.

Gray, G.C. et al., "Adult Adenovirus Infections: Loss of Orphaned Vaccines Precipitates Military Respiratory Disease Epidernics", Clin. Infect. Diseases, 2000, vol. 31, pp. 663-670.

Greenberg et al., "Intraspecific nucleotide sequence variability surrounding the origin of replication in human mitochondrial DNA," *Gene* (1983) 21:33-49.

Griffey et al., "Detection of base pair mismatches in duplex DNA and RNA oligonucleotides using electrospray mass spectrometry" *Proceedings of SPIE—The International Society for Optical Engineering* (1997) 2985:82-86.

Griffin et al., "Direct genetic analysis by matrix-assisted laser desorption/ionization mass spectrometry" *PNAS* (1999) 96:6301-6306.

Griffin et al., "Single-nucleotide polymorphism analysis by MALDI-TOF mass spectrometry" *Trends in Biotechnology* (2000) 18:77-84.

Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.

Grundmann, H. et al., "Emergence and resurgence of meticillin-resistant *Staphylococcus aureus* as a public-health threat," *Lancet* (2006) 368: 874-885.

Grzybowski "Extremely high levels of human mitochondrial DNA heteroplasmy in single hair roots" *Electrophoresis* (2000) 21:548-553.

Gu, Z et al., "Multiplexed, Real-Time PCR for Quantitative Detection of Human Adenovirus", J. Clin. Microbiol., 2003, vol. 41, No. 10, pp. 4636-4641.

Guatelli et al., "Nucleic Acid Amplification In Vitro: Detection of Sequences with Low Copy Numbers and Application to Diagnosis of Human Immunodeficiency Virus Type 1 Infection" Clin. Microbiol. Rev. (1989) 2(2):217-226.

Haff et al., "Multiplex Genotyping of PCR Products with Mass Tag-Labeled Primers" Nucleic Acids Research (1997) 25(18):3749-3750.

Hahner et al., "Analysis of short tandem repeat polymorphisms by electrospray ion trap mass spectrometry" *Nucleic Acids Research* (2000) 28:E82.

Heim, A. et al., "Rapid and Quantitative Detection of Human Adenovirus DNA by Real-Time PCR", J. Med. Virol., 2003, vol. 70, pp. 228-239.

Haines, J.D., et al., "Medical response to bioterrorism: Are we prepared?" J. Okla. State Med. Assoc. 2000, 93, 187-196.

Hall et al., "Base composition analysis of human mitochondrial DNA using electrospray ionization mass spectrometry: a novel tool for the identification and differentiation of humans" Analytical Biochemistry (2005) 344:53-69.

Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible" *Microbial Drug Resistance* (2006) 12(3): 177-185.

Hamels et al., "Consensus PCR and Microarray for Diagnosis of the Genus *Staphylococcus*, Species, and Methicillin Resistance" BioTechniques (2001) 31(6):1364-1366.

Hammerle et al., "A sensitive PCR assay system for the quantitation of viral genome equivalents: hepatitis C virus (HCV)" Arch. Virol. (1996) 141:2103-2114.

Hannis et al., "Accurate characterization of the tyrosine hydroxylase forensic allele 9.3 through development of electrospray ionization Fourier transform ion cyclotron resonance mass spectrometry" *Rapid Communications in Mass Spectrometry* (1999) 13:954-962.

Hannis et al., "Detection of double-stranded PCR amplicons at the attomole level electrosprayed from low nanomolar solutions using FT-ICR mass spectrometry" *Fresenius Journal of Analytical Chemistry* (2001) 369: 246-251.

Hannis et al., "Genotyping short tandem repeats using flow injection and electrospray ionization Fourier transform ion cyclotron resonance mass spectrometry" *Rapid Communications in Mass Spectrometry* (2001) 15:348-350.

Hannis et al., "Genotyping complex short tandem repeats using electrospray ionization Fourier transform ion cyclotron resonance multistage mass spectrometry" *Proceedings of SPIE—The International Society for Optical Engineering* (2000) 3926:36-47.

Hanssen, A.M. et al., "SCC*mec* in staphylococci: genes on the move," *FEMS Immuol. Med. Microbiol.* (2006) 46:8-20.

Hasebe, F. et al. "Combined Detection and Genotyping of *Chikungunya* Virus by a Specific Reverse Transcription-Polymerase Chain Reaction," *J. Med. Virol.* (2002) 67(3): 370-374.

Hassan et al., "Inter- and Intraspecies Variations of the 16S-23S rDNA Intergenic Spacer Region of Various Streptococcal Species" Systematic and Applied Microbiology (2003) 26(1):97-103.

Haugland et al., "Identification of putative sequence specific PCR primers for detection of the toxigenic fungal species *Stachybotrys chartarum*" Mol. Cell. Probes (1998) 12:387-396.

Hayashi et al., "Phylogenetic analysis of the human gut microbiota using 16S rDNA clone libraries and strictly anaerobic culture-based methods" *Microbiology and Immunology* (2002) 46:535-548.

Henchal et al., "Sensitivity and specificity of a universal primer set for the rapid diagnosis of dengue virus infections by polymerase chain reaction and nucleic acid hybridization" *American Journal of Tropical Medicine and Hygiene* (1991) 45:418-428.

Herrmann et al., "Differentiation of *Chlamydia* spp. By Sequence Determination and Restriction Endonuclease Cleavage of RNase P RNA Genes" *J. Clin. Microbiol.* (1996) 34:1897-1902.

Higgins et al., "Competitive oligonucleotide single-base extension combined with mass spectrometric detection for mutation screening" *BioTechniques* (1997) 23:710-714.

Higgins, J.A., et al., "Sensitive and Rapid Identification of Biological Threat AgentsHiggins et al., Competitive oligonucleotide single-base extension combined with mass spectrometric detection for mutation screening" BioTechniques (1997) 23:710-714. *Ann. NY Acad. Sci.*, 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).

Hiramatsu, K. et al., "The emergence and evolution of methicillin-resistant *Staphylococcus aureus*," *Trends Microbiol.* (2001) 9(10):486-493.

Hoffmann et al., "Rescue of influenza B virus from eight plasmids" *PNAS* (2002) 99:11411-11416.

Hoffmann et al., "Universal primer set for the full-length amplification of all influenza A viruses" *Archives of Virology* (2001) 146:2275-2289.

Hofstadler et al., "TIGER: the universal biosensor" Inter. J. Mass Spectrom. (2005) 242:23-41.

Hodgson et al. Molecular Characterization of the Gene Encoding High-Level Mupirocin Resistance in *Staphylococcus aureus* J2870. Antimicrobial Agents and Chemotherapy 38(5):1205-1208, May 1994.

Holden, M. T. G. et al., "Complete genomes of two clinical *Staphylucuccus aureus* strain: Evidence for the rapid evolution of virulence and drug resistance," *PNAS* (2004) 101(26):9786-9791.

Holland et al., "Mitochondrial DNA Sequence Analysis of Human Skeletal Remains: Identification of Remains from the Vietnam War," *Journal of Forensic Sciences* (1993) 38:542-553.

Holland, M.M. and T.J. Parsons "Mitochondrial DNA analsysis_ Validation and use for forensic casework" (1999) Forensic Science Review, vol. 11, pp. 25-51.

Holm et al., "Removing near-neighbour redundancy from large protein sequence collections" *Bioinformatics* (1998) 14:423-429.

Holmes et al., "Whole-Genome Analysis of Human Influenza A Virus Reveals Multiple Persistent Lineages and Reassortment among Recent H3N2 Viruses" PLoS Biol. (2005) 3(9):1579-1589.

Honda et al., "Universal method of hypersensitive nested PCR toward forensic DNA typing" *International Congress Series* (1998) 7:28-30.

Hongoh et al., "Evaluation of primers and PCR conditions for the analysis of 16s rRNA genes from a natural environment" FEMS Microbiol. Lett. (2003) 221:299-304.

Hood, E., "Chemical and biological weapons: New questions, new answers" Environ. Health Perspect., 1999, 107:931-932.

Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.

Howell et al., "Persistent Heteroplasmy of a Mutation in the Human mtDNA Control Region: Hypermutation as an Apparent Consequence of Simple-Repeat Expansion/Contraction" *Am. J. Hum. Genet.* (2000) 66:1589-1598.

Huber et al., On-line cation exchange for suppression of adduct formation in negative-ion electrospray mass spectrometry of nucleic acids. Anal. Chem. (1998) 70:5288-5295.

Huletsky, A. et al., New real-time PCR assay for rapid detection of methicillin-resistant *Staphylococcus aureus* directly from specimens containing a mixture of staphylococci. J. Clin. Microbial. (2004) 42(5): 1875-84.

Hung, "Detection of SARS coronavirus RNA in the cerebrospinal fluid of a patient with severe acute respiratory syndrome" Clin. Chem. (2003) 49:2108.

Hunag, C. et al., "Detection of arboviral RNA directly from mosquito homogenates by reverse transcription-polymerase chain reaction," *J. Virol. Methods* (2001) 94(1-2): 121-128.

Hurdle, J. G. et al., "Analysis of Mupirocin Resistance and Fitness in *Staphylococcus aureus* by Molecular Genetic and Structural Modeling Techniques," *Antimicrob. Agents Chemother.* (2004) 48(11):4366-4376.

Hurst et al., "MALDI-TOF Analysis of Polymerase Chain Reaction Products from Methanotrophic Bacteria" *Anal. Chem.* (1998) 70:2693-2698.

Hutchison et al., "Maternal inheritance of mammalian mitochondrial DNA," *Nature* (1974) 251:536-538.

Hyde-Deruyscher, R. et al., "Polyomavirus early-late switch is not regulated at the level of transcription initiation and is associated with changes in RNA processing" Proc. Natl. Acad. Sci. USA (1988) 85:8993-8997.

Ieven, M. et al., "Rapid Detection of Methicillin Resistance in Coagulase-Negative Staphylococci by Commercially Available Fluorescence Test," *J. Clin. Microbiol.* (1995) 33(8):2183-2185.

Ihle et al., "Efficient purification of DNA fragments using a protein binding membrane" *Nucleic Acids Research* (2000) 28:e76.

Inglis, T. J. et al., "Rapid Genotypic Confirmation of Methicillin Resistance," *Pathology* (1996) 28(3):259-261.

Ingman et al., "Mitochondrial genome variation and the origin of modern humans" *Nature* (2000) 408:708-713.

Australian Search Report for AU 2003297687 dated Sep. 4, 2008.

Australian Search Report for AU 2003302236 dated Sep. 10, 2008.

Australian Search Report for AU 2004248107 dated Jul. 30, 2008.

Canadian patent office communication for Application No. 2,567,839 dated Apr. 7, 2009.

Canadian patent office communication for Application No. 2,525,498 dated Feb. 5, 2009.

Chinese Office Communication for CN2004800161.9 dated Jun. 12, 2009.

International Prelim. Exam. Report for PCT/US02/20336 dated May 12, 2004.

International Prelim. Exam. Report for PCT/US2005/033707 dated Mar. 20, 2007.

International Search Report for PCT/US02/20336 dated Feb. 3, 2003.

International Search Report for PCT/US02/20336 dated May 12, 2004.

International Search Report for PCT/US02/06763 dated Oct. 23, 2002.

International Search Report for PCT/US03/009802 dated Aug. 20, 2004.

International Search Report for PCT/US03/22835 dated Dec. 12, 2003.

International Search Report for PCT/US03/38757 dated Jun. 24, 2004.

International Search Report for PCT/US03/38795 dated Apr. 19, 2004.

International Search Report for PCT/US03/38830 dated Aug. 25, 2004.

International Search Report for PCT/US03/38505 dated Apr. 12, 2005.

International Search Report for PCT/US03/38761 dated Dec. 30, 2005.

International Search Report for PCT/US04/007236 dated Feb. 24, 2006.

International Search Report for PCT/US2004/011877 dated Apr. 20, 2006.

International Search Report for PCT/US04/012671 dated Sep. 28, 2007.

International Search Report for PCT/US04/015123 dated Oct. 3, 2005.

International Search Report for PCT/US04/015196 dated Jul. 1, 2005.

International Search Report for PCT/US2004/028869 dated Jul. 17, 2006.

International Search Report for PCT/US04/033742 dated May 15, 2006.

International Search Report for PCT/US2005/000386 dated May 9, 2006.

International Search Report for PCT/US05/005356 dated Aug. 7, 2007.

International Search Report for PCT/US05/007022 dated Oct. 20, 2006.

International Search Report for PCT/US2005/018031 dated Jun. 28, 2006.

International Search Report for PCT/US05/018337 dated Oct. 10, 2006.

International Search Report for PCT/US05/024799 dated Dec. 28, 2006.

International Search Report for PCT/US05/030058 dated Aug. 20, 2007.

International Search Report for PCT/US05/033707 dated Feb. 6, 2006.

International Search Report for PCT/US05/06133 dated Jul. 26, 2007.

International Search Report for PCT/US05/09557 dated Sep. 19, 2005.

International Search Report for PCT/US06/007747 dated Sep. 5, 2006.

International Search Report for PCT/US2006/040747 dated Mar. 17, 2009.

International Search Report for PCT/US06/015160 dated Oct. 10, 2006.

International Search Report for PCT/US2006/061307 dated Jan. 9, 2008.

International Search Report for PCT/US2007/020045 dated Jan. 8, 2009.

International Search Report for PCT/US2007/066194 dated Jan. 15, 2008.

International Search Report for PCT/US2008/054926 dated Jan. 26, 2009.

International Search Report for PCT/US2008/057717 dated Jan. 13, 2009.

International Search Report for PCT/US2008/064891 dated Aug. 28, 2008.

International Search Report for PCT/US2008/057901 dated Jun. 29, 2009.

International Search Report for PCT/US2008/065332 dated Nov. 28, 2008.

International Search Report for PCT/US2009/045635 dated Oct. 7, 2009.

Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. Med. Sci. 21-31 (1993) ( 787 reexamination).

Isola et al., "MALDI-TOF mass spectrometric method for detection of hybridized DNA oligomers" *Analytical Chemistry* (2001) 73:2126-2131.

Iqbal et al., "A review of molecular recognition technologies for detection of biological threat agents" Biosensors & Bioelectronics, 15:549-578 (2000).

Ito, T. et al., "Structural Comparison of Three Types of Staphylococcal Cassette Chromosome *mec* Integrated in the Chromosome in Methicillin-Resistant *Staphylococcus aureus*," Antimicrob. Agents Chemother. (2001) 45(5): 1323-1336.

Ito, T. et al., "Insights on antibiotic resistance of *Staphylococcus aureus* from its whole genome: genomic istand SCC," *Drug Resist. Updat.* (2003) 6(1):41-52.

Jackson et al., "Mass spectrometry for genotyping: an emerging tool for molecular medicine" Molecular Medicine Today (2000) 6:271-276.

Jambrina et al., GenBank: AF005737.1 influenza B virus B/Panama/45/90 polymerase (PB2) mRNA, complete cds, (1997), pp. 1-3.

James et al., "*Borelia lonestari* infection after a bite by an *Amblyomma americanum* tick" The Journal of Infectious Diseases (2001) 183:1810-1814.

Jankowski et al., "Mass spectrometry of DNA. Part 2. Quantitative estimation of base composition" *European Journal of Mass Spectrometry in Biochemistry, Medicine, and Environmental Research* (1980) 1:45-52.

Jansen et al., "Genotype-by-environment Interaction in Genetic Mapping of Multiple Quantitative Trait Loci" *Theor. Appl. Genet.* (1995) 91:33-37.

Jaulhac, B. et al., "Specific detection of the toxic shock syndrome toxin-1 gene using the polymerase chain reaction" Mol. Cel. Probes (1991) 5:281-284.

Jaulhac, B. et al., "Synthetic DNA probes for detection of genes for enterotoxins A, B, C, D, E and for TSST-1 in staphylococcal strains," *J. Appl. Bacterial.* (1992) 72(5):386-392.

Jensen et al., "Rapid Identification of Bacteria on the Basis of Polymerase C+A409hain Reaction-Amplified Ribosomal DNA Spacer Polymorphisms" *Appl. Environ. Microbiol.* (1993) 59:945-952.

Jeong, J, et al., "Early Screening of Oxacillin-Resistant *Staphylococcus aureus* and *Staphylcoccus epidermidis* from Blood Culture," *J. Korean Med. Sci.* (2002) 17: 168-172.

Jiang et al., "Multiple Trait Analysis of Genetic Mapping for Quantitative Trait Loci Genetics" *Genetics* (1995) 140:1111-1127.

Jiang et al., "A highly efficient and automated method of purifying and desalting PCR products for analysis by electrospray ionization mass spectrometry." *Anal. Biochem.* (2003) 316:50-57.

Johansson et al., "Evaluation of PCR-based methods for discrimination of *Francisella* species and subspecies and development of a specific PCR that distinguishes the two major subspecies of *Francisella tularensis.*" Journal of Clinical Microbiology (2000) 38:4180-4185.

Johnson et al. "Detection of genes for enterotoxins, exfoliative toxins, and toxic shock Syndrome toxin 1 in *Staphylococcus aureus* by the polymerase chain reaction" J. Clin. Microbiol. (1991) 29:426-430.

Jonas, D. et al., "Rapid PCR-Based Identification of Methicillin-Resistant *Staphylococcus aureus* from Screening Swabs," *J. Clin. Microbiol.* (2002) 40(5): 1821-1823.

Jurinke C et al., "Application of nested PCR and mass specctrometry for DNA based virus detection: HBV-DNA detected in the majority of isolated anti-Hbc positive sera", Genetic Analysis: Biomolecular Engineering, Elsevier Science Publishing, US, 14(3):97-102 (Jan. 3, 1998)+A627+A661.

Jurinke et al., "Detection of hepatitis B virus DNA in serum samples via nested PCR and MALDI-TOF mass spectrometry" *Genetic Analysis: Biomolecular Engineering* (1996) 13:67-71.

Jurinke et al., "MALDI-TOF Mass Spectrometry. A Versatile Tool for High-Performance DNA Analysis" Molecular Biotechnology (2004) 26(2):147-163.

Kacian et al., "A Replicating RNA Molecule Suitable for a Detailed Analysis of Extracellular Evolution and Replication" Proc. Natl. Acad. Sci. USA 69:3038 (1972).

Kageyama et al., "Rapid detection of human fecal *Eubacterium* species and related genera by nested PCR method" *Microbiology and Immunology* (2001) 45:315-318.

Kajon, A.E. et al., "Genome Type Analysis of Brazilian Adenovirus Strains of Serotypes 1, 2, 3, 5, and 7 Collected Between 1976 and 1995", J. Med. Virol., 1999, vol. 58, pp. 408-412.

Katano, H., et al., "Identification of Adeno-associated virus contamination in cell and virus stocks by PCR", Biotechniques, Informa Life Sciences Publishing, Westborough, MA, US, 36(4):676-680 (Apr. 2004).

Katayama, Y. et al., "Genetic Organization of the Chromosome Region Surrounding *mecA* in Clinical Staphylococcal Strains: Role of IS431 -Mediated *mecI* Deletion in Expression of Resistance in med-Canying, Low-Level Methicillin-Resistant *Staphylococcus haemolyticus*," Antimicrob. Agents Chemother. (2001) 45(7): 1955-1963.

Ke et al., "Development of a PCR Assay for Rapid Detection of Enterococci" *Journal of Clinical Microbiology* (1999) 37:3497-3503.

Kearns, A. M. et al., "Rapid detection of methicillin-resistant staphylococci by multiplex PCR," *J. Hosp. Infect.* (1999) 43:33-37.

Khan, A.S., et al., "An outbreak of Crimean-Congo haemorrhagic fever in the United Arab Emirates, 1994-1995" Am. J. Trop. Med. Hyg., 1997, 57, 519-525.

Khan, S. A. et al., "Simultaneous detection of erythromycin-resistant methylase genes *ermA* and *ermC* from *Staphylococcus* spp. By multiplex-PCR," *Mol. Cell Probes* (1999) 13:381-387.

Kidd, A.H. et al., "Rapid Subgenus Identification of Human Adenovirus Isolates by a General PPCR", J. Clin. Microbiol., 1996, vol. 34, No. 3, pp. 622-627.

Kilbourne, "Influenza Pandemics: Can We Prepare for the Unpredictable?" Viral Immunol. (2004) 17(3):350-357.

Kilbourne, "Influenza Pandemics of the 20th Century" Emerg. Infect. Dis. (2006) 12(1):9-14.

Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.

Kim et al. "Identification of Mycobacterial species by comparative sequence analysis of the RNA polymerase gene (rpoB)" Journal of Clinical Microbiology 37(6):1714-1720, Jun. 1999.

Kinney et al., American J. Trop. Med. Hyg., (1998), vol. 59, No. 6, p. 952-954.

Kitagawa et al. "Rapid diagnosis of methicillin-resistant *Staphylococcus aureus* bacteremia by nested polymerase chain reaction" Ann. Surgery (1996) 224:665-671.

Kolbert et al., "Branched-DNA Assay for Detection of the mecA Gene in Oxacillin-Resistant and Oxacillin-Sensitive Staphylococci" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Kramer, L. D. et al., "Dection of St. Louis Encephalitis and Western Equine Encephalomyelitis RNA in Mosquitoes Tested Without Maintainance of a Cold Chain," J. Am. Mosq. Control Assoc. (2001) 17(4): 213-215.

Kramer, L. D. et al., "Dection of Encephalitis Viruses in Mosquitoes (Diptera: Culicidea) and Avian Tissues," *J. Med. Entomol.* (2002) 39(2): 312-323.

Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.

Krahmer et al., "MS for identification of single nucleotide polymorphisms and MS/MS for discrimination of isomeric PCR products" *Anal. Chem.* (2000) 72:4033-4040.

Kroes et al., "Bacterial diversity within the human subgingival crevice," Proc. Natl. Acad. Sci. USA (1999) 96:14547-14552.

Kresken, M. et al., "Prevalence of mupirocin resistance in clinical isolates of *Staphylocoucccus aureus* and *Staphylococcus epidermidis*:

results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in *Staphylococcus aureus* isolates using conventional and molecular methods: a descriptive study from a burns unit with high prevalence of MRSA," J. Clin. Pathol. (2002) 55:745-748.

Krossoy et al., "The putative polymerase sequence of infectious anemia virus suggests a new geneus within the Orthomyxoviridae" Journal of Virology (1999) 73:2136-2142.

Ksiaxek, Thomas G., et al., "A novel coronavirus associated with severe acute respiratory syndrome," New England Journal of Medicine, 348(20):1953-1966 (Apr. 10, 2003).

Kupke et al., "Molecular Characterization of Lantibiotic-synthesizing Enzyme EpiD Reveals a Function for Bacterial Dfp Proteins i Coenzyme A Biosynthesis" *Journal of Biological Chemistry* (2000) 275:31838-31846.

Kuroda, M., et al., "Whole genome Sequencing of meticillin-resistant *Staphylococcus aureus*", The Lancet, 357(9264):1225-1240 (Apr. 21, 2001).

Kwok, S. and R. Hguchi, "Avoiding false positives with PCR" Nature, 1989, 339,237-238.

Labandeira-Rey, M. et al., "*Staphylococcus aureus* Panton Valentine Leukocidin Causes Necrotizing Pneumonia" Sciencexpress Jan. 18, 2007.

Lacroix et al., "PCR-Based Technique for the Detection of Bacteria in Semen and Urine" *J. Microbiol. Meth.* (1996) 26:61-71.

Lacroix, L. et al., "Triplex Formation by Oligonucleotides Containing 5-(1-Propynyl)-2' -deoxyuridine: Decreased Magnesium Dependence and Improved Intracellular Gene Targeting" Biochem. (1999) 38(6):1893-1 901.

Lamb et al., "Sequence of Interrupted and Uninterrupted mRNAs and Cloned DNA Coding for the Two Overlapping Nonstructural Proteins of Influenza Virus" Cell (1980) 21:475-485.

Lambert, A.J. et al., "Detection of North American Eastern and Western Equine Encephalitis Viruses by Nucleic Acid Amplification Assays," *J. Clin. Microbiol.* (2003) 41(1): 379-385.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lebedev, Y. et al "Oligonucleotides containing 2-aminoadenine and 5-methycytosine are more effective as primers for PCR amplification than their nonmodified counterparts" Genetic Analysis: Biomolecular Engineering (1996) 13:15-21.

Lednicky, J. A. et al., "Polyomaviruses and Human Tumors: A Brief Review of Current Concenpts and Interpretations," Front. Biosci. (1999) 4:d153-164.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Lee, J.H. et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," *J. Am. Mosq. Control Assoc.* (2002) 18(1): 26-31.

Leif et al., "Isolation and characterization of the proton-translocating NADH: ubiquinone oxidoreductase from *Escherichia coli*" Eur. J. Biochem. (1995) 230:538-548.

Lengyel, A. et al., "Characterization of the Main Protein Components of Adenovirus Virion and its Possible Use in Laboratory Diagnostics", Acta Microbiol. Immunol. Hung., 1998, vol. 45, Nos. 3-4; pp. 281-283.

Leroy et al., "Diagnosis of Ebola haemorrhagic fever by RT-PCR in an epidemic setting", Journal of Medical Virology, 60:463-467 (2000).

Levi, K. et al., "Evaluation of an Isothermal Signal Amplification Method for Rapid Detection of Methicillin-Resistant *Staphylococcus aureus* from Patient-Screening Swabs," J. Clin. Microbiol. (2003) 41(7):3 187-3191.

Levine et al., "PCR-based detection of *Bacillus anthracis* in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) A 816:107-111.

Lewers et al., "Detection of Linked QTL for Soybean Brown Stem Rot Resistance in 'BSR 101' as Expressed in a Growth Chamber Environment" *Molecular Breeding* (1999) 5:33-42.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. vol. 26, No. 5, pp. 1009-1015.

Li, Q.-G. et al., "Genetic variability of hexon loops 1 and 2 between seven genome types of adenovirus serotype 7", Arch. Virol., 1999, vol. 144, No. 9, pp. 1739-1749.

Li et al., "Screening of the high yield influenza B virus on MDCK cell and cloning of its whole genome" International Congress Series 1263 (2004) 610-614.

Li et al., "Single nucleotide polymorphism determination using primer extension and time of flight mass spectrometry" *Electrophoresis* (1999) 20:1258-1265.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.

Liebermann, H. et al., "Mapping of Epitopes on the Fiber Knobs of Human Adenovirus Serotypes 8 and 15", Intervirology, 2002, vol. 45, pp. 59-66.

Lim et al., "The microRNAs of *Caenorhabditis elegans*" Genes and Development 17:991-1008 (2003).

Limbach, P.A., et al., "Enzymatic Sequencing of Oligonucleotides with Electrospray Mass Spectrometry" 42nd ASMS Conference on Mass Spectrometry (Jun. 1994) ( 787 reexamination).

Limoncu, M. H. et al., "Emergence of phenotypic resistance to ciprofloxacin and levofloxacin in methicillin-resistant and methicillin-sensitive *Staphylococcus aureus* strains," Int. J. Antimicrob. Agents (2003) 21:420-424.

Lin et al., "Oxidative Damage to Mitochondrial DNA in Atrial Muscle of Patients with Atrial Fibrillation," Free Radical Biology and Medicine, 35(10):1310-1318 (2003).

Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.

Lina, G. et al., "Involvement of Panton-Valentine Leukocidin-Producing *Staphylococcus aurues* in Primary Skin Infections and Pneumonia," Clin. Infect. Dis. (1999) 29(5):1128-1132.

Lina, G. et al., "Bacterial Competition for Human Nasal Cavity Colonization: Role of Staphylococcal agr Alleles," Appl. Environ. Microbiol. (2003) 69(1):18-23.

Linssen, B. et al., "Development of Reverse Transcription-PCR Assays Specific for Detection of Equine Encephalitis Viruses," *J. Clin. Microbiol.* (2000) 38(4): 1527-1535.

Little, et al., "Rapid Sequencing of Oligonucleotides by High-Resolution Mass Spectrometry" *J. Am. Chem. Soc.* (1994) 116:4893-4897.

Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet" *Analytical Chemistry* (1997) 69:4540-4546.

Liu et al., "An unusual gene arrangement for the putative chromosome replication origin and circadian expression of dnaN in *Synechococcus* sp. Strain PCC 7942" *Gene* (1996) 172:105-109.

Liu et al., "Improving the microdialysis procedure for electrospray ionization mass spectrometry of biological samples" *Journal of Mass Spectrometry* (1997) 32:425-431.

Liu et al., "Interregional Transmission of the Internal Protein Genes of H2 Influenza Virus in Migratory Ducks from North America to Eurasia" Virus Genes (2004) 29(1):81-86.

Livermore, D. M., "The threat from the pink corner," Ann. Med. (2003) 35(4):226-234.

Loakes et al., "Nitroindoles as universal bases" *Nucleosides and Nucleotides* (1995) 14:1001-1003.

Loo, J. A et al., "Applying Charge Discrimination with Electrospray Ionization-Mass Spectrometry to Protein Analysis," J. Am. Soc. Mass. Spectrom. (1995) 6:1098-1104.

Lott, "Nucleotide Sequence Analysis of the 5-8s rDNA and Adjacent ITS2 Region of *Candida albicans* and Related Species" Yeast, 9:1199-1206 (1999).

Louie, L. et al., "Evaluation of Three Rapid Methods for Detection of Methicillin Resistance in *Staphylococcus aureus*," J. Clin. Microbiol. (2000) 38(6):2170-2173.

Love et al., "Cloning and sequence of the groESL heat-shock operon of *Pasteurella multocida*" *Gene* (1995) 166:179-180.

Lovseth, A. et al., "Modified Multiplex PCR Method for Detection of Pyrogenic Exotoxin Genes in Staphylococcal Isolates," J. Clin. Microbiol. (2004) 42(8):3869-3872.

Lowe et al., "A computer program for selection of oligonucleotide primers for polymerase chain reactions" Nucleic Acids Research, (1990) vol. 18(7):1757-1761.

Lu, X. et al., "Molecular typing of human adenoviruses by PCR and sequencing of a partial region of the hexon gene", Arch. Virol,., 2006, vol. 15, No. 8, pp. 1587-1602.

Ludwig W. "Bacterial phylogeny based on 16s and 23s rRNA sequence analysis" FEMS Microbiol Rev 15(2-3):155-73, Oct. 1994.

Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.

Lukashov, V. V. et al., "Evolutionary Relationships among Parvoviruses: Virus-Host Coevolution among Autonomous Primate Parvoviruses and Links between Adeno-Associated and Avian Parvoviruses," J. Virol. (2001) 75(6):2729-2740.

Ma, X. X. et al., "Novel Type of Staphylococcal Cassette Chromosome mec Identified in Community-Acquired Methicillin-Resistant *Staphylococcus aureus* Strains," Antimicrob. Agents Chemother. (2002) 46(4):1147-1152.

Mack and Sninsky, "A sensitive method for the identification of uncharacterized viruses related to known virus groups: Hepadnavirus model system," Proc. Natl. Acad. Sci. USA (1988) 85:6977-6981.

Magnuson, VL, "Substrate nucleotide-determined non-templated addition of adenine by Taq DNA polymerase: Implications for PCR-based genotyping and cloning" Biotechniques, 21:700-709 (Oct. 1996).

Maiwald et al., "Characterization of contaminating DNA in Taq polymerase which occurs during amplification with a primer set for *Legionella* 5S ribosomal RNA" *Molecular and Cellular Probes* (1994) 8:11-14.

Malasig, M.D. et al., "Simplified Microneutralization Test for Serotyping Adenovirus Isolates", J. Clin. Microbiol., 2001, vol. 39, No. 8, pp. 2984-2986.

Mangrum et al., "Solution composition and thermal denaturation for the production of single-stranded PCR amplicons: piperdine-induced destabilization of the DNA duplex?" *Journal of the American Society for Mass Spectrometry* (2002) 13:232-240.

Manian, F. A., "Asymptomatic Nasal Carriage of Mupirocin-Resistant, Methicillin-Resistant *Staphylococcus aureus* (MRSA) in a Pet Dog Associated with MRSA Infection in Household Contacts." Clin. Infect. Dis. (2003) 36:e26-e28.

Marmur et al., "Strand Separation and Specific Recombination in Deoxyribonucleic Acids: Biological Studies" Proc. Natl. Acad. Sci. USA 46:453 (1960).

Martemyanov et al., "Extremely Thermostable Elongation Factor G from *Aquifex aeolicus*: Cloning, Expression, Purification, and Characterization in a Heterologous Translation System" *Protein Expr. Purif.* (2000) 18:257-261.

Martineau, F. et al., "Species-Specific and Ubiquitous-DNA-Based Assays for Rapid Identification of *Staphylococcus aureus*," *J. Clin. Microbial.* (1998) 36(3):618-623.

Martineau, F. et al., "Development of a PCR Assay for Identification of Staphylococci at Genus and Species Levels," J. Clin. Microbial. (2001) 39(7):2541-2547.

Martin-Lopez, J. V. et al., "Simultaneous PCR detection of ica cluster and methicillin and mupirocin resistance genes in catheter-isolated *Staphylococcus*," Int. Microbial. (2004) 7:63-66.

Mason et al., "Diversity and linkage of replication and mobilisation genes in *Bacillus* rolling circle-replicating plasmids from diverse geographical origins" FEMS Microbiol. Ecol. 2002, 42:235-241.

Matray et al., "Synthesis and properties of RNA analogs—oligoribonucleotide N3'->P5' phosphoramidates" *Nucleic Acids Res* (1999) 3976-3985.

Matsuoka, M. et al., "Characteristic expression of three genes, msr(A), mph(C) and erm(Y), that confer resistance to macrolide antibiotics on *Staphylococcus aureus*," FEMS Microbiol. Lett. (2003) 220:287-293.

May, "Percent sequence identity: The need to be explicit" Structure (2004) 12(5):737-738.

McCabe et al., "Bacterial Species Identification after DNA Amplification with a Universal Primer Pair" *Molecular Genetics and Metabolism* (1999) 66:205-211.

McLafferty et al., "Comparison of Algorithms and Databases for Matching Unknown Mass Spectra" *J. Am. Soc. Mass Spectrom.* (1998).

McLuckey, S.A., et al., "Ion Trap Tandem Mass Spectrometry Applied to Small Multiply Charged Oligonucleotides with a Modified Base," 5 J. Am. Soc. Mass. Spectrom. 1994 5:740-747.

Mehrotra et al., "Multiplex PCR for detection of genes for *Staphylococcus aureus* enterotoxins, exfoliative toxins, toxic shock syndrome toxin 1, and methicillin resistance", Journal of Clinical Microbiology, Washington, DC US 38(3):1032-1035 (Mar. 1, 2000)+A256.

Meiyu et al., "Detection of flaviviruses by reverse transcriptase-polymerase chain reaction with the universal primer set" *Microbiology and Immunology* (1997) 41:209-213.

Mellor et al., "Genotype Dependence of Hepatitis C Virus Load Measurement in Commercially Available Quantitative Assays" J. Clin. Microbiol. (1999) 37(8):2525-2532.

Merlino, J. et at., "New Chromogenic Identification and Detection of *Staphylococcus aureus* and Methicillin-Resistant *S. aureus*." J. Clin. Microbiol (2000) 38(6): 2378-2380.

Merlino, J. et al., "Rapid Detection of Non-Multidrug-Resistant and Multidrug-Resistant Methicillin-Resistant *Staphylococcus aureus* Using Cycling Probe Technology for the mecA Gene," Eur. J. Clin. Microbiol. Infect. Dis. (2003) 22: 322.323.

Messmer et al., "Discrimination of *Streptococcus pneumoniae* from other upper respiratory tract streptococci by arbitrarily primed PCR" *Clinical Biochemistry* (1995) 28:567-572.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miller et al., "A compendium of human mitochondrial DNA control region: development of an international standard forensic database," Croat Med. J. (2001) 42:315-327.

Miragaia, M. et al., "Genetic Diversity among Methicillin-Resistant *Staphylococcus epidemidis* (MRSE)," Microbial Drug Resistance (2005) 11(2):83-93.

Miura-Ochiai, R. et al., "Quantitative detection and rapid identification of human adenoviruses", J. Clin. Microbiol., 2007, vol. 45, No. 3, pp. 958-967.

Mollet et al. "rpoB sequence analysis as a novel basis for bacterial identification" Molecular Microbiology 26(5):1005-1011 (1997).

Monroy, A.M. et al., "Exvaluation of Reverse Transcriptase Polymerase Chain Reaction for the Detection of Eastern Equine Encephalumyelitis Virus during Vector Surveillance," *J. Med. Entomol.* (1996) 33(3): 449-457.

Moore et al., "Development and Evaluation of a Real-Time Nucleic Acid Sequence Based Amplification Assay for Rapid Detection of Influenza A" J. Med. Virol. (2004) 74(4):619-628.

Moricca et al., "Detection of *Fusarium oxysporum* f.sp. Vasinfectum in cotton tissue by polymerase chain reaction" *Plant Pathology* (1998) 47:486-494.

Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.

Morse et al., "Nucleotide Sequence of Part of the ropC Gene Encoding the B Subunit of DNA-Dependent RNA Polymerase from some Gram-Positive Bacteria and Comparative Amino Acid Sequence Analysis" System Appl. Microbiol. (1996) 19:150-157.

Muddiman et al., "Application of secondary ion and matrix-assisted laser desorption-ionization time-of-flight mass spectrometry for the quantitative analysis of biological molecules" Mass Spectrometry Reviews (1995) 14:383-429.

Muddiman et al., "Important aspects concerning the quantification of biomolecules by time-of-flight secondary-ion mass spectrometry" Applied Spectroscopy (1996) 50:161-166.

Muddiman et al., "Characterization of PCR Products from Bacilli Using Electrospray Ionization FTICR Mass Spectrometry" Anal. Chem. (1996) 68:3705-3712.

Muhammad et al., "Electrospray ionization quadrupole time-of-flight mass spectrometry and quadrupole mass spectrometry for genotyping single nucleotide substitutions in intact polymerase chain reaction products in K-ras and p53" Rapid Commun. Mass Spectrom. (2002) 16:2278-2285.

Murakami, K. et al., "Identification of Methicillin-Resistant Strains of Staphylococci by Polymerase Chain Reaction," J. Clin. Microbiol. (1991) 29(10):2240-2244.

Mushegian et al., "A minimal gene set for ceullular life derived by comparison of complete bacterial genomes" Proc. Natl. Acad. Sci. USA (1996) 93:10268-10273.

Na et al., "Detection and typing of respiratory adenoviruses in a single-tube multiplex polymerase chain reaction" Journal of Medical Virology (2002) 66:512-517.

Nagpal et al., "Utility of 16S-23S RNA spacer region methodology: how similar are interspace regions within a genome and between strains for closely related organisms?" Journal of Microbiological Methods (1998) 33:211-219.

Nagy, M. et al., "Sequence Analysis of Porcine Adenovirus Serotype 5 Fibre Gene: Evidence for Recombination", Virus Genes, 2002, vol. 24, No. 2, pp. 181-185.

Nakagawa et al., "Gene sequences and specific detection for Panton-Valentine leukocidin" Biochem. Biophys. Res. Commun. (2005) 328(4):995-1002.

Nakao et al., "Development of a Direct PCR Assay for Detection of the Diphtheria Toxin Gene" J. Clin. Microbiol. (1997) 35:1651-1655.

Narita et al., "Phage conversion of Panton-Valentine leukocidin in Staphylococcus aureus: molecular analysis of a PVL-converting phage, phiSLT" Gene (2001) 268(1-2):195-206.

Naumov et al., "Discrimination of the Soil Yest Species Williopsis saturnus and Williopsis suaveolens by the Polymerase Chain Reaction with the Universal Primer N21" Microbiology (Moscow) (Translation of Mikrobiologiya) (2000) 69:229-233.

Neumann et al., "Host Range Restriction and Pathogenicity in the Context of Influenza Pandemic" Emerg. Infect. Dis. (2006) 12(6):881-886.

New England Biolabs (NEB) Catalog (1998-1999) pp. 1, 79, 121, 284.

Newcombe et al. "PCR of peripheral blood for diagnosis of meningococcal disease" (1996) 34:1637-1640.

Ng et al., "Serial analysis of the plasma concentration of SARS coronavirus RNA in pediatric patients with severe acute respiratory syndrome" Clin. Chem. (2003) 49:2085.

Ng et al., "Quantitative analysis and prognostic implication of SARS coronavirus RNA in the plasma and serum of patients with severe acute respiratory syndrome" Clin. Chem. (2003) 49:1976-1980.

Nilsson et al., "Evaluation of mitochondrial DNA coding region assays for increased discrimination in forensic analysis" Forensic Science International: Genetics (2008) 2:1-8.

Nishikawa et al., "Reconstitution of active recombinant Shiga toxin (Stx)1 from recombinant Stxl-A and Stxl-B subunits independently produced by E. coli clones" FEMS (1999) 178:13-18.

Norder et al., "Typing of Hepatitis B Virus Genomes by a Simplified Polymerase Chain Reaction" J. Med. Virol. (1990) 31:215-221.

Nordhoff, E., et al., "Matrix Assisted Laser Desorption/Ionization Mass Spectrometry of Nucleic Acids with Wavelengths in the Ultraviolet and Infrared" 6 Rapid Commun. Mass Spectrom. 771-776 (1992) ( 787 reexamination).

Nubel et al., "PCR primers to amplify 16S rRNA genes from Cyanobacteria," Applied and Environmental Microbiology, 63(8):3327-3332 (Aug. 1997).

Null et al., "Preparation of single-stranded PCR products for electrospray ionization mass spectrometry using the DNA repair enzyme lambda exonuclease" Analyst (2000) 125:619-626.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Perspectives on the use of electrospray ionization Fourier transform ion cyclotron resonance mass spectrometry for short tandem repeat genotyping in the post-genome era" Journal of Mass Spectrometry (2001) 36:589-606.

Null et al., "Evaluation of sample preparation techniques for mass measurements of PCR products using ESI-FT-ICR mass spectrometry" Journal of the American Society for Mass Spectrometry (2002) 13:338-344.

Null et al., "Determination of a correction to improve mass measurement accuracy of isotopically unresolved polymerase chain reaction amplicons by electrospray ionization Fourier transform ion cyclotron resonance mass spectrometry" Rapid Comm. Mass Spectrom. (2003) 17:1714-1722.

Null et al., "Implications of hydrophobicity and free energy of solvation for characterization of nucleic acids by electrospray ionization mass spectrometry" Anal. Chem. (2003) 75:1331-1339.

Nunes, E. L. et al., "Detection of ileS-2 Gene Encoding Mupirocin Resistance in Methicillin-Resistant Staphylococcus aureus by Multiplex PCR" Diagn. Microbiol. Infect. Dis. (1999) 34(2): 77-81.

Nygren et al., "Quantification of HIV-1 Using Multiple Quantitative Polymerase Chain Reaction Standards and Bioluminometric Detection" Anal. Biochem. (2001) 288(1):28-38.

Oberacher H et al., "Increased foresnic efficiency of DNA fingerprints through simultaneous resolution of length and nucleotide variability by high-performance mass spectrometry," Human Mutation 29(3):427-432 (Mar. 2008)+A613+A714.

Oberacher et al., "Analysis of polymerase chain reaction products by on-line liquid chromatography-mass spectrometry for genotyping of polymeric short tandem repeat loci" (2001) 73:5109-5115.

Oberste, et al., "Molecular phylogeny and proposed classification of the Simian picornaviruses," J. Virol. (2002) 76:1244-1251.

Oberste, et al., "Improved molecular identification of enteroviruses by RT-PCR and amplicon sequencing," J. Clin. Virol. (2003) 26:375-377.

Oberste, et al., "Molecular epidemiology and type-specific detection of echovirus 11 isolates from the Americas, Europe, Africa, Australia, southern Asia and the Middle East," Virus Res. (2003) 91:241-248.

O'Guinn, M.L. et al., "Field Detection of Eastern Equine Encephalitis Virus in the Amazon Basin Region of Peru Using Reverse Transcription-Polymerase Chain Reaction Adapted for Field Identification of Arthropod-Borne Pathogens," Am. J. Trop. Med. Hyg. (2004) 70(2): 164-171.

Oizumi, N, et al., "Relationship between mutations in the DNA gyrase and topoisomerase IV genes and nadifloxacin resistance in clinically isolated quinolone-resistant Staphylococcus aureus," Journal of Infection and Chemotherapy: Official Journal of the Japan Society of Chemotherapy, 7(3):191-194 (Sep. 2001).

Okada, M. et al., "Detection and sequence-based typing of human adenoviruses using sensitive universal primer sets for the hexon gene", Arch. Virol., 2007, vol. 152, No. 1, pp. 1-9.

Okuma, K. et al., "Dissemination of New Methicillin-Resistant Staphylococcus aureus Clones in the Community," J. Clin. Mcrobiol. (2002) 40(11):4289-4294.

Oliveira, D. C. et al., "Genetic Organization of the Downstream Region of the mecA Element in Methicillin-Resistant Staphylococcus aureus Isolates Carrying Different Polymorphisms of This Region," Antimicrob. dients Chemother. (2000) 44(7): 1906-1910.

Oliveira, D. C. et al., "Multiplex PCR Strategy for Rapid Identification of Structural Types and Variants of the mec Element in Methicillin-Resistant *Staphylococcus aureus*," Antimicrob. Agents Chemother. (2002) 46(7):2155-2161.

Olsen et al. "Transhemispheric exchange of Lyme disease spyrochetes by seabirds" Journal of Clinical Microbiology (1995) 33:3270-3274.

Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, vol. 36, No. 11, pp. 3149-3154.

Ostrander, E. A. et al., "Identification and Characterization of Dinucleotide Repeat (CA)n Markers for Genetic Mapping in Dog," Genomics (1993) 16(1):207-213.

Ounissi, H. et al., "Gene Homogeneity for Aminoglycoside-Modifying Enzymes in Gram-Positive Cocci," Antimicrob. Agents Chemother. (1990) 34(11):2164-2168.

Pan, Z.-Q et al., "Oligonucleotide-targeted degradation of U1 and U2 snRNAs reveals differential interactions of simian virus 40 premRNAs with snRNPs," Nucleic Acids Res. (1989) 17(16):6553-6568.

Parson et al., "Population data for 101 Austrian Caucasian mitochondrial DNA d-loop sequences: Application of mtDNA sequence analysis to a forensic case" *Int J. Legal Med.* (1998) 111:124-132.

Pastorino, B. et al., "Development of a TaqMan PCR assay without RNA extraction step for the detection and quantification of African Chikungunya viruses," *J. Virol. Methods* (2005) 124(1-2): 65-71.

Paterson et al., "Fine Mapping of Quantitative Trait Loci Using Selected Overlapping Recombinant Chromosomes, in an Interspecies Cross of Tomato" *Genetics* (1990) 124:735-742.

Pawa, A. et al., "Co-transfer of plasmids in association with conjugative transfer of mupirocin or mupirocin and penicillin resistance in methicillin-resistant *Staphylococcus aureus*;" J. Med. Microbiol. (2000) 49: 1103-1107.

Payne et al. Antimicrobials: The challenge of antibiotic resistant bacterial pathogens: the medical need, the market and prospects for new antimicrobial agents. Current Opinion in Microbiology 7:435-438 (2004).

Peng et al., "Rapid detection of *Shigella* species in environmental sewage by an immunocapture PCR with universal primers" *Applied and Environmental Microbiology* (2002) 68:2580-2583.

Perez-Roth, E. et al., "Multiplex PCR for Simultaneous Identification of *Staphylococcus aureus* and Detection of Methicillin and Mupirocin Resistance," J. Clin. Microbial. (2001) 39(11):4037-4041.

Peters et al., "Quantification of the detection of *Pneumocystis carinii* by DNA amplification" Mol. Cell. Probes (1992) 6:115-117.

Pfeffer, M. et al., "Genus-Specific Detection of Alphaviruses by a Semi-Nested Reverse Transcription-Polymerase Chain Reaction," *Am. J. Trop. Med Hyg.* (1997) 57(6): 709-718.

Pfeffer, M. et al., "Specific Detection of Chikungunya Virus Using a RT-PCR/Nested PCR Combination," *J. Vet. Med. B* (2002) 49(1): 49-54.

Pieles, U, et al., Matrix-Assisted Laser Desorption Ionization Time-of-Flight Spectrometry: A Powerful Tool for the Mass and Sequence Analysis of Natural and Modified Oligonucleotides 21 Nucleic Acids Res. 3191-3196 (1993) (787 reexamination).

Pillai, S.D., :Rapid molecular detection of microbial pathogens: breakthroughs and challenges Arch Virol., 1997, 13 Suppl., 67-82.

Piper, J. et al., "Commercially Available Technique for Rapid Laboratory Detection of Methicillin Resistance Among *Staphylococcus aureus*," Diagn. Microbial. Infect. Dis. (1988) 11(3): 177-180.

Poddar, S.K., "Detection of adenovirus using PCR and molecular beacon", J. Virol. Methods., 1999, vol. 82, No. 1, pp. 19-26.

Pomerantz et al., "Determination of oligonucleotide composition from mass spectrometrically measured molecular weight" *Journal of the American Society for Mass Spectrometry* (1993) 4:204-209.

Pring-Akerblom, P., et al., "PCR-based detection and typing of human adenoviruses in clinical samples", Res. Virol., 1997, vol. 148, No. 3, pp. 225-231.

Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.

Promega T4 Polynucleotide Kinase, Promega Technical Bulletin No. 519, Jul. 2002.

Puthavathana et al., "Molecular characterization of the complete genome of human influenza H5N1 virus isolates from Thailand" J. Gen. Virol. (2005) 86:423-433.

Qadri, S. M. et al., "Rapid Detection of Methicillin-Resistant *Staphylococcus aureus* by Crystal MRSA ID System,"J. Clin. Microbiol. (1994) 32(7):1830-1832.

Raaum, R. L. et al., "Catarrhine primate divergence dates estimated from complete mitochondrial genomes: concordance with fossil and nuclear DNA evidence," *J. Hum. Evol.* (2005) 48:237-257.

Ramisse et al., "Identification and characterization of *Bacillus anthracis* by multiplex PCR analysis of sequences on plasmids pX01 and pX02 and chromosomal DNA" FEMS Microbiology Letters (1996) 145(1):9-16.

Rangarajan, Sampath, et al., "Rapid identification of emerging infectious agents using PCR and electrospray ionization mass spectrometry" Ann. N. Y. Acad. Of Sci (2007) 1102:109-120.

Reid et al., "Primary diagnosis of foot-and-mouth disease by reverse transcription polymerase chain reaction" *Journal of Virological Methods* (2000) 89:167-176.

Reilly et al., "Design and use of 16S ribosomal DNA-directed primers in competitive PCRs to enumerate proteolytic bacteria in the rumen" *Microb. Ecol.* (2002) 43:259-270.

Reischl, Frontiers Biosci., 1996, 1, Application of Molecular Biology-Based Methods to the Diagnosis of Infectious Diseases 1, e72-e77.

Reischl, U. et al., "Rapid Identification of Methicillin-Resistant *Staphylococcuss aureus* and Simultaneous Species Confirmation Using Real-Time Fluorescence PCR," J. Clin. Microbiol. (2000) 38(6):2429-2433.

Roberts, M.M. et al., "Three-Dimensional Structure of the Adenovirus Major Coat Protein Hexon", Science, 1986, vol. 232, No. 4754, pp. 1148-1151.

Robinson, D. A. et al., "Multilocus sequence typing and the evolution of methicillin-resistant *Staphylococcus aureus*," Clin. Microbiol. Infect. (2004) 10:92-97.

Rong et al., "Design and Application of 60mer oligonucleotide microarray in SARS coronavirus detection", Chinese Sci. Bull., 2003, 48, 1165-1169.

Ross et al., "Discrimination of Single-Nucleotide Polymorphisms in Human DNA Using Peptide Nucleic Acid Probes Detected by MALDI-TOF Mass Spectrometry" *Anal. Chem.* (1997) 69:4197-4202.

Ross et al., "Analysis of DNA fragments from conventional and microfabricated PCR devices using delayed extraction MALDI-TOF mass spectrometry" *Anal. Chem.* (1998) 70:2067-2073.

Ruan et al., Comparative full-length genome sequence analysis of 14 SARS coronavirus isolates and common mutations associated with the putative origins of infection, Lancet (2003) 361:1832.

Rota et al., "Sequencing of a cDNA clone of the nucleoprotein gene of influenza B/Ann Arbor/1/86" Nucleic Acids Research (1989) 17:3595.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.

Rupf et al., "Quantitative determination of *Streptococcus* mutans by using competitive polymerase chain reaction" Eur. J. Oral. Sci. (1999) 107(2):75-81.

Russell, K.L. et al., "Transmission Dynamics and Prospective Environmental Sampling of Adenovirus in a Military Recruit Setting", J. Infect. Dis., 2006, vol. 194, No. 7, pp. 877-885.

Sabat, A. et al., "Comparison of PCR-Based Methods for Typing *Staphylococcus aureus* Isolates," J. Clin. Microbiol. (2006) 44(10):3804-3807.

Sackesen, C. et al., "Use of polymerase chain reaction for detection of adenovirus in children with or without wheezing", Turk. J. Pediatr., 2005, vol. 47, No. 3, pp. 227-231.

Sakai, H. et al., "Simultaneous Detection of *Staphylococcus aureus* and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.

Sala et al., "Ambiguous base pairing of the purine analogue 1-(20deoxy-B-D-ribofuranosyl)-imidazole-4-carboxamide during PCR" *Nucl. Acids Res.* (1996) 24:3302-3306.

Sambrook et al., Molecular Cloning: A Laboratory Manual, 2nd Edition, Cold Spring Harbor Press, Cold Spring Harbor, NY 1989.

Sampath et al., "Rapid Identification of Emerging Pathogens: Coronavirus" Emerg. Infect. Dis. (2005) 11(3):373-379.

Sampath et al "Global surveillance of emerging influenza virus genotypes by mass spectrometry" Plos ONE (2007) 5:e489.

Sampath et al "Rapid Identification of Emerging Infectious Agents Using PCR and Electrospray Ionization Mass Spectrometry" Ann. N. Y. Acad. Sci. (2007) 1102:109-120.

Sanchez et al., "Detection and Molecular Characterizatio of Ebola viruses causing disease in human and nonhuman primates" The Journal of Infectious Diseases, 179(1):S164-S169 (1999).

Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.

Sanchez-Seco, M. P. et al., "A generic nested-RT-PCR followed by sequencing for detection and identification of members of the alphavirus genus," *J. Virol. Methods* (2001) 95(1-2): 153-161.

Santos et al. "Identification and phylogenetic sorting of bacterial lineages with universally conserved genes and proteins" Environmental Microbiology 6(7):754-759, Jul. 2004.

Sarantis, H. et al., "Comprehensive Detection and Serotyping of Human Adenoviruses by PCR and Sequencing", J. Clin. Microbial., 2004, vol. 42, No. 9, pp. 3963-3969.

Sauer et al., "A novel procedure for efficient genotyping of single nucleotide polymorphisms" *Nucleic Acids Research* (2000) 28:E13.1.

Scaramozzino et al., "Comparison of Flavivirus universal primer pairs and development of a rapid, highly sensitive heminested reverse transcription-PCR assay for detection of flaviviruses targeted to a conserved region of the NS5 gene sequences" *J. Clin. Microbiol.* (2001) 39:1922-1927.

Schabereiter-Gurtner et al "Application of broad-range 16s rRNA PCR amplification and DGGE fingerprinting for detection of tick-infecting bacteria" *The Journal of Microbiological Methods* (2003 52:251-260.

Scheffner, M. et al., "The E6 Oncoprotein Encoded by Human Papillomavirus Types 16 and 18 Promotes the Degradation of p53," Cell (1990) 63:1129-1136.

Schena M. "Genome analysis with gene expression microarrays" Bioessays (1996) 18:427-431.

Scheuermann et al. "Polymerase chain-reaction-based mRNA quantification Using an internal standard: analysis of oncogene expression" (1993) 218:446-473.

Schlecht, N. F. et al., "Viral Load as a Predictor of the Risk of Cervical Intraepithelial Neoplasia," Int. J. Cancer (2003) 103:519-524.

Schmidt et al., "Analysis of a marine pikoplankton community by 16s rRNA gene cloning and sequencing," J. Bacteriol. (1991) 173:4371-4378.

Schmitz, F. J. et al., "Specific information concerning taxonomy, pathogenicity and methicillin resistance of staphvlococci obtained by a multiplex PCR." J. Med. Microbiol. (1997) 46:773-778.

Schmitz, F. J. et al., "Development of a multiplex-PCR for direct detection of the genes for enterotoxin B and C, and toxic shock syndrome toxin-1 in *Staphylococcus aureus* isolates," J. Med. Microbiol. (1998) 47(4):335-340.

Schmitz, F. J. et al., "Development of Resistance to Ciprofloxacin, Rifampin, and Mupirocin in Methicillin-Susceptible and -Resistant *Staphylococcus aureus* Isolates," Antimicrob. Agents Chemother. (2000) 44(11): 3229-3231.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Schwartz, M, et al., "Prenatal diagnosis of alpha-1-antitrypsin deficiency using polymerase chain reaction (PCR). Comparison of conventional RFLP methods with PCR used in combination with allele specific oligonucleotides or RFLP analysis," 36 Clin. Genet. 419-426 (1989) ( 787 reexamination).

Schweiger et al., "Application of a Fluorogenic PCR Assay for Typing and Subtyping of Influenza Viruses in Respiratory Samples" J. Clin. Microbiol. (2000) 38(4):1552-1558.

Sciacchitano et al., "Analysis of polymerase chain reaction-amplified DNA fragments of clostridium botulinum type E neurotoxin gene by high performance capillary electrophoresis." *J. Liq. Chromatogr. Relat. Technol.* (1996) 19:2165-2178.

Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.

Seifarth, et al., "Rapid identification of all known retroviral reverse transcriptase sequences with a novel versatile detection assay," AIDS Res. Human Retrovir. (2000) 16:721-729.

Sellner, L. N. et al., "Sensitive detection of Ross River virus—a one-tube nested RT-PCR," *J. Virol. Methods* (1994) 49(1): 47-58.

Sellner, L., "A Single-Tube Nested RT-PCR for the Detection of Ross River Virus," *Methods Mol. Biol.* (1998) 92: 145-152.

Senko et al., "Determination of Monoisotopic Masses and Ion Populations for Large Biomolecules from Resolved Isotopic Distributions," *J. Am. Soc. Mass Spectrom.* (1995) 6:229.

Seshadri et al., "Differential Expression of Translational Elements by Life Cycle Variants of *Coxiella burnetii"* Infect. Immun. (1999) 67:6026-6033.

Shadan, F. F. et al., "n-Butyrate, a Cell Cycle Blocker, Inhibits the Replication of Polyomaviruses and Papillomaviruses but Not That of Adenoviruses and Herpesviruses," J. Virol. (1994) 68(8):4785-4796.

Shaver et al., "Variation in 16S-23S rRNA intergenic spacer regions among *Bacillus subtilis* 168 isolates" *Molecular Microbiology* (2001) 42:101-109.

Shaver et al., "Restriction fragment length polymorphism of rRNA operons for discrimination and intergenic spacer sequences for cataloging *Bacillus subtilis* sub-groups" *J. Microbiol Methods* (2002) 50:215-223.

Shi et al., "Design and application of 60mer oligonucleotide microarray in SARS coronavirus detection" Chinese Sci. Bull. (2003) 48:1165-1169.

Shimaoka, M. et al., "Development of Enzyme-Labeled Oligonucleotide Probe for Detection of mecA gene in Methicillin-Resistant *Staphylococcus aureus*," J. Clin. Microbiol (1994) 32(8): 1866-1869.

Shimaoka, M. et al., "Detection of the gene for toxic shock syndrome toxin 1 in *Siaphylococcus aureus* by enzyme-labelled oligonucleotideprobes," J. Med. Microbiol. (1996) 44:215-218.

Shrestha, N. K. et al., "Rapid Identification of *Staphylococcus aureus* and the mecA Gene from BacT/Alert Blood Culture Bottles by Using the Lightcycler System," J. Clin. Microbiol. (2002) 40(1):2659-2661.

Simonsen et al., "The Impact of Influenza Epidemics on Hospitalizations" J. Infect. Dis. (2000) 181:831-837.

Skov, R L. et al., "Evaluation of a new 3-h hybridization method for detecting the mecA gene in *Staphylococcus aureus* and comparison with existing genotypic and phenotypic susceptibility testing methods," J. Antimicrob. Chemother. (1999) 43: 467-475.

Smirnov et al. "Application of DNA-binding polymers for preparation of DNA for analysis by matrix-assisted laser desorption/ionization mass spectrometry." Rapid Comm in Mass Spectrometry (2001) 15:1427-1432.

Smith and Waterman, Adv. Appl. Math., 1981, 2, 482-489.

Song et al., "Identification of cry11-type genes from *Bacilus thuringiensis* strains and characterization of a novel cry11-type gene" App. Environ. Microbiol. (2003) 69:5207-5211.

Spackman et al., "Development of a real-time reverse transcriptase PCR assay for type A influenza virus and the avian H5 and H7 hemagglutinin subtypes" Journal of Clinical Microbiology (2002) 40:3256-3260.

Spiess, et al., Trehalose is a potent PCR enhancer: Lowering of DNA melting temperature and thermal stabilization of Taq polymerase by the disaccharide trehalose, In: Clinical Chemistry, 2004, 50(7):1256-1259.

Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.

Steffens et al., "Sequence analysis of mitochondrial DNA hybervariable regions using infrared fluorescence detection" *BioTechniques* (1998) 24:1044-1046.

Stephensen CB et al., "Phylogenetic analysis of a highly conserved region of the polymerase gene from 11 coronaviruses and development ofa consensus polymerase chain reaction assay" Virus Research Amsterdam NL, 60(2):181-189 (Apr. 1, 1999).

Stone et al., "Rapid detection and simultaneous subtype differentiation of influenza A viruses by real time PCR" (2004) *Journal of Virological Methods* (2004) 117:103-112.

Stoneking et al., "Population variation of human mDNA control region sequences detected by enzymatic amplification and sequence-specific oligonucleotide probes," American Journal of Human Genetics (1991) 48:370-382.

Stratagene, 1988 Catalog, p. 39.

Strommenger, B. et al., "Multiplex PCR Assay for Simultaneous Detection of Nine Clinically Relevant Antibiotic Resistance Genes in *Staphylococcus aureus*," J. Clin. Microbial. (2003) 41(9):4089-4094.

Studdert, M. J. et al., "Polymerase chain reaction tests for the identification of Ross River, Kunjin and Murray Valley encephalitis virus infections in horses," *Aust. Vet. J.* (2003) 81(1-2): 76-80.

Stuhlmeier, R et al., "Fast, simultaneous, and sensitive detection of staphylococci," J. Clin. Pathol. (2003) 56:782-785.

Sumner et al. "PCR Amplification and Comparison of Nucleotide Sequences from the groESL Heat Shock Operon of *Ehrlichia* Species" Journal of Critical Microbiology (1997) 35:2087-2092.

Sundsfjord, A. et al., "Genetic methods for detection of antimicrobial resistance," APMIS (2004) 112:815-837.

Swanborg, R.H., "Human herpesvirus 6 and *Chlamydia pneumoniae* as etiologic agents in multiple sclerosis—a critical review"Microbes and Infection, 4:1327-1333 (2002).

Swaminathan, B., et al., Emerging Infectious Diseases, 2001, 7, 382-389.

Swenson, J. M. et al., "Perfomance of Eight Methods, Including Two New Rapid Methods, for Detection of Oxacillin Resistance in a Challenge Set of *Staphylococcus aureus* Organisms," J. Clin. Microbial. (2001) 39(10):3785-3788.

Takagaki, Y. et at., "Four factors are required for 3'-end cleavage of pre-mRNAs," Genes Dev. (1989) 3:1711-1724.

Takahashi et al., "Characterization of gryA, gryB, grlA and grlB mutations in fluoroquinolone-resistant clinical isolates of *Staphylococcus aureus*" *J. Antimicrob. Chemother* (1998) 41:49-57.

Takahata M, et al., "Mutations in the gyrA and gr1A genes of quinolone-resistant clinical isolates of methicillin-resistant *Staphylococcus aureus*," the Journal of Antimicrobial Chemotherapy, 38(3):543-546 (Sep. 1996).

Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.

Takeuchi et al., "Serotyping of Adenoviruses on Conjunctival Scrapings by PCR and Sequence Analysis" *Journal of Clinical Microbiology* (1999) 37:1839-1845.

Tan, T. Y., "Use of molecular techniques for the detection of antibiotic resistance in bacteria," Expert. Rev. Mol. Diagn. (2003) 3(1):93-103.

Tanabe, F. et al., "The Properties and mec A Gene of the Methicillin-Resistant *Staphylccoccus aureus* Isolated in Fukushima Medical College Hospital," Fukushima J. Med. Sci (1993) 39(1):35-42.

Tang, K., "Matrix-Assisted Laser Desorption/Ionization Mass Spectrometry of Oligonucleotides," Dissertation submitted to the Faculty of Vanderbilt University (Aug. 1994) ( 787 reeamination).

Tang, K, N. I. Taranenko, S.L. Allman, L.Y. Chang and C.H. Chen, "Double-Stranded DNA Analysis by Matrix Assisted Laser Desorption/Ionization," 42nd ASMS Conference on Mass Spectrometry (Jun. 1994) ( 787 reexamination).

Tang, K, N. L. Taranenko, S.L. Allman, L.Y. Chang and C.H. Chen, "Detection of 500-Nucleotide DNA by Laser Desorption Mass Spectrometry," Rapid Commun. Mass Spectrom. (Sep. 1994) 8: 727-730.

Tatuch et al., "Heteroplasmic mtDNA mutation (T-G) at 8993 can cause Leigh disease when the percentage of abnormal mtDNA is high" *Am. J. Hum. Genet.* (1992) 50:852-858.

Tarassishin, L. et al., "Adenovirus core protein VII displays a linear epitope conserved in a range of human adenoviruses", J. Gen. Virol., 1999, vol. 80, pp. 47-50.

Tarassishin, L. et al., "An epitope on the adenovirus fibre tail is common to all human subgroups", Ach. Virol., 2000, vol. 145, pp. 805-811.

Taubenberger et al., "Characterization of the 1918 influenza virus polymerase genes" Nature (2005) 437:889-893.

Taylor, L.H., et al., Philos. Trans. R. Soc. Lond B. Biol. Sci. 2001, 356, 983-989.

Tenover, F. C. et al., "Characterization of a Strain of Community-Associated Methicillin-Resistant *Slaphylococcus aureus* Widely Disseminated in the United States," J. Clin.Microbiol. (2006) 44(1):108-118.

Teramura, T. et al., "Quantitative detection of serum adenovirus in a transplant recipient", Lancet, 2002, vol. 359, pp. 1945.

Thiel, et al., "Infectious RNA transcribed in vitro from a cDNA copy of the human coronavirus genome cloned in vaccinia virus" J. Gen. Virology 2001 82:1273-1281.

Thompson et al., "Influenza-Associated Hospitalizations in the United States" JAMA (2004) 292:1333-1340.

Thompson et al., "Clustal W: Improving the sensitivity of progressive multiple sequence alignment through sequence weighting, position-specific gap penalties and weight matrix choice" Nucleic Acid Res. (1994) 22:4673-80.

Tokue, Y. et al., "Comparison of a Polymerase Chain Reaction Assay and a Conventional Microbiologic Method for Detection of Methicillin-Resistant *Slaphylococcus aureus*," Antimicrob. Agents Chemother. (1992) 36(1):6-9.

Tong et al., "Ligation reaction specificities of an NAD+-dependent DNA ligase from the hyperthermophile *Aquifex aeolicus*" *Nucleic Acids Res* (2000) 28:1447-1454.

Top, F., Jr., "Control of Adenovirus Acute Respiratory Disease in U.S. Army Trainees", Yale J. Biol. Med., 1975, vol. 48, pp. 185-195.

Torroni et al., "Classification of European mtDNAs from an Analysis of Three European Populations" *Genetics* (1996) 144:1835-1850.

Towner, K. J. et al., "Development and evaluation of a PCR-based immunoassay for the rapid detection of methicillin-resistant *Staphylococcus aureus*," J. Med. Microbial. (1998) 47:607-613.

Tsuneyoshi et al., "Mass spectrometric gene diagnosis of one-base substitution from polymerase chain reaction amplified human DNA" (1997) 11:719-722.

Tsunoda et al., Time and Memory Efficient Algorithm for Extracting Palindromic and Repetitive Subsequences in Nucleic Acid Sequences Pacific Symposium on Biocomputing (1999) 4:202-213.

Udo, E. E. et al., "Rapid detection of methicillin resistance in staphylococci using a slide latex agglutination kit," Int. J Antimicrob. Agents. (2000) 15(1):19-24.

Udo, E. E. et al., "Genetic analysis of methicillin-resistant *Staphylococcus aureus* expressing high-and low-level mupirocin resistance."J. Med. Microbiol. (2001) 50:909-515.

Udo, E. E. et al., "A chromosomal location of the mupA gene in *Staphylococcus aureus* expressing high-level mupirocin resistance," J. Antimicrob. Chemother. (2003) 51:1283-1286.

Unal et al., "Detection of Methicillin-Resistant Staphylococci by Using the Polymerase Chain Reaction" J. Clin. Microbiol. (1992) 30:1685-1691.

U.S. Appl. No. 10/318,463 filed Dec. 13, 2002.
U.S. Appl. No. 10/323,186 filed Dec. 18, 2002.
U.S. Appl. No. 10/323,187 filed Dec. 18, 2002.
U.S. Appl. No. 10/324,721 filed Dec. 18, 2002.
U.S. Appl. No. 10/728,486 filed Dec. 5, 2003.
U.S. Appl. No. 11/209,439 filed Aug. 23, 2005.
U.S. Appl. No. 11/233,630 filed Sep. 2, 2005.
U.S. Appl. No. 11/682,259 filed Mar. 5, 2007.
U.S. Appl. No. 60/604,329 filed Aug. 24, 2004.
U.S. Appl. No. 60/632,862 filed Dec. 3, 2004.
U.S. Appl. No. 60/639,068 filed Dec. 22, 2004.
U.S. Appl. No. 60/648,188 filed Jan. 28, 2005.
U.S. Appl. No. 60/658,248 filed Mar. 3, 2005.
U.S. Appl. No. 90/010,209 filed Jun. 27, 2008.
U.S. Appl. No. 90/010,210 filed Jun. 27, 2008.

Upton, A. et al., "Mupirocin and *Staphylococcus aureus*: a recent paradigm of emerging antibiotic resistance," J. Antimicrob. Chemother. (2003) 51: 613-617.

Vabret, A., et al., "Development of a PCR-and hybridization-based assay (PCR Adenovirus Consensusâ) for the detection and the species identification of adenoviruses in respiratory specimens", J. Clin. Virol., 2004, vol. 31, No. 2, pp. 116-122.

Van Aerschot et al., "In search of acyclic analogues as universal nucleosides in degenerate probes" *Nucleosides and Nucleotides* (1995) 14:1053-1056.

Van Baar et al., "Characterization of Bacteria by Matrix Assisted Laser Desorption/Ionization and Electrospray Mass Spectrometry" *FEMS Microbiol. Review* (2000) 24:195-219.

Van Camp et al., "Amplification and sequencing of variable regions in bacteria 23S ribosomal RNA genes with conserved primer sequences" *Current Microbiology* (1993) 27:147-151.

Vanchiere et al. "Detection of BK virus and Simian virus 40 in the urine of healthy children" Journal of Medical Virology (2005) 75:447-454.

Van Der Vossen et al., "DNA based typing, identification and detection systems for food spoilage microorganisms: development and implementation" *Int J. Food Microbiol.* (1996) 33:35-49.

Van Der Zee, et al., "Rapid and alternative screening methods for microbiological analysis" J. AOAC Int., 1997, 80, 934-940.

Van Dinten et al., " Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.

Van Elden et al., "Simultaneous Detection of Influenza Viruses A and B Using Real-Time Quantitative PCR" J. Clin. Microbiol. (2001) 39(1):196-200.

Van Elden et al., "Clinical diagnosis of influenza virus infection: evaluation of diagnostic tools in general practice" Br. J. Gen. Pract. (2001) 51:630-634.

Van Ert et al., "Mass spectrometry provides accurate characterization of two genetic marker types in *Bacillus anthracis*" *Biotechniques* (2004) 37:642-644, 646, 648.

Van Leeuwen, W. B. et al., "Rapid Detection of Methicillin-Resistance in *Staphylococus aureus* Isolates by the MRSA-Screen Latex Agglutination Test,"J. Clin. Microbiol. (1999) 37(9):3029-3030.

Van Leeuwen, W. B. et al., "Multilocus Sequence Typing of *Staphylococcus aureus* with DNA Array Technology," J. Clin. Microbiol. (2003) 41(7):3323-3326.

Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.

Vannuffel, P. et al.. "Specific Detection of Methicillin-Resistant *Staphylococcus* Species by Multiplex PCR," J. Clin Microbiol. (1995) 33(11):2864-2867.

Vannuffel, P. et al., "Rapid and Specific Molecular Identification of Methicillin-Resistant *Staphylococcus aureus* in Endotracheal Aspirates from Mechanically Ventilated Patients," J Clin. Microbiol. (1998) 36(8):2366-2368.

Videla, C. et al., "Genomic analysis of adenovirus isolated from Argentinean children with acute lower respiratory infections", J. Clin. Virol., 1999, vol. 14, pp. 67-71.

Vilchez, Regis A et al., "Detection of polyomavirus simian virus 40 tumor antigen DNA in AIDS related systemic non-Hodgkin lymphoma," J. AIDS Journal of Acquired Immune Deficiency Syndromes, 29(2):109-116 (Feb. 1, 2002).

Voelter C et al., "Screening human tumor samples with a broad-spectrum polymerase chain reaction method for the detection of polyomaviruses", Virology, Academic Press, Orlando, US 237(2):389-396 (Oct. 1997).

Volokhov et al. Microarray analysis of erythromycin resistance determinants. Journal of Applied Microbiology 95:787-798 (2003).

Von Eiff, C. et al., "Pathogenesis of infections due to coagulase-negative staphylococci," Lancet Infect. Dis. (2002) 2:677-685.

Walker, E. S. et al., "A Decline in Mupimcin Resistance in Methicillin-Resistant *Staphylococcus aureus* Accompanied Administrative Control of Prescriptions," J. Clin. Microbiol. (2004) 42(6):2792-2795.

Wallace, et al., "The Enigma of Endonuclease VII. DNA Repair," 2:441-453 (2003).

Wallet, F. et al., "Choice of a routine method for detecting methicillin-resistance in staphylococci,"I Antimicrob. Chemother. (1996) 37:901-909.

Walters et al., "Genotyping single nucleotide polymorphisms using intact polymerase chain reaction products by electrospray quadrupole mass spectrometry" *Rapid Communications in Mass Spectrometry* (2001) 15:1752-1759.

Wang, G. et al., "Targeted Mutagenesis in Mammalian Cells Mediated by Intracellular Triple Helix Formation," Mol. Cell. Biol. (1995) 15(3):1759-1768.

Ward et al., "Design and performance testing of quantitative real time PCR assays for influenza A and B viral load measurement" *Journal of Clinical Virology* (2004) 29:179-188.

Weissenbacher, M. et al., "Etiologic and Clinical Evaluation of Acute Lower Respiratory Tract Infections in Young Argentinean Children: An Overview", Rev. Infect. Dis., 1990, vol. 12, Suppl. 8; pp. S889-S898.

Welham et al., "The Characterization of Micro-organisms by Matrix-assisted Laser Desorption/Ionization Time-of-flight Mass Spectrometry" *Rapid Communications in Mass Spectrometry* (1998) 12:176-180.

Wertheim, H. F. et al., "Effect of Mupirocin Treatment on Nasal, Pharyngeal, and Perineal Carriage of *Staphylococcus aureus* in Healthy Adults," Antimicrob. Agents Chemother. (2005) 49(4):1465-1467.

Westermann, P. et al., "Inhibition of expression of SV40 virus large T-antigen by antisense oligodeoxyribonucleotides," Biomed. Biochim. Acta (1989) 1:85-93.

Whiley, David M et al., "Simultaneous detection and differentiation of human polyomaviruses JC and BK by a rapid and sensitive PCR-ELAHA assay and a survey of the JCV subtypes within an Australian population," Journal of Medical Virology, 72(3):467-472 (Mar. 2004).

Wichelhaus, T. A. et al., "Rapid Detection of Epidemic Strains of Methicillin-Resistant *Staphylococcus aureus*," J. Clin. Microbiol. (1999) 37(3):690-693.

Wickham, T.J., "Targeting adenovirus", Gene Therapy, 2000, vol. 7, pp. 110-114.

Widjojoatmodjo et al. "The magnetic Immuno polymerase chain reaction assay for direct detection of *Salmonellae* in fecal samples" J. Clin. Microbiol. (1992) 30(12):3195-3199.

Widjojoatmodjo et al., "Rapid Identification of Bacteria by PCR-Single-Strand Conformation Polymorphism" *Journal of Clinical Microbiology* Dec. 1994 32:3002-3007.

Winger et al., "High resolution accurate mass measurements of biomolecules using a new electrospray ionization ion cyclotron resonance mass spectrometer" J. Am. Soc. Mass Spectrom. 4, 566, 1993.

Wintzingerode et al. "Base-specific fragmentation of amplified 16s rRNA genes analyzed by mass spectrometry: A tool for rapid bacterial identification" PNAS 99(10):7039-7044, 2002.

Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.

Woo et al., "Identification of *Leptospira inadai* by continuous monitoring of fluorescence during rapid cycle PCR" *Systematic and Applied Microbiology* (1998) 21:89-96.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCR" J. Clin. Microbiol. (1995) 33(5):1180-1184.

Wu et al., "Genetic Organization of the mecA Region in Methicillin-Susceptible and Methicillin-Resistant Strains of *Staphylococcus sciuri*" J. Bacteriol. (1998) 180(2):236-242.

Wu et al., "Establishment of a fluorescent polymerase chain reaction method for the detection of SARS-associated coronavirus and its clinical application" Chin. Med. J. (2003) 116:988-990.

Wunschel et al., "Discrimination Among the *B. cereus* Group, in Comparison to *B. subtilis*, by Structural Carbohydrate Profiles and Ribosomal RNA Spacer Region PCR" *System. Appl. Microbiol.* (1994) 17:625-635.

Wunschel et al., "Analysis of double-stranded polymerase chain reaction products from the *Bacillus cereus* group by electrospray ionization Fourier transform ion cyclotron resonance mass spectrometry" Rapid Communications in Mass Spectrometry (1996) 10:29-35.

Wunschel et al., "Mass spectrometric characterization of DNA for molecular biological applications: Advances using MALDI and ESI" Advances in Mass Spectrometry (1998) 14:Chapter 15/377-Chapter 15/406.

Xu et al. "Electrospray mass tag dideoxy DNA sequencing" Anal. Chem. (1997) 69:3595-3602.

Xu et al., "Intercontinental Circulation of Human Influenza A(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Yasui et al., "A specific oligonucleotide primer for the rapid detection of *Lactobacillus lindneri* by polymerase chain reaction" *Can. J. Microbiol.* (1997) 43:157-163.

Ye, K. et al., "Three Distinct Promoters Direct Transcription of Different 5' Untranslated Regions of the Human Interleukin 1 Type I Receptor: A Possible Mechanism for Control of Translation," Cytokine (1996) 8(6):421-429.

Yun, H J et al., "Increased antibacterial activity of OW286, a novel fluoronaphthyridone antibiotic, against *Staphylococcus aureus* strains with defined mutations in DNA gyrase and toposiomerase IV", International Journal of Antimicrobial Agents, Amsterdam, NL, 25(4):334-337 (Apr. 1, 2005).

Zeng et al., "Precision Mapping of Quantitative Trait Loci" *Genetics* (1994) 136:1457-1468.

Zhang et al., "Detectiona and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of *Staphylococcus aureus* from Coagulase-Negative Staphylococci," J. Clin. Microbiol. (2004) 42(11):4947-4955.

Zhang, Y.-Q. et al., "Genome-based analysis of virulence genes in a non-biofilm-forming *Staphylococcus epidemidis* strain (ATCC 12228):" Mol. Microbiol. (2003) 49(6):1577-1593.

Alba M.M., et al., "VIDA: A Virus Database System for the Organization of Animal Virus Genome Open Reading Frames," Nucleic Acids Research, 2001 vol. 29 (1), pp. 133-136.

Ausubel F.M., et al., eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Benson D.A., et al., "GenBank," Nucleic Acids Research, 1999, vol. 27 (1), pp. 12-17.

Bishop M.J., et al., "Molecular Sequence Databases" in: Nucleic Acid and Protein Sequence Analysis, 4th Chapter, Bishop M.J., et al., eds, IRL Press, 1987, pp. 83-113.

Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.

Butler J., "DNA Profiling and Quantitation of Human DNA," CCQM Bio Analysis Working Group, 2005.

Butler J.M., et al., High Throughput Genotyping of Forensic STRs and SNPs using Time-of-Flight Mass Spectrometry, 9th International Symposium on Human Identification, 1998, Orlando FL.

Certificate of Correction mailed Jan. 6, 2009 for U.S. Appl. No. 10/660,996, filed Sep. 12, 2003.

Certificate of Correction mailed Aug. 7, 2007 for U.S. Appl. No. 10/660,997, filed Sep. 12, 2003.

Certificate of Correction mailed Dec. 12, 2006 for U.S. Appl. No. 10/156,608, filed May 24, 2002.

Certificate of Correction mailed Jul. 17, 2007 for U.S. Appl. No. 09/891,793, filed Jun. 26, 2001.

Certificate of Correction mailed Mar. 31, 2008 for U.S. Appl. No. 09/891,793, filed Jun. 26 2001.

Certificate of Correction mailed Mar. 31, 2008 for U.S. Appl. No. 10/156,608, filed May 24, 2002.

Certificate of Correction mailed Mar. 31, 2008 for U.S. Appl. No. 10/660,997, filed Sep. 12, 2003.

Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.

Chiu N. H., et al., "Mass Spectrometry of Single-Stranded Restriction Fragments Captured by an Undigested Complementary Sequence," Nucleic Acids Research, 2000, vol. 28 (8), pp. E31.

Collins D.W., et al., "Numerical Classification of Coding Sequences," Nucleic Acids Research, 1992, vol. 20 (6), pp. 1405-1410.

Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/674,538, filed Feb. 13, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319, filed Dec. 6, 2002.
Co-pending U.S. Appl. No. 60/443,443, filed Jan. 29, 2003.
Co-pending U.S. Appl. No. 60/443,788, filed Jan. 30, 2003.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494, filed Apr. 9, 2003.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911, filed Oct. 9, 2003.
Co-pending U.S. Appl. No. 60/615,387, filed Sep. 30, 2004.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed Feb. 13, 2006.
Co-pending U.S. Appl. No. 60/771,101, filed May 18, 2006.
Co-pending U.S. Appl. No. 60/773,124, filed Feb. 6, 2006.
Co-pending U.S. Appl. No. 60/891,479, filed Feb. 23, 2007.
Co-pending U.S. Appl. No. 60/941,641, filed Jun. 1, 2007.

Deyde V.M., et al., "Genomic Signature-Based Identification of Influenza A Viruses Using RT-PCR/Electro-Spray Ionization Mass Spectrometry (ESI-MS) Technology," PLoS ONE, 2010, vol. 5 (10), pp. e13293.

Ecker D.J., et al., "Ibis T5000: a universal biosensor approach for microbiology," Nature Reviews Microbiology, 2008, Vol. 6 (7), pp. 553-558.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Enright M.C., et al., "A multilocus sequence typing scheme for *Streptococcus pneumoniae*: identification of clones associated with serious invasive disease," Microbiology, 1998, vol. 144 (Pt 11), pp. 3049-3060.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
European Search Report for Application No. EP10175659.1, mailed on Feb. 9, 2011, 4 pages.
Evans P., et al., "Practical Algorithms for Universal DNA Primer Design: An Exercise in Algorithm Engineering," Currents in Computational Molecular Biology, 2001, Les Publications CRM, pp. 25-26.
Ex Parte Re-Examination Certificate for U.S. Appl. No. 90/010,209, mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447, mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Oct. 24, 2008 for U.S. Appl. No. 11/582,859, filed Oct. 17, 2006.
Examiner Interview Summary mailed Feb. 27, 2006 for U.S. Appl. No. 10/326,644 filed Dec. 18, 2002.
Examiner Interview Summary mailed Jan. 27, 2006 for U.S. Appl. No. 10/323,211 filed Dec. 18, 2002.
Examiner Interview Summary mailed May 28, 2008 for U.S. Application No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20 2009 for U.S. Appl. No. 11/331,987, filed Jan. 13, 2006.
Final Office Action mailed Jun. 23, 2010 for U.S. Appl. No. 11/930,017, filed Oct. 30, 2007.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
GenBank, "{Deletion 6} [Human, Muscle, Mitochondrial Mutant, 22 nt, Segment 2 of 2]," Accession No. S90302.1, Jun. 10, 1992.
GenBank, "Bovine parainfluenza virus 3 strain Shipping Fever, complete genome," Accesion No. AF178655, Sep. 19, 2000.
GenBank "*Escherichia coli* str. K-12 substr. MG1655, Complete Genome," Accession No. NC000913, Oct. 15, 2001.
GenBank, "*Homo sapiens* Haplotype V Mitochondrion, Complete Genome", Accession No. AF381990.1, Dec. 28, 2001.

GenBank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5-similar to SW:COX3_Human P00414 Cytochrome C Oxidase Polypeptide III ;, mRNA sequence", Accession No. BQ581956.1, Jun. 20, 2002.
GenBank, "or72a01.s1 NCI_CGAP_Lu5 *Homo sapiens* cDNA Clone Image:1601352 3-similar to SW:COX1_Human P00395 Cytochrome C Oxidase Polypeptide I ;, mRNA sequence", Accession No. AI002209.1, Jun. 10, 1998.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
HE L., et al, "Development of a Capillary High-performance Liquid Chromatography Tandem Mass Spectrometry System Using Swift Technology in an Ion Trap/Reflectron Time-of-flight Mass Spetrometer," Biochemical and Biophysical Research Communications, 1997, vol. 11, pp. 1739-1748.
International Preliminary Examination Report for Application No. PCT/US2002/06763, mailed on Jun. 11, 2003, 6 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2004/011877, mailed on May 15, 2006, 6 pages.
International Preliminary Report on Patentability and Written Opinion for Application No. PCT/US2005/00386, mailed on Jul. 10, 2006, 6 pages
International Preliminary Report on Patentability and Written Opinion for Application No. PCT/US2005/030058, mailed on Aug. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2006/028397, mailed on Mar. 5, 2007, 14 pages.
International Search Report and Written Opinion for Application No. PCT/US2008/057901, mailed on Aug. 28, 2008, 14 pages.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Kasai H., et al., "Construction of the gyrB Database for the Identification and Classification of Bacteria," Genome Informatics. Workshop on Genome Informatics, 1998, pp. 13-21.
Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.
Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.
Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Laken S.J., et al., "Genotyping by Mass Spectrometric Analysis of Short DNA Fragments," Nature Biotechnology, 1998, vol. 16 (13), pp. 1352-1356.

Marks F., et al., "Genotyping of *Plasmodium falciparum* Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Non-Final Office Action mailed Oct. 2, 2009 for U.S. Appl. No. 11/929,707, filed Oct. 30, 2007.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Oct. 13, 2010 for U.S. Appl. No. 10/754,415, filed Jan. 9, 2004.

Non-Final Office Action mailed Sep. 16, 2009 for U.S. Appl. No. 11/233,630, filed Sep. 21, 2005.

Non-Final Office Action mailed Feb. 23, 2009 for U.S. Appl. No. 10/660,122, filed Sep. 11, 2003.

Non-Final Office Action mailed May 26, 2010 for U.S. Appl. No. 11/869,449, filed Oct. 9, 2007.

Non-Final Office Action mailed Jul. 27, 2006 for U.S. Appl. No. 11/209,439, filed Aug. 8, 2005.

Non-Final Office Action mailed Jun. 28, 2010 for U.S. Appl. No. 11/930,002, filed Oct. 30, 2007.

Non-Final Office Action mailed Sep. 28, 2009 for U.S. Appl. No. 11/930,017, filed Oct. 30, 2007.

Non-Final Office Action mailed Dec. 29, 2010 for U.S. Appl. No. 12/616,422, filed Nov. 11, 2009.

Non-Final Office Action mailed Apr. 30, 2010 for U.S. Appl. No. 11/930,108, filed Oct. 31, 2007.

Notice of Allowance mailed Apr. 1, 2011 for U.S. Appl. No. 11/233,630, filed Sep. 21, 2005.

Notice of Allowance mailed Jun. 3, 2009 for U.S. Appl. No. 11/331,978, filed Jan. 13, 2006.

Notice of Allowance mailed Aug. 5, 2010 for U.S. Appl. No. 11/233,630, filed Sep. 21, 2005.

Notice of Allowance mailed Aug. 6, 2009 for U.S. Appl. No. 10/728,486, filed Dec. 5, 2003.

Notice of Allowance mailed Dec. 10, 2010 for U.S. Appl. No. 11/233,630, filed Sep. 21, 2005.

Notice of Allowance mailed Dec. 10, 2010 for U.S. Appl. No. 11/491,376, filed Jul. 21, 2006.

Notice of Allowance mailed Nov. 12, 2009 for U.S. Appl. No. 10/728,486, filed Dec. 5, 2003.

Notice of Allowance mailed Dec. 15, 2008 for U.S. Appl. No. 11/331,978, filed Jan. 13, 2006.

Notice of Allowance mailed Sep. 18, 2009 for U.S. Appl. No. 10/660,998, filed Sep. 12, 2003.

Notice of Allowance mailed Nov. 24, 2009 for U.S. Appl. No. 11/331,978, filed Jan. 13, 2006.

Notice of Allowance mailed Oct. 29, 2009 for U.S. Appl. No. 10/660,122, filed Sep. 11, 2003.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Office Action mailed Feb. 2, 2011 for U.S. Appl. No. 11/869,449, filed Oct. 9, 2007.

Office Action mailed Feb. 3, 2011 for U.S. Appl. No. 12/326,800, filed Dec. 2, 2008.

Office Action mailed Dec. 4, 2006 for Indian Application No. 1136KOLNP2003, filed Mar. 4, 2002.

Office Action mailed May 4, 2010 for U.S. Appl. No. 90/010,447, filed Apr. 9, 2009.

Office Action mailed May 4, 2010 for U.S. Appl. No. 90/010,448, filed Apr. 9, 2009.

Office Action mailed Nov. 4, 2009 for European Application No. 02709785.6, filed Mar. 4, 2002.

Office Action mailed Aug. 5, 2010 for European Application No. 02709785.6, filed Mar. 4, 2002.

Office Action mailed Jan. 6, 2011 for Israel Application No. 157661, filed Mar. 4, 2002.

Office Action mailed Mar. 6, 2009 for U.S. Appl. No. 11/233,630, filed Sep. 21, 2005.

Office Action mailed Apr. 7, 2009 for Canadian Application No. 2525498, filed May 13, 2004.

Office Action mailed Feb. 7, 2008 for European Application No. 03796752.8, filed Dec. 5, 2003.

Office Action mailed Jun. 7, 2010 for European Application No. 06800205.4, filed 27 Jul. 27, 2006.

Office Action mailed Jan. 8, 2007 for U.S. Appl. No. 09/891,793, filed Jun. 26, 2001.

Office Action mailed Sep. 8, 2006 for Chinese Application No. 02809122.1, filed Mar. 4, 2002.

Office Action mailed Dec. 9, 2009 for U.S. Appl. No. 90/010,210, filed Jun. 27, 2008.

Office Action mailed Dec. 9, 2009 for U.S. Appl. No. 90/010,447, filed Apr. 9, 2009.

Office Action mailed Dec. 9, 2009 for U.S. Appl. No. 90/010,448, filed Apr. 9, 2009.

Office Action mailed Feb. 9, 2007 for Chinese Application No. 02809122.1, filed Mar. 4, 2002.

Office Action mailed Jan. 9, 2008 for Japanese Application No. 2002570692, filed Mar. 4, 2002.

Office Action mailed Nov. 9, 2010 for U.S. Appl. No. 11/331,987, filed Jan. 13, 2006.

Office Action mailed Aug. 10, 2004 for U.S. Appl. No. 10/326,642, filed Dec. 18, 2002.

Office Action mailed Dec. 10, 2009 for U.S. Appl. No. 11/929,910, filed Oct. 30, 2007.

Office Action mailed Feb. 10, 2006 for Australian Application No. 2002244250, filed Mar. 4, 2002.

Office Action mailed Jun. 10, 2009 for U.S. Appl. No. 90/010,210, filed Jun. 27, 2008.

Office Action mailed Jun. 10, 2010 for U.S. Appl. No. 90/010,447, filed Apr. 9, 2009.

Office Action mailed Jun. 10, 2010 for U.S. Appl. No. 90/010,448, filed Apr. 9, 2009.

Office Action mailed Aug. 11, 2010 for U.S. Appl. No. 90/010,447, filed Apr. 9, 2009.

Office Action mailed Aug. 11, 2010 for U.S. Appl. No. 90/010,448, filed Apr. 9, 2009.

Office Action mailed Jun. 11, 2010 for U.S. Appl. No. 90/010,210, filed Jun. 27, 2008.

Office Action mailed May 12, 2002 for U.S. Appl. No. 09/798,007, filed Mar. 2, 2001.

Office Action mailed Aug. 13, 2009 for U.S. Appl. No. 11/674,538, filed Feb. 13, 2007.

Office Action mailed Jul. 13, 2010 for U.S. Appl. No. 11/929,930, filed Oct. 30, 2007.

Office Action mailed Mar. 14, 2011 for U.S. Appl. No. 11/930,002, filed Oct. 30, 2007.

Office Action mailed Dec. 15, 2008 for Israel Application No. 157661, filed Mar. 4, 2002.

Office action mailed Dec. 15, 2010 for Canadian Application No. 2508726, filed Dec. 5, 2003.
Office Action mailed Jan. 15, 2008 for Israel Appl. No. 157661, filed Mar. 4, 2002.
Office Action mailed Mar. 15, 2010 for European Application No. 08730682.5, filed Feb. 25, 2008.
Office Action mailed Apr. 16, 2009 for U.S. Appl. No. 90/010,210, filed Jun. 27, 2008.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Mar. 16, 2010 for Canadian Application No. 2616281, filed Jul. 21, 2006.
Office Action mailed Nov. 16, 2009 for Japanese Application No. 2005508488, filed Dec. 5, 2003.
Office Action mailed Nov. 16, 2009 for Japanese Application No. 2005508560 filed, Dec. 5, 2003.
Office Action mailed Sep. 17, 2008 for European Application No. 03796752.8, filed Dec. 5, 2003.
Office Action mailed Feb. 18, 2010 for European Application No. 03814656.9, filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857, filed Mar. 4, 2002.
Office Action mailed Sep. 18, 2008 for Australian Application No. 2003298030, filed Dec. 5, 2003.
Office Action mailed Sep. 18, 2008 for U.S. Appl. No. 10/660,998, filed Sep. 12, 2003.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Oct. 21, 2005 for U.S. Appl. No. 10/326,641, filed Dec. 18, 2002.
Office Action mailed Sep. 22, 2010 for Canadian Application No. 2510007, filed Dec. 5, 2003.
Office Action mailed Apr. 23, 2010 for U.S. Appl. No. 90/010,210, filed Jun. 27, 2008.
Office Action mailed Oct. 23, 2003 for New Zealand Application No. 527857, filed Mar. 4, 2002.
Office Action mailed Aug. 24, 2010 for U.S. Appl. No. 90/010,210, filed Jun. 27, 2008.
Office Action mailed Dec. 24, 2004 for New Zealand Application No. 527857, filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jul. 24, 2007 for Mexican Application No. PAA2003007927, filed Sep. 2, 2003.
Office Action mailed Jul. 24, 2009 for U.S. Appl. No. 11/754,182, filed May 25, 2007.
Office Action mailed Jun. 24, 2008 for European Application No. 06800205.4, filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Aug. 26, 2010 for Canadian Application No. 2508584, filed Dec. 5, 2003.
Office Action mailed Jul. 27, 2009 for Canadian Application No. 2439655, filed Mar. 4, 2002.
Office Action mailed Jul. 28, 2010 for U.S. Appl. No. 90/010,210, filed Jun. 27 2008.
Office Action mailed Mar. 29, 2010 for Australian Application No. 2006272776, filed Jul. 21, 2006.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Jul. 30, 2009 for Japanese Application No. 2002570692, filed Mar. 4, 2002.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed Nov. 30, 2009 for U.S. Appl. No. 10/660,122, filed Sep. 11, 2003.
Office Action mailed Sep. 30, 2005 for Chinese Application No. 02809122.1, filed Mar. 4, 2002.
Office Action mailed Jan. 31, 2007 for Philippines Application No. PH12003500824, filed Mar. 4, 2002.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pannetier C., et al., "Quantitative Titration of Nucleic Acids by Enzymatic Amplification Reactions run to Saturation," Nucleic Acids Research, 1993, vol. 21 (3), pp. 577-583.
Partial European Search Report for Application No. EP01106974, mailed on Dec. 16, 2002, 2 pages.
Roberts M.S., et al., "Recombination and Migration Rates in Natural Populations of Bacillus subtilis and Bacillus mojavensis," Evolution, 1995, vol. 49 (6), pp. 1081-1094.
Ross P., et al., "High Level Multiplex Genotyping by MALDI-TOF Mass Spectrometry," Nature Biotechnology, 1998, vol. 16 (13), pp. 1347-1351.
Supplementary European Search Report for Application No. EP03814656, mailed on Oct. 16, 2007, 2 pages.
Talaat A.M., et al., "Genome-Directed Primers for Selective Labeling of Bacterial Transcripts for DNA Microarray Analysis," Nature Biotechnology, 2000, vol. 17, pp. 679-682.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Verma S., et al., "Modified Oligonucleotides: Synthesis and Strategy for Users," Annual Review of Biochemistry, 1998, pp. 99-134.
Watanabe K., et al., "ICB Database: the gyrB Database for Identification and Classification of Bacteria," Nucleic Acids Research, 2001, vol. 29 (1), pp. 344-345.
Written Opinion for Application No. PCT/US2004/33742, mailed on May 15, 2006, 5 pages.
Zhang J., et al., "PowerBLAST: A New Network BLAST Application for Interactive or Automated Sequence Analysis and Annotation," Genome Research, 1997, vol. 7 (6), pp. 649-656.
Notice of Allowance mailed May 25, 2011 for U.S. Appl. No. 11/929,707, filed Oct. 30, 2007.

* cited by examiner

Predicted Coverage (hand picked by human)

| 16SrDNA_Bacteria_CVS_1_1.xml coordinates | | | |
|---|---|---|---|
| Entire 'Band' | Forward Primer | Reverse Primer | Rating |
| 56_376 | 56_104 | 318_376 | good region |
| 352_655 | 352_416 | 536_655 | unlikely |
| 579_726 | 579_620 | 680_726 | unlikely |
| 692_838 | 692_738 | 804_838 | unlikely |
| 753_1003 | 753_838 | 919_1003 | unlikely |
| 980_1154 | 980_1017 | 1094_1154 | unlikely |
| 1124_1298 | 1124_1189 | 1243_1298 | good region |
| 1243_1467 | 1243_1298 | 1384_1467 | good region |
| 1449_1815 | 1449_1543 | 1728_1815 | good region |
| 1745_2007 | 1745_1815 | 1955_2007 | good region |
| 2007_2174 | 2007_2045 | 2110_2174 | good region |
| 2200_2493 | 2200_2295 | 2380_2493 | unlikely |

Plot of the Similarity of Regions of E. Coli K-12 to Other Bacterial Genomes

Number of Similar Bacterial Regions

Similarity Peak Location

Gene Description

```
Location   Value   Gene    Description
-------------------------------------------------
3108390    24      pheV    tRNA-Phe
3211984    24      rpoD    RNA polymerase sigma(70) factor
3315895    39      metY    tRNA-Met
3421817    50      rrlD    23S ribosomal RNA
3422140    40      rrlD    23S ribosomal RNA
3422461    45      rrlD    23S ribosomal RNA
3422743    30      rrlD    23S ribosomal RNA
3423023    32      rrlD    23S ribosomal RNA
3423333    48      rrlD    23S ribosomal RNA
3423638    38      rrlD    23S ribosomal RNA
3423935    48      rrlD    23S ribosomal RNA
3424198    38      rrlD    23S ribosomal RNA
3424625    29      alaU    tRNA-Asx
3424764    35      ileU    tRNA-Ile
3424862    52      rrsD    16S ribosomal RNA
3424992    44      rrsD    16S ribosomal RNA
3425327    45      rrsD    16S ribosomal RNA
3425471    51      rrsD    16S ribosomal RNA
3425594    49      rrsD    16S ribosomal RNA
3425864    41      rrsD    16S ribosomal RNA
3426043    40      rrsD    16S ribosomal RNA
3426358    39      rrsD    16S ribosomal RNA
3467975    22      tufA    Protein Chain Elongation
3468679    33      tufA    Protein Chain Elongation
3468890    25      tufA    Protein Chain Elongation
3470868    22      fusA    GTP - binding protein
3470993    29      fusA    GTP - binding protein
3706292    25      proK    tRNA-Pro
3939454    39      rrsC    16S ribosomal RNA
3939743    40      rrsC    16S ribosomal RNA
3939945    41      rrsC    16S ribosomal RNA
3940215    49      rrsC    16S ribosomal RNA
3940309    43      rrsC    16S ribosomal RNA
3940481    45      rrsC    16S ribosomal RNA
3940798    44      rrsC    16S ribosomal RNA
3940921    52      rrsC    16S ribosomal RNA
3941098    31      gltU    tRNA-Val
```

Genomics Database

| Species | Strain | Op | Primer 1 | Primer 2 | Primer 3 | Primer 4 | Primer 5 | ... |
|---|---|---|---|---|---|---|---|---|
| E coli | ATCC₁ | A | [#A #G #C #T] | [#A #G #C #T] | [#A #G #C #T] | [#A #G #C #T] | [#A #G #C #T] | ... |
|  |  | B | [#A #G #C #T] | [#A #G #C #T] | [#A #G #C #T] | [#A #G #C #T] | [#A #G #C #T] | ... |
|  | ATCC₂ | A | [#A #G #C #T] | [#A #G #C #T] | [#A #G #C #T] | [#A #G #C #T] | [#A #G #C #T] | ... |
|  |  | B | [22 35 21 17] | [18 21 26 23] | [15 24 30 27] | [21 29 22 23] | [23 31 24 21] | ... |
| B subtilis | ATCC₁ | A | [#A #G #C #T] | [#A #G #C #T] | [#A #G #C #T] | [#A #G #C #T] | [#A #G #C #T] | ... |
|  |  | B | [#A #G #C #T] |  |  |  | [#A #G #C #T] | ... |
|  | ATCC₂ | ? | [#A #G #C #T] |  |  |  | [#A #G #C #T] | ... |
|  | ATCC₃ | A | [#A #G #C #T] |  |  |  | [#A #G #C #T] | ... |
| ... |  |  |  |  |  | ... |  |  |

- Row-based matching
  - Stricter database reqts
- Look for *exact* matches first
- Missed detection handling
  - Would like to use database strictly
  - Option to allow missed detections (M/N) – need P(prime) / amplicon
- Look for *cloud* matches next
  - Max no. of cloud matches

Single Primer Detections: LLHR Order

| Primer 1 | Primer 2 | Primer 3 | Primer 4 | Primer 5 | ... |
|---|---|---|---|---|---|
| [#A #G #C #T] | [#A #G #C #T] | [#A #G #C #T] | [#A #G #C #T] | [#A #G #C #T] | ... |
| [22 35 21 17] | [18 21 26 23] | [#A #G #C #T] | [#A #G #C #T] | [#A #G #C #T] | ... |
| [#A #G #C #T] | [#A #G #C #T] | [16 23 30 27] | [21 29 22 23] | [#A #G #C #T] | ... |
| [#A #G #C #T] | [#A #G #C #T] | [#A #G #C #T] | [#A #G #C #T] | [23 31 24 21] | ... |
| [#A #G #C #T] | [#A #G #C #T] | [#A #G #C #T] | [#A #G #C #T] | [#A #G #C #T] | ... |

Exact Match    Cloud Match

Output: detection *paths*, amplitudes, LLHRs, P(row), each database row

METHODS AND APPARATUS FOR GENETIC EVALUATION

STATEMENT OF GOVERNMENT SUPPORT

This invention was made with United States Government support under DARPA contract MDA972-00-C-0053. The United States Government has certain rights in the invention.

FIELD OF THE INVENTION

Aspects of the present invention are directed generally to methods and apparatus for evaluating genetic information, and more particularly to identifying a broad range of bioagents based on their genetic information.

BACKGROUND

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure which amplifies a specific target DNA sequence based on the flanking primers used. Finally, detection and data analysis convert the hybridization event into an analytical result.

Other techniques for detection of bioagents include high-resolution mass spectrometry (MS), low-resolution MS, fluorescence, radioiodination, DNA chips and antibody techniques. None of these techniques is entirely satisfactory.

Mass spectrometry provides detailed information about the molecules being analyzed, including high mass accuracy. It is also a process that can be easily automated. However, high-resolution MS alone fails to perform identification of unknown or bioengineered agents, or in environments where there is a high background level of bioagents ("cluttered" background). Moreover, low-resolution MS can fail to detect some known agents, if their spectral lines are sufficiently weak or sufficiently close to those of other living organisms in the sample. DNA chips with specific probes can only determine the presence or absence of specifically anticipated organisms and fail in the presence of an unknown organism. Because there are hundreds of thousands of species of benign bacteria, some very similar in sequence to threat organisms, even arrays with 10,000 probes lack the breadth needed to differentiate one biological member from all others in such a vast population of possibilities.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.* 7:1266-1269, 1996; Muddiman et al., *Anal. Chem.* 69:1543-1549, 1997; Wunschel et al., *Anal. Chem.* 70:1203-1207, 1998; Muddiman et al., *Rev. Anal. Chem.* 17:1-68, 1998). Electro spray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 10:377-382, 1996). The use of matrix-assisted laser desorption ionization-time of flight (MALDI-TOF) mass spectrometry for characterization of PCR products has been described. (Muddiman et al., *Rapid Commun. Mass Spec.* 13:1201-1204, 1999). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by nonrandomly fragmenting the target into a set of single-stranded nonrandom length fragments and determining their masses by MS.

U.S. Pat. No. 5,605,798 describes a fast and highly accurate mass spectrometer-based process for detecting the presence of a particular nucleic acid in a biological sample for diagnostic purposes.

WO 98/21066 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 describe methods of sequencing nucleic acids using mass spectrometry. U.S. Pat. Nos. 5,622,824, 5,872,003 and 5,691,141 describe methods, systems and kits for exonuclease-mediated mass spectrometric sequencing.

Thus, there is a need for a computer-assisted, computationally non-linear method for bioagent identification which is both specific and rapid, and in which no nucleic acid sequencing is required. The present invention addresses this need.

SUMMARY OF THE INVENTION

Aspects of the present invention are directed to automating the determination of a distinguishing genotypic sequence for a biological member comprising, comparing in a computationally non-linear manner a plurality of genotypic sequence regions from a plurality of biological members and determining a distinguishing genotypic sequence for said biological members, whereby said genotypic distinguishing sequence region differentiates said biological members.

A further aspect of the invention is directed to determining computationally in a non-linear manner a number of primer sets needed to provide a desired level of identification of a biological member of a biological sample comprising, determining computationally in a non-linear manner a level of identification obtained from a first primer set as applied to the biological member of said biological sample and repeating these steps with additional primer sets until a level of identification is at least equal to said desired level of identification and determining thereby the number of primer sets needed to provide the level of identification.

A still further aspect of the invention is directed to determining in a non-linear computational manner a number of primer sets needed to provide a desired level of identification of a member of a biological sample comprising obtaining a virtual amplicon of a portion of the member of the biological sample and comparing the virtual amplicon with a database of virtual amplicons, wherein the database contains virtual amplicons of correspondingly identified portions of known members of biological samples, thereby determining a level of identification of the member of the biological sample and repeating these steps with additional virtual amplicons of additional portions of said member of said biological sample until the level of identification is at or above said desired level for said member of the biological sample.

According to still further aspects of the invention, a method of determining in a non-linear computational manner a number of primer sets needed to provide a desired level of identification of a member of a biological sample comprising, obtaining a virtual amplicon of a portion of the member of the biological sample and comparing said virtual amplicon with a database of virtual amplicons, wherein said database contains virtual amplicons of corresponding identified portions of known members of biological samples, thereby determining a level of identification of said member of the biological sample, and repeating these steps with additional virtual amplicons of additional portions of the member of the biological sample until the level of identification is at or above the desired level for the member of said biological sample. In further accordance herewith, this method may be repeated providing a second virtual sample to be analyzed according to the virtual mass spectrometer having the virtual background noise, and obtaining a second real and virtual mass spectrum of the second virtual sample.

An even further aspect of the present invention is directed to a method of determining a similarity criteria of a first virtual mass spectrum of an unknown bioagent as compared to a second virtual mass spectrum of a known bioagent comprising, obtaining the mass spectrum of the first unknown bioagent corresponding to an amplicon secondary to amplification of a known segment delineated by a primer set and comparing that mass spectrum with at least the second virtual mass spectrum of the known bioagent, where the second virtual mass spectrum is of a virtual amplicon that corresponds to an identified portion of the known bioagent whereby the virtual mass spectrum is assigned a rank according to the similarity criteria with the mass spectrum of the first unknown bioagent.

A yet further aspect of the present invention is directed to a method for the generation of a synthetic mass spectrum template comprising obtaining a mass spectrum of a primer pair amplicon from a sample and transforming said mass spectra into a mass spectrum model and storing said template on computer readable medium in computer readable format.

A yet additional aspect of the present invention is directed to a method of grouping a plurality of biological members according to a grouping criteria comprising obtaining at least one grouping criteria by which each biological member is grouped and comparing the grouping criteria of at least one biological member with the grouping criteria of at least one other biological member, thereby determining an interrelatedness between said at least one biological member and said at least one other biological member and grouping said plurality of biological members according to said interrelatedness.

These and other features of the invention will be apparent upon consideration of the following detailed description of preferred embodiments.

BRIEF DESCRIPTION OF THE DRAWINGS

The foregoing summary of the invention, as well as the following detailed description of preferred embodiments, is better understood when read in conjunction with the accompanying drawings, which are included by way of example, and not by way of limitation with regard to the claimed invention.

FIG. 9 shows an illustrative identification of genes in *E. coli* strain k-12 that are highly similar to regions in other bacterial genomes, in accordance with at least one aspect of the present invention.

FIG. 14-A is a graph showing illustrative mass spectrometer data.

FIG. 14-B is a graph showing an illustrative signal model that may be utilized in accordance with at least one aspect of the present invention.

FIG. 14-C is a graph showing an illustrative comparison of the mass spectrometer data of FIG. 14-C with the signal model of FIG. 14-B, in accordance with at least one aspect of the present invention.

FIG. 14-D is a graph showing an illustrative single-hypothesis cross correlation between a plurality of signal models and the mass spectrometer data of FIG. 14-A.

FIG. 14-E is a graph showing an illustrative joint hypothesis detection result using the plurality of signal models of FIG. 14-D and the mass spectrometer data of FIG. 14-A.

FIG. 15 is a tabular representation of an illustrative genomics database and the implementation of an illustrative single-primer detection scheme in accordance with at least one aspect of the present invention.

DETAILED DESCRIPTION OF ILLUSTRATIVE EMBODIMENTS

Overview

Figure 1:
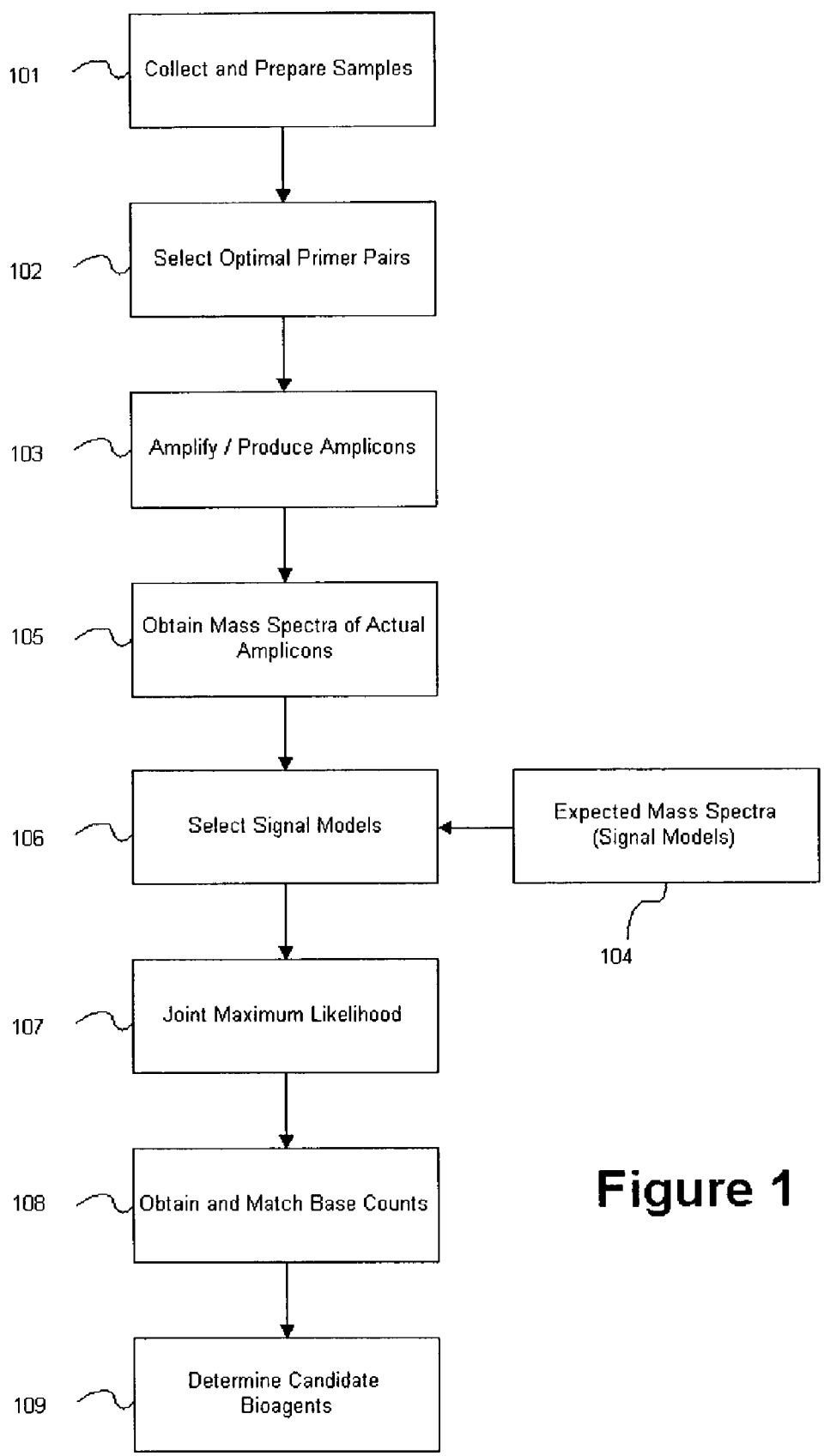
FIG. 1 is a block diagram showing a high-level overview of an illustrative embodiment of the genetic evaluation process, in accordance with at least one aspect of the present invention.

At a high level and referring to FIG. 1, automating the determination of a distinguishing genotypic sequence for a biological member may involve some or all of the following steps (not necessarily in this order): collecting and preparing nucleic acid samples of unknown or suspected bioagents 101; at least computer-aided determination of optimal primer pairs 102; amplifying the nucleic acid using the computer defined primer pairs to form amplicons 103; computer generating expected mass spectra signal models of a plurality of amplicons 104; obtaining the actual mass spectra of the amplicons 105; selecting a subset of the signal models 106; determining through computer evaluation and comparison, the expected mass spectra that most closely correlates with the actual mass spectra using a joint maximum likelihood analysis 107; obtaining base counts for both the actual mass spectra and the selected computer generated expected mass spectra, and matching them 108; and determining and/or ranking the most likely candidate bioagents 109.

One or more of the above may be performed in an iterative manner to further narrow the determined likely candidate bioagents. Embodiments of the present invention may further involve taking account of variations in mass spectra measurements and methods depending on type of mass spectrometer used, variations in nucleic acids for a particular bioagent or set of bioagents, and various scenarios such as expected background clutter, the source of the bioagents, and the like. Variations of this type would be expected when performing real mass spectra. Therefore, throughout this specification and appended claims, the term "real mass spectra" and "real mass spectrum" shall refer to a mass spectrum obtained from a real device and shall include all aspects normally attendant thereto. Aspects attendant thereto are well known in the art and include properties discussed above as well as others not mentioned yet known and accepted by the ordinary practitioner.

Primer design and selection methods may be used to identify oligonucleotide primer pairs that produce "amplicons" (i.e., double-stranded DNA amplification products) of nucleic acid sequences that facilitate the bioagent identification. According to one embodiment of the present invention, computer search algorithms are employed to analyze multiple alignments of numerous biological members, perhaps of different biological families. The computer algorithm may be of those known in the art but is directed to the selection of primer pairs that bind to conserved regions of the DNA that flank a variable region. According to a preferred embodiment of the present invention, a high-resolution mass spectrometer is used to determine the molecular mass of the amplicons. This molecular mass is further used to determine the base count of the amplicon. A "base count" (or "base composition") is the number of each nucleotide base in the examined amplicon. The base counts are then input to a maximum-likelihood, or similar, detection algorithm for comparison against a database of base-counts in the same amplified region. Thus, the present method combines amplification technology (which provides specificity) and a molecular mass detection mode (which provides speed and does not require nucleic acid sequencing of the amplified target sequence) for bioagent detection and identification.

Methods described herein allow extremely rapid and accurate detection and identification of bioagents compared to existing methods. Furthermore, this rapid detection and identification is possible even when sample material is impure. Thus, these methods are useful in a wide variety of fields, including, but not limited to, environmental testing (e.g., detection and discrimination of pathogenic vs. non-pathogenic bacteria in water or other samples), germ warfare (allowing immediate identification of the bioagent and appropriate treatment), pharmacogenetic analysis and medical diagnosis (including cancer diagnosis based on mutations and polymorphisms, drug resistance and susceptibility testing, screening for and/or diagnosis of genetic diseases and conditions, and diagnosis of infectious diseases and conditions). The methods take advantage of ongoing biomedical research in virulence, pathogenicity, drug resistance, and genome sequencing to provide greatly improved sensitivity, specificity, and reliability compared to existing methods.

A "bioagent" is any organism, living or dead, or a nucleic acid derived from such an organism. Examples of bioagents include, but are not limited to, cells (including human clinical samples, bacterial cells, and other pathogens) viruses, fungi, and mycoplasma. Samples may be alive or dead or in a vegetative state (for example, vegetative bacteria or spores) and may be encapsulated or bioengineered. Any bioagent can be detected and classified using methods described herein. As one example, where the bioagent is a biological threat organism, the information obtained can be used to determine practical information needed for countermeasures, including the presence in the bioagent of toxin genes, pathogenicity islands, and antibiotic resistance genes. In addition, the methods can be used to identify natural or deliberate engineering events, including chromosome fragment swapping and molecular breeding (gene shuffling). Emerging infectious disease agents can be detected and tracked.

Primer Design and Selection

Selection of primers is based on the fact that bacteria have a common set of absolutely required genes. See application Ser. Nos. 09/798,007, now abandoned and 09/891,793, now U.S. Pat. No. 7,217,510 For example, about 250 genes are present in all bacterial species (*Proc. Natl. Acad. Sci. U.S.A.* 93, 10268, 1996; *Science* 270, 397, 1995), including tiny genomes such as *Mycoplasma, Ureaplasma,* and *Rickettsia*. These genes encode proteins involved in translation, replication, recombination and repair, transcription, nucleotide metabolism, amino acid metabolism, lipid metabolism, energy generation, uptake, secretion and the like. Examples of such proteins are DNA polymerase III beta, elongation factor TU, heat shock protein groEL, RNA polymerase beta, phosphoglycerate kinase, NADH dehydrogenase, DNA ligase, DNA topoisomerase, and elongation factor G. Variations in such genes can be used to detect and identify individual species of bioagents. Operons, such as the bfp operon from enteropathogenic *E. coli,* can also be identified. Multiple core chromosomal genes can be used to classify bioagents at a genus or species level to determine if a bioagent has threat potential. The method can also be used to detect pathogenicity markers (plasmid or chromosomal) and antibiotic resistance genes to confirm the threat potential of a bioagent and to direct countermeasures.

Although fictional, a perfect and ideal bioagent detector might identify, quantify, and report the complete nucleic acid sequence of every bioagent that reached the sensor. The complete sequence of the nucleic acid component of a pathogen would provide all relevant information about the threat, including its identity and the presence of drug-resistance or pathogenicity markers. This ideal has not yet been achieved. However, the present invention provides a straightforward strategy for obtaining information with the same practical value using base counts. While the base count of a biological fragment is not as information-rich as the entire biological sequence, where the analyte sequence fragment is properly chosen there may be no need to know the complete sequence.

A database of reference sequences can be prepared in which each sequence is indexed to a base count, so that the presence of the sequence can be inferred with accuracy from the presence of a mass spectroscopy signature corresponding to the base count. The advantage of base counts is that they can be quantitatively measured in a massively parallel fashion, for example, using multiplex PCR (PCR in which two or more primer pairs amplify target sequences simultaneously) and mass spectrometry. Cluster-specific primer pairs can be used to distinguish important local clusters (e.g., the *Anthracis* group).

Primers useful in methods of the invention are primers that bind to nucleotide sequence regions that flank an intervening variable region. In a preferred embodiment, the nucleotide sequence regions that flank the variable region are highly conserved among different species. For example, the nucleotide sequence regions may be highly conserved among all *Bacillus* or *Anthracis* species. Highly conserved sequences exhibit between about 80-100%, more preferably between about 90-100%, and most preferably between about 95-100% identity. The invention provides several methods for identifying such primers.

1. Procedure Using Prior Alignment of Nucleotide Sequences

Figure 2:
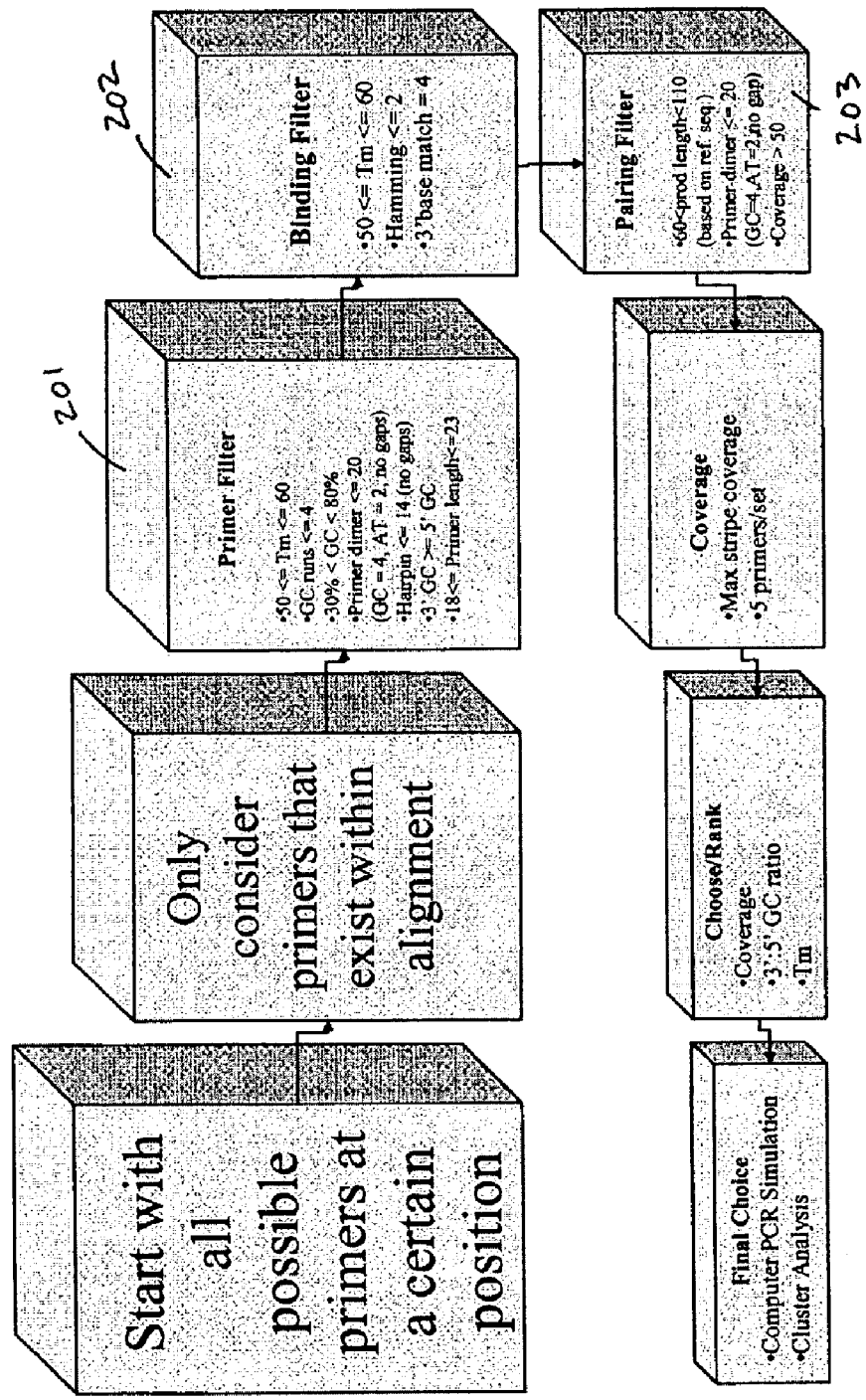
FIG. 2 is a functional block diagram of an illustrative embodiment of a primer selection method in accordance with at least one aspect of the present invention.
Figure 3:
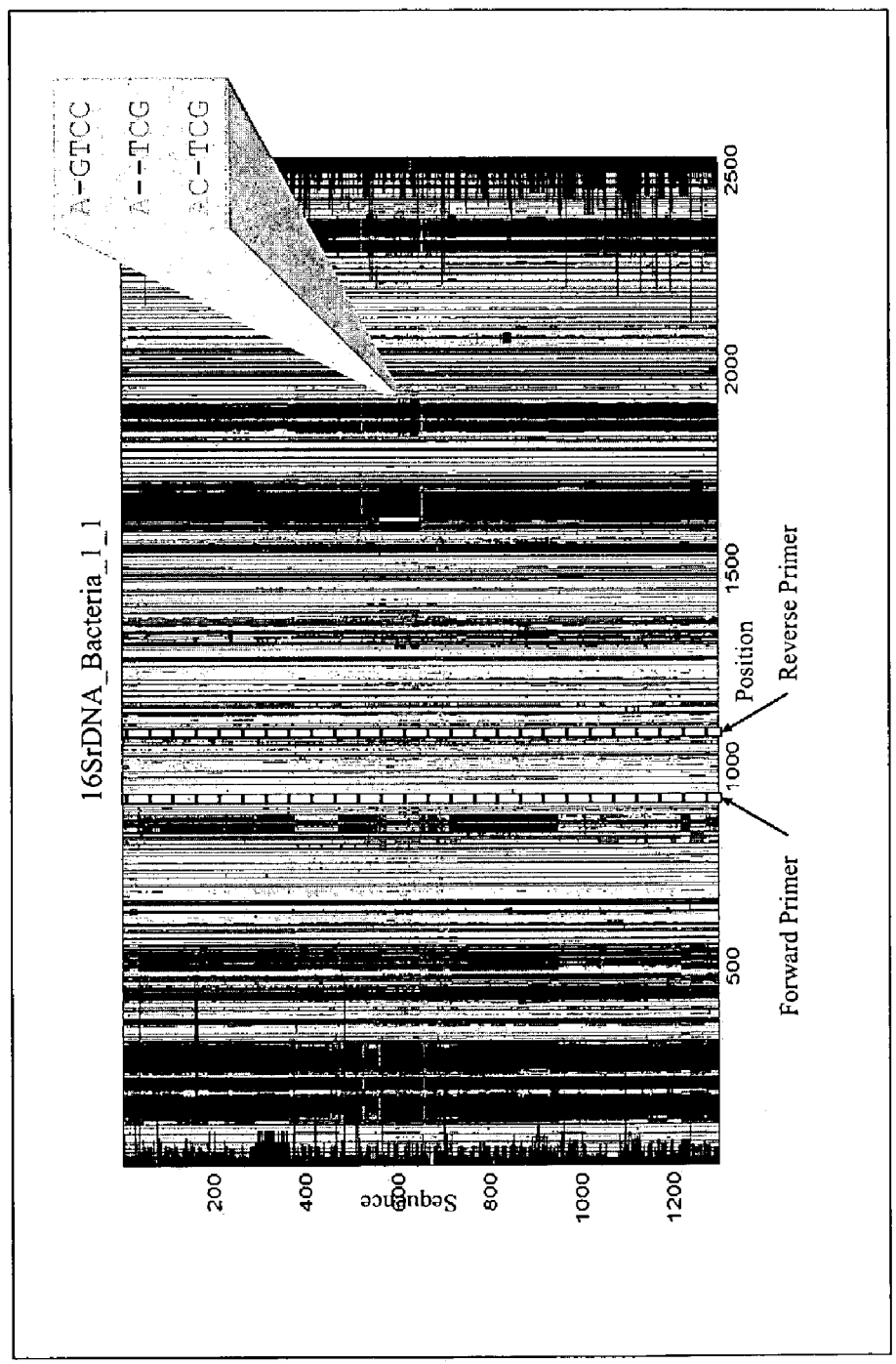
FIG. 3 shows an illustrative alignment of bacterial 16SrDNA sequences, showing forward and reverse primers bracketing a region to be amplified, in accordance with at least one aspect of the present invention.

FIG. 2 is a functional block diagram of one embodiment of a method for optimal selection of oligonucleotide primers for a situation in which an alignment of nucleotide sequences across species has first been constructed. In a very narrow and manual sense, such alignments can be generated for a single species, using algorithms and methods known in the art, such as BLAST (Basic Local Alignment Search Tool) (Altschul et al., J. Mol. Biol. 215, 403-10, 1990), Gapped BLAST (Basic Local Alignment Search Tool) (Altschul et al., Nucl. Acid Res. 25, 3389-402, 1997), and Clustal W/Multiple (Thompson et al., Nucl. Acids Res. 22, 4673-80, 1994). However, where the goal is the generation of primer pairs that differentiate each species from all other species, then non-linear algorithm is required. For example, FIG. 3 shows a typical alignment of bacterial 16S ribosomal sequences constructed using the Smith-Waterman algorithm. The vertical dimension of the alignment is the species or species variant, while the horizontal dimension indicates the position of each nucleotide within the aligned region for each particular species or species variant, as shown in the exploded portion of the figure. Dashes indicate gaps inserted into particular sequences to properly align common sequences of nucleotide bases.

Figure 4:
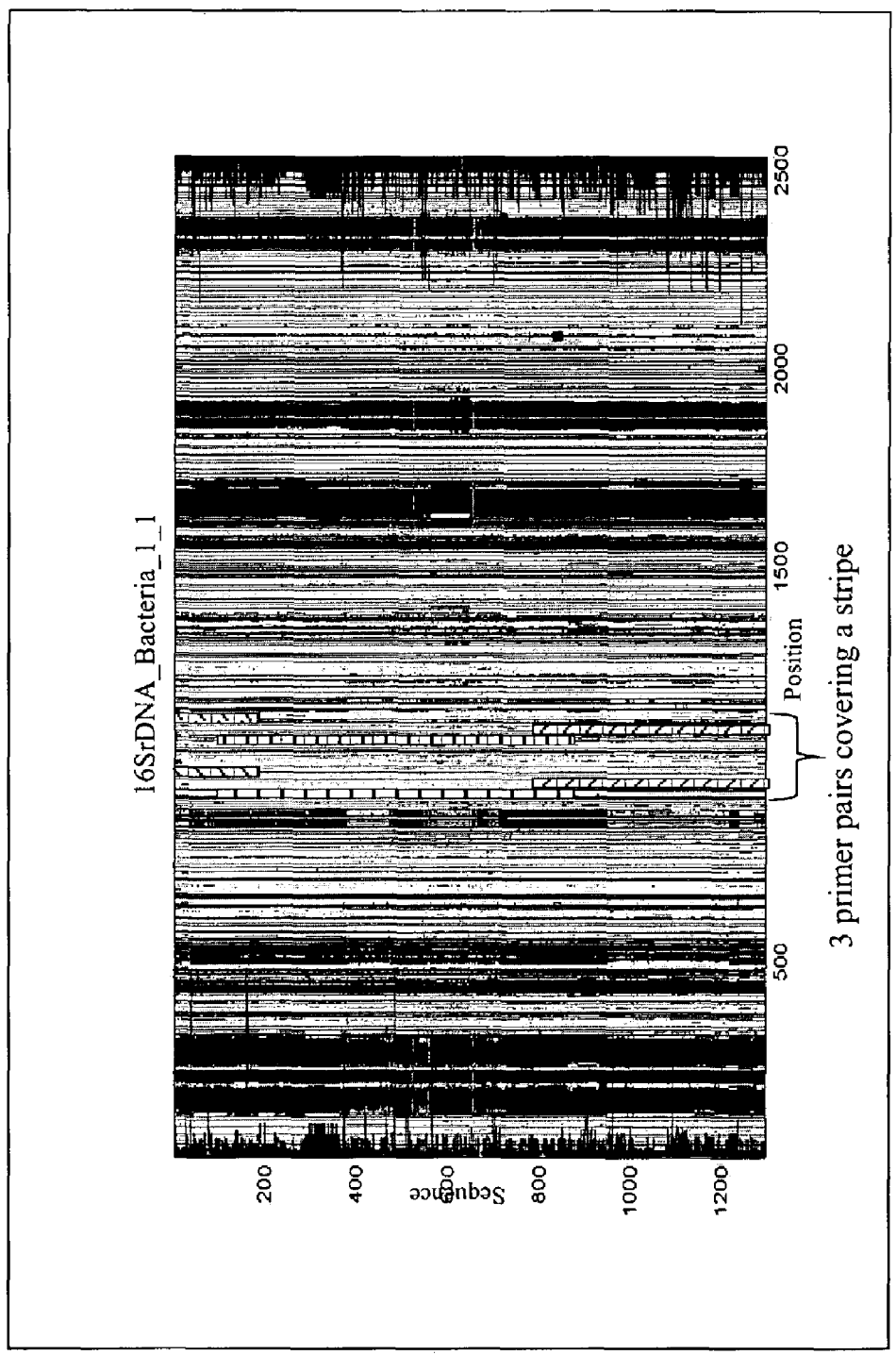
FIG. 4 shows an illustrative alignment of bacterial 16SrDNA sequences, showing three primer pairs bracketing a region to be amplified in accordance with at least one aspect of the present invention.
Figure 5:
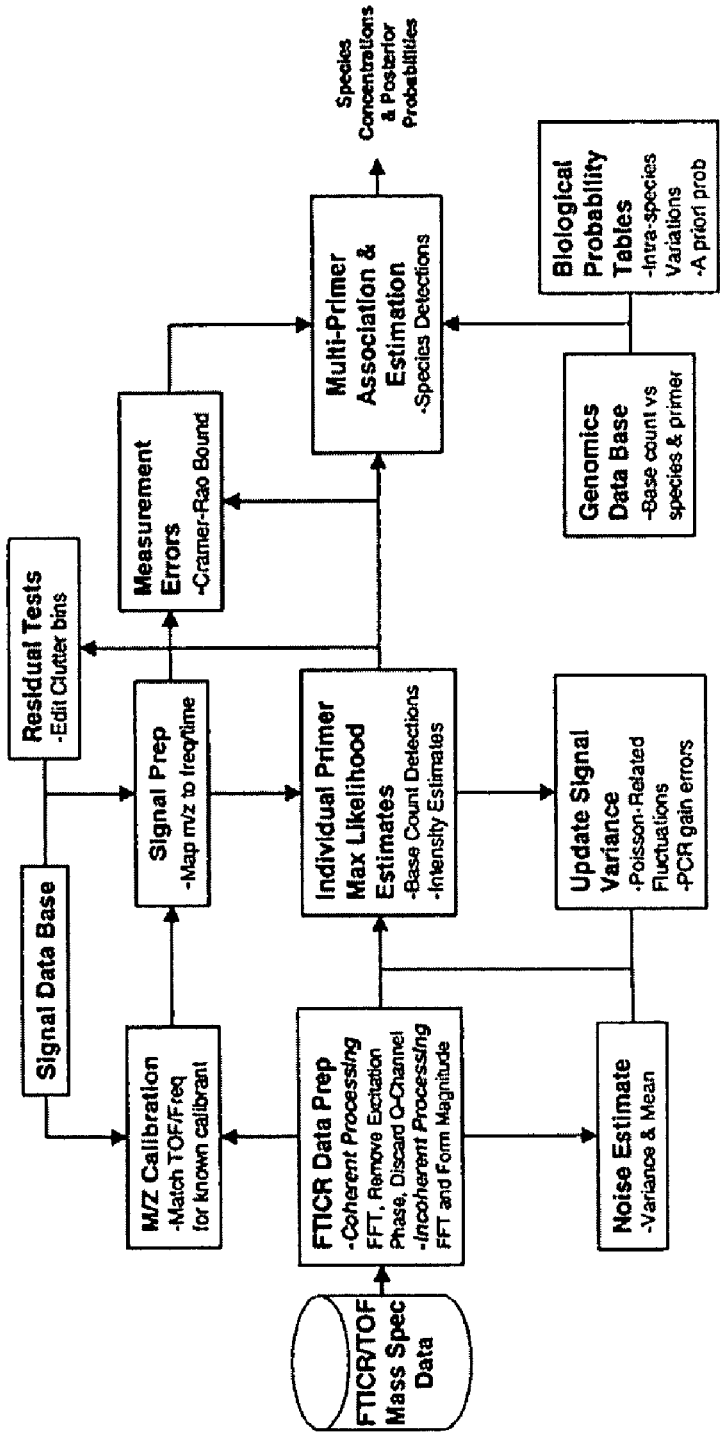
FIG. 5 is a functional block diagram of a Maximum-likelihood processor in accordance with at least one aspect of the present invention.

FIG. 3 shows possible positions of forward and reverse primers designed to amplify a region around nucleotide position 1000 in DNA sequences encoding bacterial 16S ribosomes. Detailed visual or computer inspection of the alignment can be carried out to determine whether a single primer pair will bind to and amplify all the species in the alignment or whether an additional pair or pairs of primers may be required, as shown in FIG. 4. Visual inspection is burdensome and time-consuming. Many different approaches for designing universal DNA primers have been proposed, although they are often computationally burdensome or are too limited in their primer selection criteria to be practical for the current application. See Tsunoda et al., "Time and Memory Efficient Algorithm for Extracting Palindromic and Repetitive Subsequences in Nucleic Acid Sequences,"; Evans & Wareham, "Practical Algorithms for Universal DNA Primer Design: An Exercise in Algorithm Engineering,". To circumvent these issues, the present invention provides a series of procedures and filters that can determine an initial primer set and identify those primers that will be most useful for identification of particular bioagents. The algorithm of the present invention employs the massive strength of computer algorithms to search biological sequence space for a distinguishing genotypic sequence for each biological member.

In one embodiment, only primer sequences that already exist within an alignment are considered as candidate primers. This set of candidate primers is screened against various primer performance criteria, and only those candidates that satisfy particular rules are retained. One or more filters can be used to assess these performance criteria. Filters that can be applied include primer filters, binding filters, and pairing filters. According to methods of the present invention, Each filter can be implemented by computer. A "primer design tool" can be constructed that incorporates one or more of the filters. A block diagram of one embodiment of a primer design tool is shown in FIG. 2.

Primer Filters

A primer filter can be used to identify a primer that forms a hybrid with its nucleotide reverse complement having a melting temperature ($T_m$) of between about 20° C. and about 60° C. Preferably, the melting temperature is between about 40° C. and about 60° C. Most preferred, the melting temperature is between about 50° C. and about 60° C. The $T_m$ of a hybrid can be calculated, for example, using the equation of Bolton and McCarthy, *Proc. Natl. Acad. Sci. U.S.A.* 48, 1390 (1962):

$$T_m=81.5°\ C.-16.6(\log_{10}[Na^+])+0.41(\%\ G+C)-0.63(\%\ \text{formamide})-600/l, \text{ where } l=\text{the length of the hybrid in basepairs.}$$

A primer filter also can be applied to identify primers with fewer than five GC repeats (i.e., 4, 3, 2, or 1 GC repeat) and/or primers that are between about 15 and about 25 bases or between about 18 and 23 bases in length (e.g., 13, 14, 15, 16, 17, 18, 19, 20, 21, 22, 23, 24, 25, 26, or 27 bases).

Primers that have a GC content of between about 30% and about 80% also can be identified using a primer filter.

Primers that are too likely to self-hybridize are undesirable. One example of "self-hybridization" is the formation of a dimer between one portion of a primer and another portion of an identical copy of the primer that has a complementary nucleotide sequence. Another example of self-hybridization is the formation of a "hairpin dimer," i.e., a dimer between one portion of a primer and another portion of the same primer that has a complementary nucleotide sequence.

A primer filter can be used to select primers that are not likely to self-hybridize. To determine the probability of self-hybridization, an AT bond is assigned a value of 2 and a GC bond is assigned a value of 4. The bond strength of a hairpin dimer preferably is less than 14. Similarly, the bond strength of a dimer formed between two identical primers is preferably less than 20. More preferably, the dimer bond strength is less than about 14.

The thresholds set by the primer filter are flexible and can be adjusted depending on how well an aligned genomic region is conserved. Preferred primers meet at least one of the five criteria described above. More preferred primers meet two, three, or four criteria. Most preferred primers meet all five criteria.

Binding Filters

The next step (step 202 of FIG. 2) in the primer selection process determines which of the remaining candidate primers will bind well to the target species. Because problems of specificity—i.e., a primer binding to more than one location within a sequence—are statistically unlikely due to the functionality of the gene, binding criteria are only applied to primer length sequences which are located at the same starting position within the alignment.

A binding filter can be applied to identify primers that hybridize with particular characteristics to at least one of the aligned nucleotide sequences. Preferably the binding filter is applied to a subset of primers which have met at least one, preferably two, three, or four, most preferably all five criteria selected for by the primer filter.

A binding filter can be set to identify, for example, primers that hybridize with a melting temperature of between about 20° C. and about 80° C. to at least one of the aligned nucleotide sequences. Melting temperature of between about 30° C. and about 70° C. are preferred with melting temperatures between about 40° C. and about 60° C. being most preferred. A binding filter also can be set to identify primers that hybridize to at least one of the aligned nucleotide sequences with no more than 2 mismatches and/or with no more than 2 mismatches in the last 4 base positions at the 3 end of the primer ("Hamming distance"). Preferably a primer hybridizes to an aligned nucleotide sequence with no mismatches. Primers to which the binding filter is applied preferably meet two and more preferably meet all three of these criteria. Application of the binding filter is repeated for every position within the alignment in both the forward and reverse direction yielding both a forward and reverse candidate primer set.

Pairing Filter

A pairing filter (step 203 of FIG. 2) preferably is applied to a subset of primers that have met one or more of the primer filter criteria and/or binding filter criteria described above. See FIG. 2. A pairing filter combines forward and reverse primers into pairs according to the following simple rules. First, bounds on the amplicon length are imposed. An upper bound of approximately 110 bases may be required due to the limitations of the mass spectrometer. A lower bound, which is slightly more than the sum of the lengths of the forward and reverse primer pairs, is also imposed to allow for enough variable region between the two primers to promote discrimination. Thus, a pairing filter identifies pairs of primers that can produce in an amplification (e.g., PCR) reaction an amplicon of between about 50 and about 150 nucleotides in length. Preferred amplicons are between about 50 and about 100 nucleotides in length.

A minimum number of sequences covered by the pair also can be set as a selection filter. Preferred primers hybridize to at least one of the species represented by the aligned sequences. More preferred primers hybridize to at least 2, 5, 10, or 25% of the aligned sequences. Most preferred primers hybridize to at least 50% of the aligned sequences. Lastly, primer-dimerization checks are performed on the forward and reverse primers using the same self-dimerization rules described above.

Application of a Greedy Algorithm to Rank and Choose Primer Pair Sets

An ideal primer pair covers every sequence within an alignment and produces amplicons that are variable enough to uniquely determine each species in the alignment. In practice, however, single primer pairs may not bind to and amplify all species in the alignment, and multiple primers may be required to amplify a particular genomic region from all species. For example, FIG. 3 shows possible positions of forward and reverse primers designed to amplify a region around nucleotide position 1000 in the alignment of bacterial 16SrDNA sequences.

One approach is to rank each candidate primer pair identified using filters described above according to coverage and then to apply a greedy algorithm to cover as many sequences with the fewest number of primer pairs possible. Thus, the primer pair that covers the greatest number of sequences is chosen first, the primer pair that covers the greatest number of the remaining sequences is chosen second, etc. It is preferred that all primer pairs lie in the same vicinity of each other such that they will amplify the same aligned region.

Figures 6A, 6B:
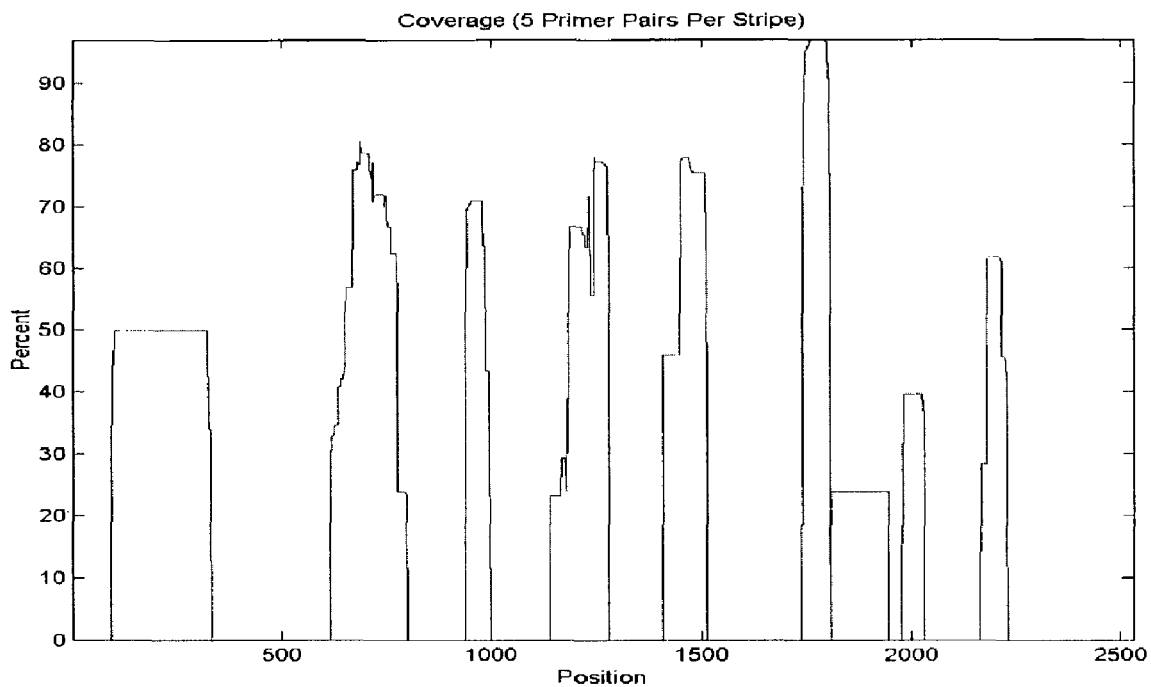
FIGS. 6A and 6B show illustrative results of an embodiment of an optimum primer selection process in accordance with at least one aspect of the present invention.

In one embodiment, a greedy algorithm is used to cover vertical "stripes" (i.e., regions of sequences that are conserved among at least 2 species in the alignment) within a set of aligned nucleotide sequences, such as the alignment shown in FIG. 4. Fixing the number of primer pairs per stripe, a coverage plot such as the plot shown in FIG. 6A for bacterial 16SrDNA is created for stripes. FIG. 6A shows the percentages of the species amplified by the best five primer pairs selected by a computer employing algorithms for the filters described above for each nucleotide position of the 16S unit of the ribosome. In this example, the selected primers achieve about 50% coverage in the region from nucleotide position 56 to position 376 and approach 100% coverage in the region near position 1750.

The right-most column in FIG. 6B shows the coverage predicted by human experts without the benefit of computer algorithms for applying the filters The superior performance of the computer algorithms is demonstrated by the fact that the computer algorithms identified all the regions thought likely to yield useful primers by the human experts and, in addition, found useful primers in six regions thought "unlikely" by the human experts. An additional advantage of the computer procedure is that it identified useful primer pairs in about an hour of running time on a personal computer, whereas the selection by the human experts involved several person-months of effort.

Figure 7:
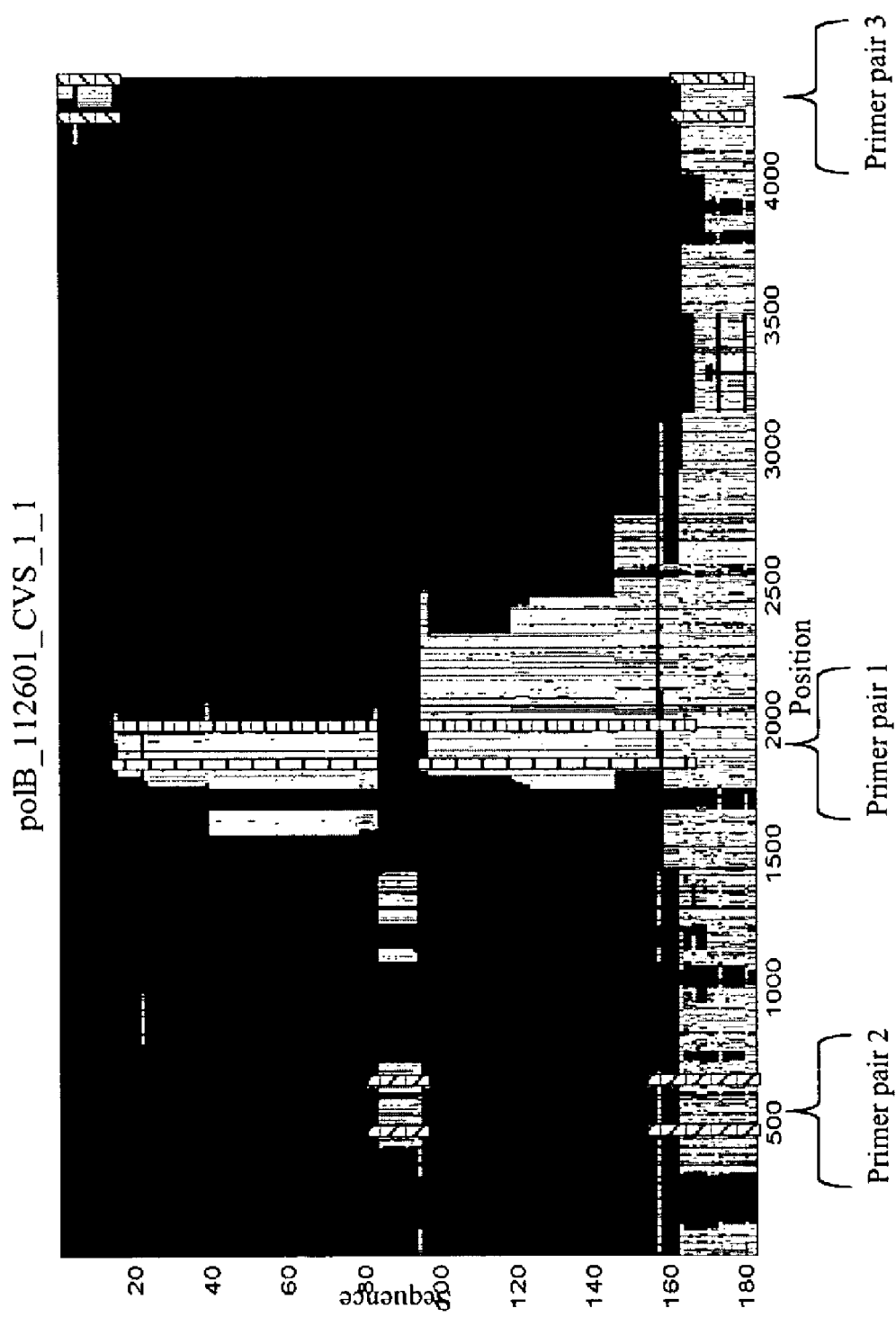
FIG. 7 illustrates illustrative results of a greedy approach to primer selection over an entire alignment in accordance with at least one aspect of the present invention.

In another embodiment, a "greedy approach" is used over the entire alignment, i.e., each consecutive primer pair is chosen anywhere within the alignment without regard to the location of the previously selected primer pairs. An example is shown in FIG. 7. Because some regions of bioagent genomes may not be well conserved, the greedy approach is less restrictive and will produce primer sets with greater coverage than the embodiment described above. For example, for the alignment shown in FIG. 7, coverage of only 50% was possible using the greedy approach over stripes, whereas the second approach was able to achieve over 70% coverage using an equal number of primer pairs.

The final step includes repeating the above procedure for other conserved loci, combining the primer pairs from these other regions using a greedy algorithm to identify primer pairs that will amplify nucleotide sequences of as many bioagents as possible with as few primer pairs as possible.

In one embodiment, primer sets can be selected using only a subset of the target sequences of interest. For example, alignments that identify primers for forty or fifty bacteria are likely to produce primer pairs that will amplify the desired regions of most of the other bacteria as well. However, this leads to the complication that all of the actual sequences are not available from which to predict mass spectroscopy signature models used in the maximum likelihood processor described below. To compensate for the lack of actual sequence data, actual mass spectroscopy measurements of amplicons from known bioagents can be used as templates. Alternatively, detection algorithms can be made robust to missing sequence data. For example, if only one amplicon of five is predictable, that amplicon is searched for and the others are treated like unknown clutter.

2. Procedure Without Prior Alignment of Sequences from Various Species

In principle, useful primer pairs can be found without first doing a multiple sequence alignment, by directly searching all possible sequence pairs and applying specificity and coverage criteria. In practice, however, this leads to extremely large computing burdens. As a useful compromise, faster, less-optimal multiple alignment procedures may be used to start the process. The alignment of a functional sequence region such as a conserved protein, for example, does not have to be perfect to support primer design. Rather, it merely has to align a region of the target sequences well enough that primer pairs can be found for that region. Simplified alignment procedures, such as nucleotide level BLAST (Basic Local Alignment Search Tool), can be used with one or more reference bioagents (e.g., E. coli for bacteria) as a "seed" for the local alignment of other bioagent sequences in a particular gene region. This method can assist in readily identifying regions that contain genes that are largely similar across a range of bioagent genomes.

Figure 8:
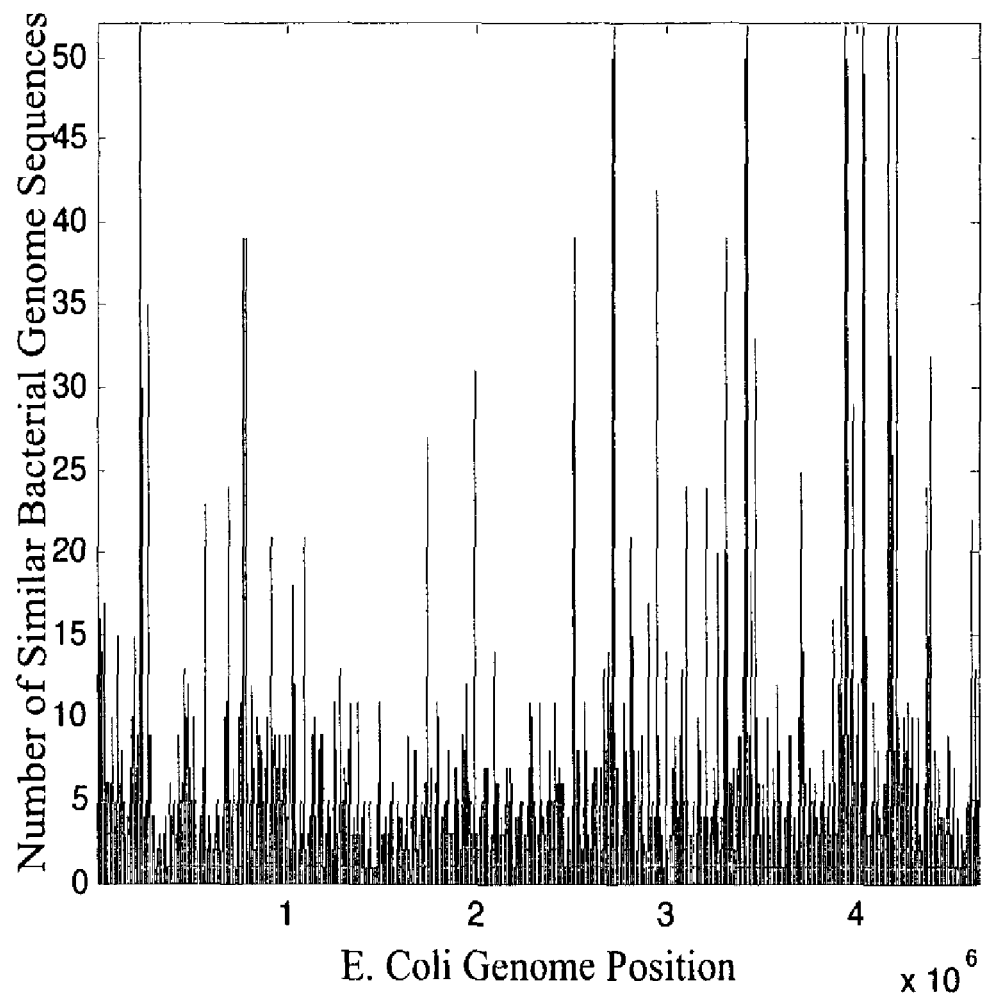
FIG. 8 shows a plot of the similarity of regions of *E. coli* K12 to other bacterial genomes.

An example of the results of using a simplified alignment procedure is shown in FIG. 8. In this example, the entire genome of E. coli K-12 is locally aligned to the set of all whole genome bacterial sequences available presently through GenBank (54 genomes total, including E. coli K-12). The genomes are aligned in a pairwise manner, and any regions of similarity greater than about 80% are retained. The number of bacterial genomes that contain regions similar to E. coli are tabulated, and this number is plotted as the y-axis versus the E. coli genomic position on the x-axis.

Figure 10:
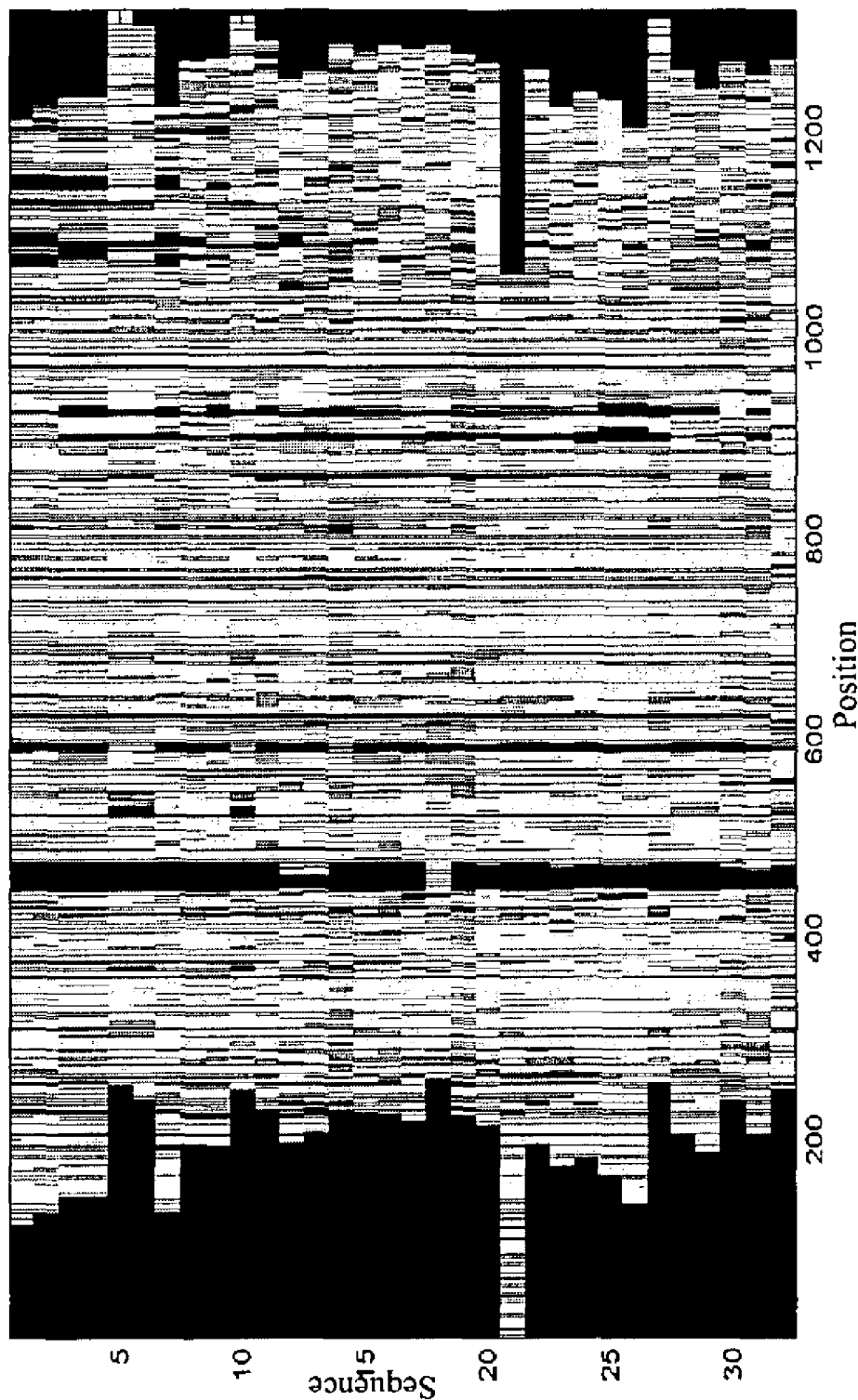
FIG. 10 shows an illustrative tufA protein alignment from 32 genomes in accordance with at least one aspect of the present invention.
Figure 11:
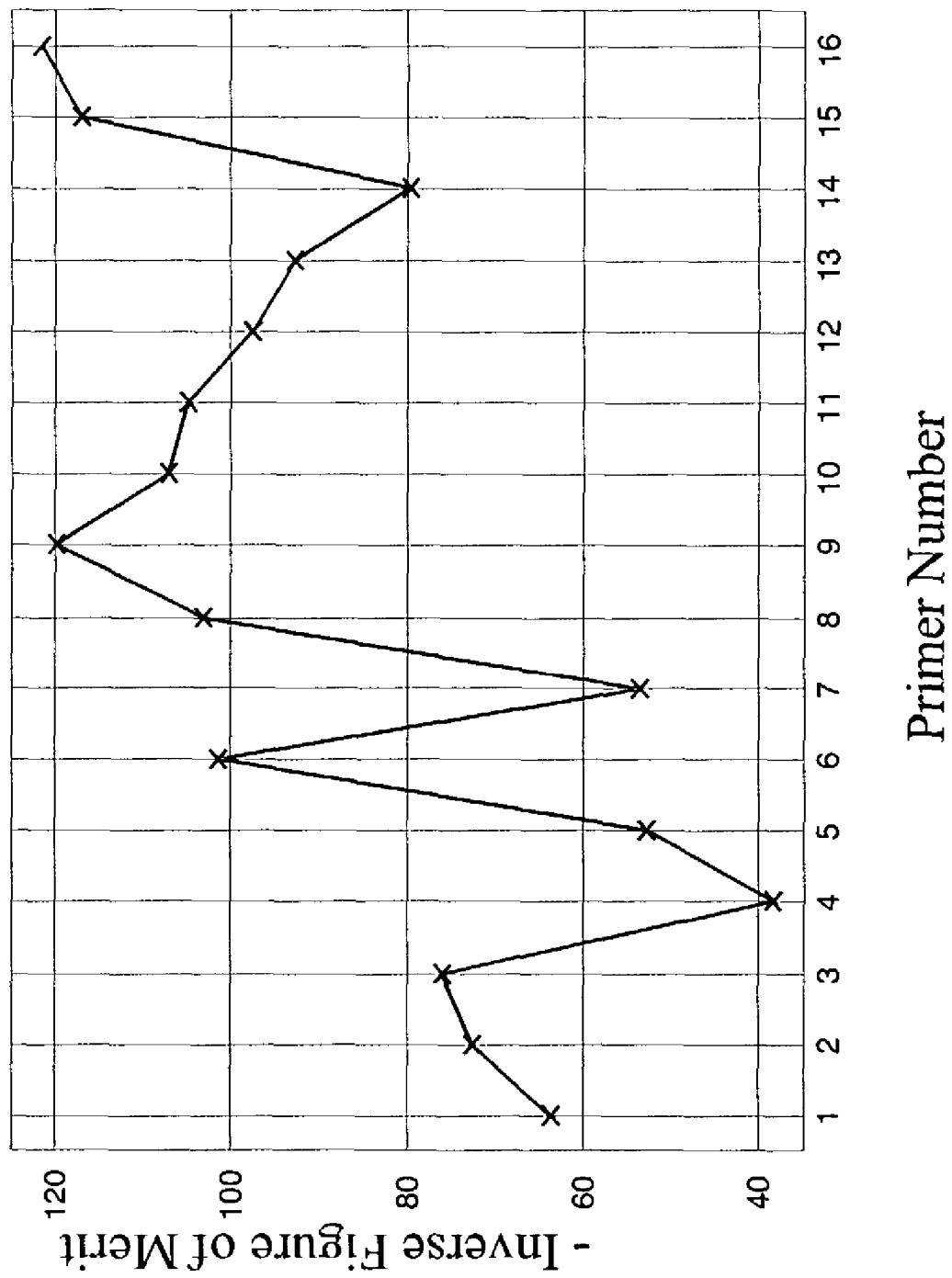
FIG. 11 is a graph showing illustrative discrimination ranking for a master list of 16 individual primer sets, in accordance with at least one aspect of the present invention.
Figure 12:
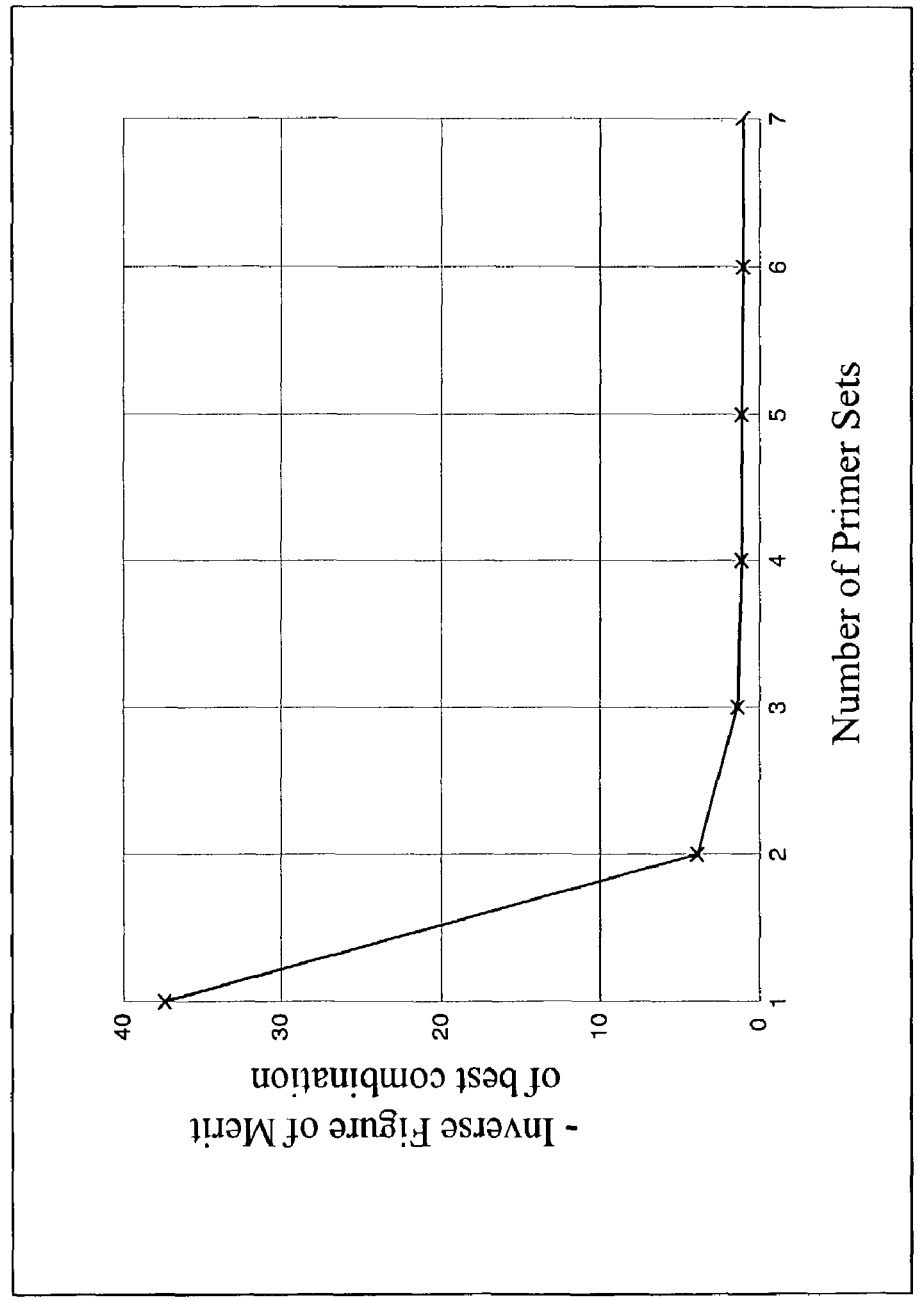
FIG. 12 is a graph showing illustrative discrimination ranking of combinations of primer sets from a master list of 16 primer sets.

The peaks in the similarity plot indicate specific locations where the E. coli region is similar to a locally maximum number of other bacterial regions. This inclusive set of similarity regions are collected and multiply aligned. The regions align quickly and easily due to the similarity criteria in the initial step. Once the sequences are collected, a gene that resides in the aligned region can be identified by its location on the E. coli genome. FIG. 9 shows a subset of the peaks for E. coli and their respective identifications. A representative resulting alignment, which enables the primer pair selection as previously described, is shown in FIG. 10.

Ranking Primer Choices by Discrimination Metrics

Once a master list of primers sets have been selected and primer pair sets have been ranked and chosen, additional ranking methods can be used to choose the best primers for a particular purpose. Identification methods of the invention measure the mass and, hence, identify the base counts of amplicons in a sample. Thus, optimal primer sets for use in these methods would effectively separate the base counts of all of the amplicons from different species of bioagents (e.g., different bacterial, viral, or fungal species) into unique groups. If this accomplishment were perfectly achieved, it would enable a detected base count to be classified unambiguously as belonging to a unique bioagent. In many cases, however, unambiguous separation of species by base count group is not biologically possible. It is, therefore, useful to use a "discrimination metric" to predict how well a particular primer set accomplishes the task of discriminating species. The discrimination metric ranks primer sets in an order that directly relates to the discrimination power of each of the primer sets.

To properly define the ranking criteria, the region in the four-dimensional "base count space" (A-G-C-T) occupied by all members of a particular bioagent group is first defined. This region is partially defined by collection of all of the strain sequence data for each species that would be amplified by each primer set (hypothetical PCR reactions, for example—"electronic PCR"—can be used to collect this data, as described below). Biologically likely species variants that may not be in the sequence database, however, must be taken into account. This can be accomplished, for example, using a "cloud algorithm."

For unambiguous detection and identification of bioagents, it would be ideal if every isolate of a given species of bioagent (E. coli, for example) had exactly the same base count in any particular amplified region. However, due to naturally occurring mutations and/or deliberately engineered changes, isolates of any species might have some variation in the base count of a particular region. Because of naturally occurring variation and because engineered threat bioagents may differ slightly in particular regions from their naturally occurring counterparts, it is useful to "blur" the expected base count for a given species to allow for this variation so that the system does not miss detections. The more the expected base count is blurred, the less likely it is that a particular species will escape detection; however, such blurring will cause more overlap between the expected base counts of different species, contributing to misclassifications.

To solve this problem, expected base counts can be blurred according to the natural principles of biological mutations, customizing the specific blurring to the biological constraints of each amplified region. Each amplified region of a particular bioagent is constrained in some fashion by its biological purpose (i.e., RNA structure, protein coding, etc.). For example, protein coding regions are constrained by amino acid coding considerations, whereas a ribosome is mostly constrained by base pairing in stems and sequence constraints in unpaired loop regions. Moreover, different regions of the ribosome might have significant preferences that differ from each other.

One embodiment of application of the cloud algorithm is described in Example 1.

By collecting all likely species amplicons from a primer set and enlarging the set to include all biologically likely variant amplicons using the cloud algorithm, a suitable cluster region of base count space is defined for a particular species of bioagent. The regions of base count space in which groups of related species are clustered are referred to as "bioclusters."

When a biocluster is constructed, every base count in the biocluster region is assigned a percentage probability that a species variant will occur at that base count. To form a probability density distribution of the species over the biocluster region, the entire biocluster probability values are normalized to one. Thus, if a particular species is present in a sample, the probability of the species biocluster integrated over all of base count space is equal to one.

At this point in the ranking procedure, proposed target species to be detected are taken into account. These generally are the bioagents that are of primary importance in a particular detection scenario. For example, if *Yersinia pestis* (the causative agent of bubonic and pneumonic plague) were the target, the *Yersinia pestis* species biocluster identified as described above, would be the "target biocluster." To complete the example, assume that all other database species serve as the scenario background. The discrimination metric in this case is defined as the sum total of all the biocluster overlap from other species into the *Yersinia pestis* biocluster.

In this example, the *Yersinia pestis* biocluster overlap is calculated as follows. A probability of detection of 99% ($P_D$=0.99) is defined, although this value can be altered as needed. The "detection range" is defined as the set of biocluster base counts, of minimal number, that encloses 99% of the entire target biocluster. For each other bacterial species in the database, the amount of biocluster probability density that resides in the base counts in the defined detection range is calculated and is the effective biocluster overlap between that background species and the target species. The sum of the biocluster overlap over all background species serves as the metric for measuring the discrimination ability of a defined target by a proposed primer set. Mathematically, because the most discriminating primer sets will have minimal biocluster overlap, an inverse figure of merit $\Phi$ is defined, $$\Phi = \sum_{\substack{i=all \\ bioclusters}} \theta_i$$

where the sum is taken over the individual biocluster overlap values $\theta_i$ from all N background species bioclusters (i=1, . . . , N). For example, FIG. 11 shows the inverse figure of merit $\Phi$ plotted for a master list of 16 primer sets using *Yersinia pestis* as the target biocluster. Using the inverse figure of merit minimization criteria defined above, the result is that primer set number 4 provides the best discrimination of any of the individual primer sets in the master list.

This set of discrimination criteria also can be applied to combinations of primer sets. The respective four-dimensional base count spaces from each primer set can be dimensionally concatenated to form a (4×N)-dimensional base count space for N primer sets. Nowhere in the biocluster definition is it necessary that the biocluster reside in a four-dimensional space, thus the biocluster analysis seamlessly adapts to any arbitrary dimensionality. As a result, a master list of primer sets can be searched and ranked according to the discrimination of any combination of primer sets with any arbitrary number of primer sets making up the combination.

Using again the example of *Yersinia pestis* as the target, FIG. 12 shows the improved discrimination achieved through use of an increasing number of primers. For each number of primers value on the x-axis, the plotted inverse figure of merit value is that obtained from the most discriminating group (that group with the minimum figure of merit for that number of primer sets simultaneously used for discrimination). The result is that after the best groups of 3 and 4 primer sets are found, the inverse figure of merit approaches one and goes no further. That means that there is the equivalent of one background species biocluster overlapping into the target biocluster. In this example it is the *Yersinia pseudotuberculosis* species biocluster, which cannot be discriminated from *Yersinia pestis* by any combination of the 16 primer sets in the example. Thus, using the "best" 3 or 4 primer sets in the master list, *Yersinia pestis* is essentially discriminated from all other species bioclusters.

Generation of Amplicons

Primers selected above are used to amplify variable regions from bioagent nucleic acids in a test sample to produce double-stranded DNA amplicons. A test sample that may contain bioagents to be identified can be obtained from the air outside or inside a building, from human clinical samples (e.g., throat or nasal swabs, blood, or urine samples), food samples, swipes from clothing or furniture, or from any other source suspected of being contaminated with a biological warfare agent or a human pathogen.

The test sample is prepared for analysis by releasing nucleic acids (either DNA or RNA) from bioagents within the sample according to methods known in the art, including bead-beating and chemical lyses. However, the skilled artisan will forsee, perhaps, advantages to other methods for extracting the needed material. The preparation of the sample is outside the scope of the present claims but the skilled artisan will understand numerous way of accomplishing the desired extraction. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.).

Any amplification method can be used to produce the amplicons, such as polymerase chain reaction (PCR), ligase chain reaction (LCR), and strand displacement amplification (SDA). Methods of carrying out such amplification reactions are well known in the art.

PCR is preferred and can be carried out as described, for example, in Muddiman et al., *Anal. Chem.* 68, 3705, 1996, and Muddiman et al., *Anal. Chem.* 69, 1543-49, 1997.

Processing of Amplicons for Injection into a Mass Spectrometer Amplicons from each of the amplification reactions is further processed to remove contaminants in preparation for analysis in the mass spectrum. See Muddiman et al., *Anal. Chem.* 68, 3705, 1996.

Generation of Base Counts from Mass Spectra of Double-Stranded DNA Amplicons

The base counts of amplicons obtained from a test sample are identified using mass measurements from mass spectrometry. Algorithms for obtaining accurate base counts of double-stranded DNA are described, for example, in Aaserud et al., *Amer. Soc. Mass Spectrom.* 7, 1266-69, 1996, and Muddiman et al., *Anal. Chem.* 69, 1543-49, 1997. Determination of monoisotopic masses and ion populations are described in Senko et al., *Amer. Soc. Mass Spectrom.* 6, 229-33, 1995.

Any type of mass spectrometer, such as a high resolution Fourier transform ion cylcotron resonance (FTICR) mass spectrometer or time-of-flight (TOF) mass spectrometer, can be used to obtain the mass measurements. Preferably, a mass spectrometer can provide high-precision mass measurements on the order of less than 1 ppm. See Winger et al., *J. Am. Soc. Mass Spectrom.* 4, 566, 1993.

A preferred FTICR mass spectrometer uses a 7 teals actively shielded super conducting magnet and modified Broker Atonics Apex II 70e ion optics and vacuum chamber. The spectrometer is interfaced to a LEAP PAL auto sampler and a custom fluidics control system for high throughput screening applications. Samples are analyzed directly from 96-well or 384-well microtiter plates at a rate of about 1 sample/minute. The Broker data-acquisition platform is supplemented with a lab-built ancillary NT data station which controls the auto sampler and contains an arbitrary waveform generator capable of generating complex rFC-excite waveforms (frequency sweeps, filtered noise, stored waveform inverse Fourier transform (SWIFT), etc.) for sophisticated tandem MS experiments. For oligonucleotides in the 20-30-mer regime typical performance characteristics include mass resolving power in excess of 100,000 (FWIM), low ppm mass measurement errors, and an operable m/z range between 50 and 5000 m/z.

A 25 watt CW $CO_2$ laser operating at 10.6 mm can be interfaced to the spectrometer to enable infrared multipotent dissociation (IRMPD) for oligonucleotide sequencing and other tandem MS applications. An aluminum optical bench is positioned approximately 1.5 m from the actively shielded super conducting magnet such that the laser beam is aligned with the central axis of the magnet. Using standard IR-compatible mirrors and kinematics mirror mounts, the unfocused 3 mm laser beam is aligned to traverse directly through the 3.5 mm holes in the trapping electrodes of the FTICR trapped ion cell and longitudinally traverse the hex pole region of the external ion guide finally impinging on the skimmer cone. This scheme allows IRMPD to be conducted in an m/z selective manner in the trapped ion cell (e.g., following a SWIFT isolation of the species of interest), or in a broadband mode in the high pressure region of the external ion reservoir where collisions with neutral molecules stabilize IRMPD-generated detestable fragment ions resulting in increased fragment ion yield and sequence coverage.

A TOF mass spectrometer also can be used to obtain mass spectra of amplicons. A TOF mass spectrometer measures the population of ions that arrive within a sequence of time intervals. The output digitized data from a TOF mass spectrometer differs in character from that from an FTICR mass spectrometer in that TOF data are inherently incoherent and TOF resolution is relatively coarse. The only step that is required to prepare data from a TOF mass spectrometer for maximum-likelihood processing is a time-of-flight calibration. This is obtained by measuring the arrival times for the various charge states of a known calibrant molecule.

Injection of the Sample into the Mass Spectrometer

Intact molecular ions can be generated from amplification products using one of a variety of ionization techniques to convert the sample to gas phase. These ionization methods include, but are not limited to, electro spray ionization (ESI), matrix-assisted laser resorption ionization (MALDI) and fast atom bombardment (FAB). For example, MALDI of nucleic acids, along with examples of matrices for use in MALDI of nucleic acids, are described in WO 98/54751 (Gene trace, Inc.).

The sample preferably is injected into the mass spectrometer using electro spray ionization (ESI). ESI is a gentle ionization method that produces several multiply charged ions of the parent nucleic acid without any significant fragmentation. Typically, a single charge state of the nucleic acid is isolated using a triple quadruple ion trap or ion cyclotron resonance (ICR) device. This ion is then excited and allowed to collide with a neutral gas (e.g., helium, argon, or nitrogen) to cleave certain bonds in the nucleic acid ion, or excited and fragmented with a laser pulse. Details of such techniques are well known in the art. See, e.g., U.S. Pat. Nos. 6,428,956, 5,015,845, 5,504,327, 5,504,329, 5,608,217, and 5,828,062.

Preferably, solutions to be analyzed are delivered at 150 nil/minute to a 30 mm i.d. fused-silica ESI emitter mounted on a 3-D micromanipulator. The ESI ion optics consist of a heated metal capillary, an only-only hex pole, a skimmer cone, and an auxiliary gate electrode. The 6.2 cm only-only hex pole is comprised of 1 mm diameter rods and is operated at a voltage of 380 Pv at a frequency of 5 MHz. A lab-built electro-mechanical shutter can be employed to prevent the electro spray plume from entering the inlet capillary unless triggered to the "open" position via a TTL pulse from the data station. When in the "closed" position, a stable electro spray plume is maintained between the ESI emitter and the face of the shutter. The back face of the shutter arm contains an electrometric seal which can be positioned to form a vacuum seal with the inlet capillary. When the seal is removed, a 1 mm gap between the shutter blade and the capillary inlet allows constant pressure in the external ion reservoir regardless of whether the shutter is in the open or closed position. When the shutter is triggered, a "time slice" of ions is allowed to enter the inlet capillary and is subsequently accumulated in the external ion reservoir. The rapid response time of the ion shutter (<25 ms) provides reproducible, user defined intervals during which ions can be injected into and accumulated in the external ion reservoir.

The output of the mass spectrometer is a time series of relative intensities. These data are then transformed/calibrated to allow determination of the number of molecules at each mass/charge (m/z) value. The transformed/calibrated digital mass spectrometer output is then passed to a maximum likelihood processor, which is described below. The maximum likelihood processor then makes a maximum-likelihood estimate of the number of DNA molecules of each species that were injected into the mass spectrometer. The maximum-likelihood processor ultimately carries the quantitative calibration back to a concentration estimate in the original sample.

Maximum Likelihood Processing of Amplicon Mass Spectra

Figure 13:
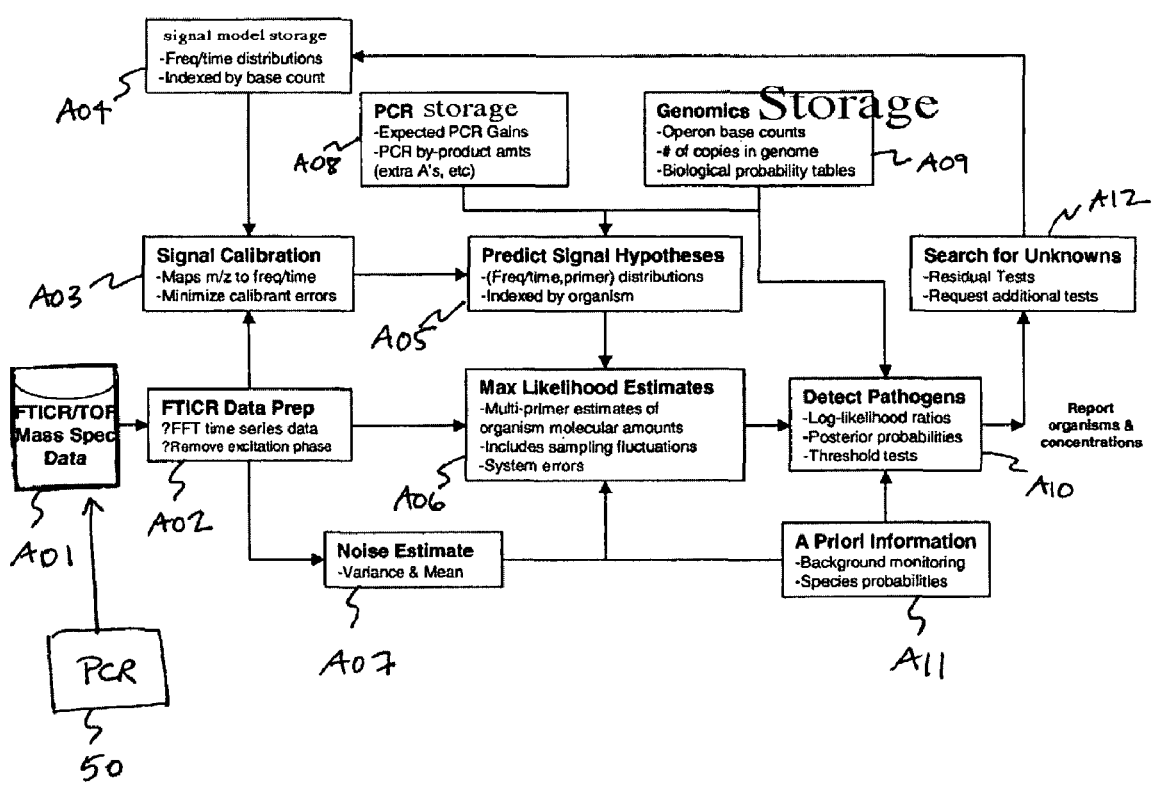
FIG. 13 is a functional block diagram of an illustrative embodiment of a genetic evaluation system in accordance with at least one aspect of the present invention.

Referring to FIG. 13, once PCR primer pairs have been selected as described herein, the biological entities such as bacterial or viral bioagents present in a sample may be evaluated and ultimately identified by analyzing the mass spectra of the amplicons produced by the primer pairs. As described above the mass spectra may be measured by a device such as a mass spectrometer or the like, in response to a chirp or other excitation signal applied to the amplicons. The mass spectrometer may be any type of mass spectrometer, including, but not limited to, a Fourier transform ion cylcotron resonance (FTICR) mass spectrometer or a time-of-flight (TOF) mass spectrometer.

The mass spectrometer may output mass spectra data representing some or all of the mass spectra. For example, the mass spectra data may be in the form of data representing one or more digitized time series of amplitude signals. The amplitude may represent, e.g., concentration. The mass spectra data may represent the mass spectra in any domain such as the time domain, the frequency domain, or the mass/charge (m/z) domain. The mass spectra data may be preliminarily processed in any of a number of ways (FTICR Data Prep A02). For instance, the Fourier transform may be taken of the mass spectra data (such as by fast-Fourier transform, or FFT), with appropriate weighting for side lobe control to form the coherent frequency response of the excited ions.

If the effects due to both ion-neutral collisions and non-linear interactions between charged ions are negligible, then the phase of this complex-valued response may be determined by the phase of the excitation waveform. This phase, which may be described by a second-order polynomial, may be estimated using the strongest observed spectral lines and removed from the data.

Figure 14:
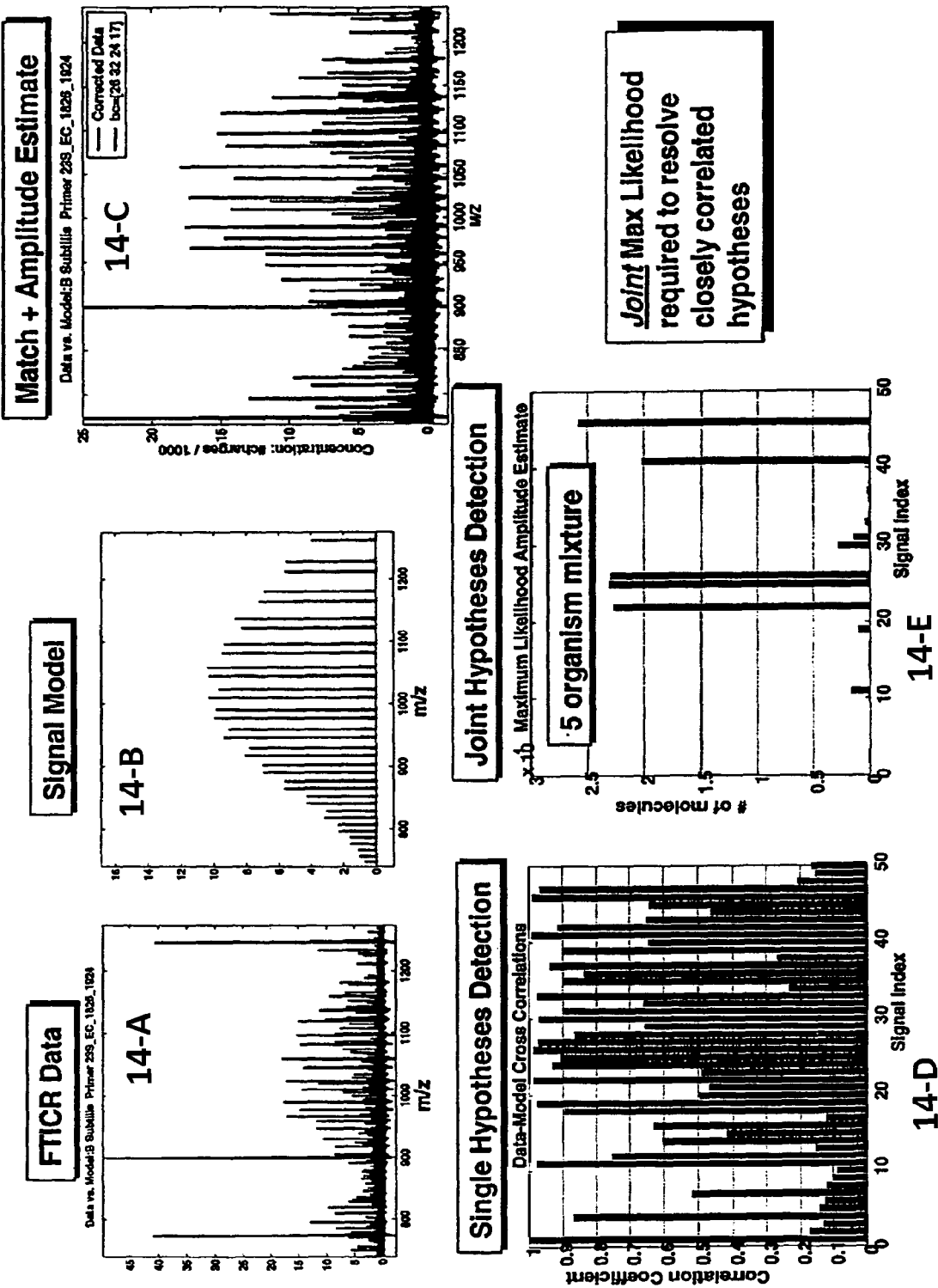
FIG. 14 is a graph showing illustrative data that may be obtained from a mass spectrometer in accordance with at least one aspect of the present invention.
Figure 16:
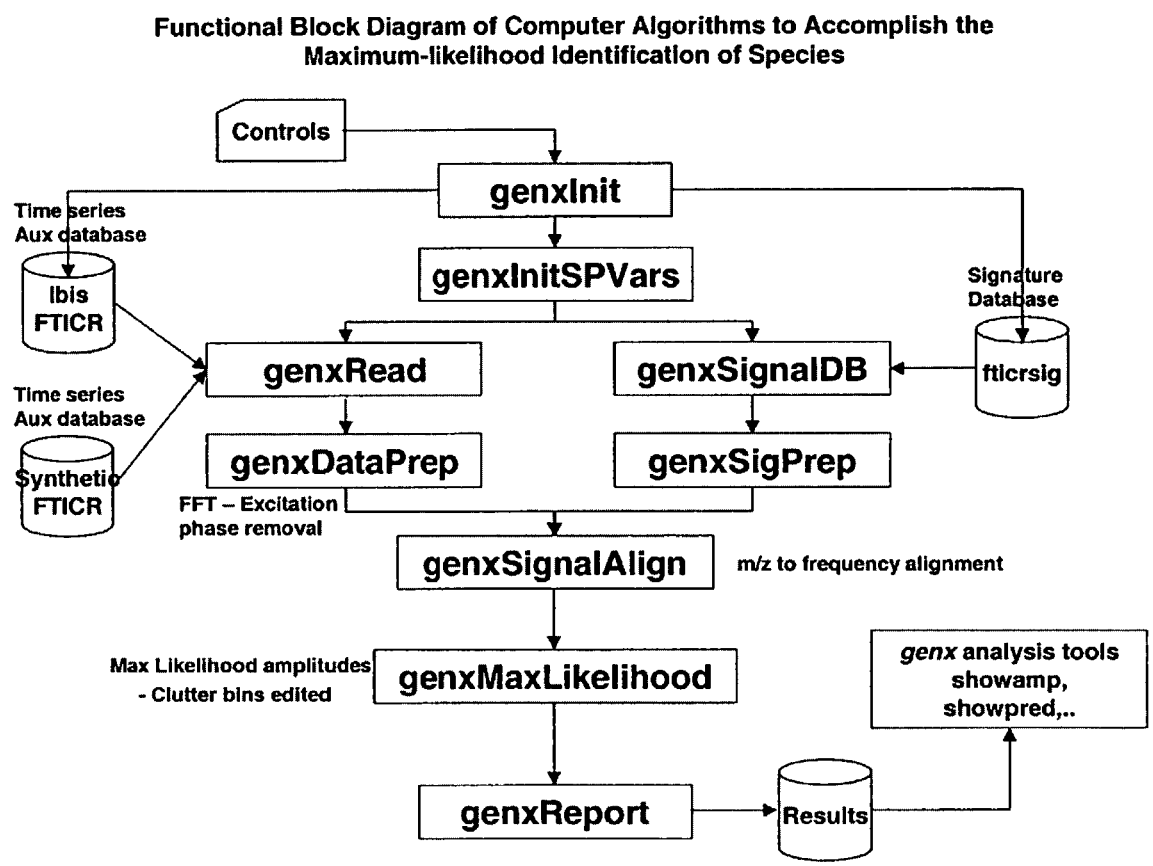
FIG. 16 is a functional block diagram of a non-linear/computer based algorithmic logic map to accomplish an illustrative maximum-likelihood identification of species scheme.
Figure 17:
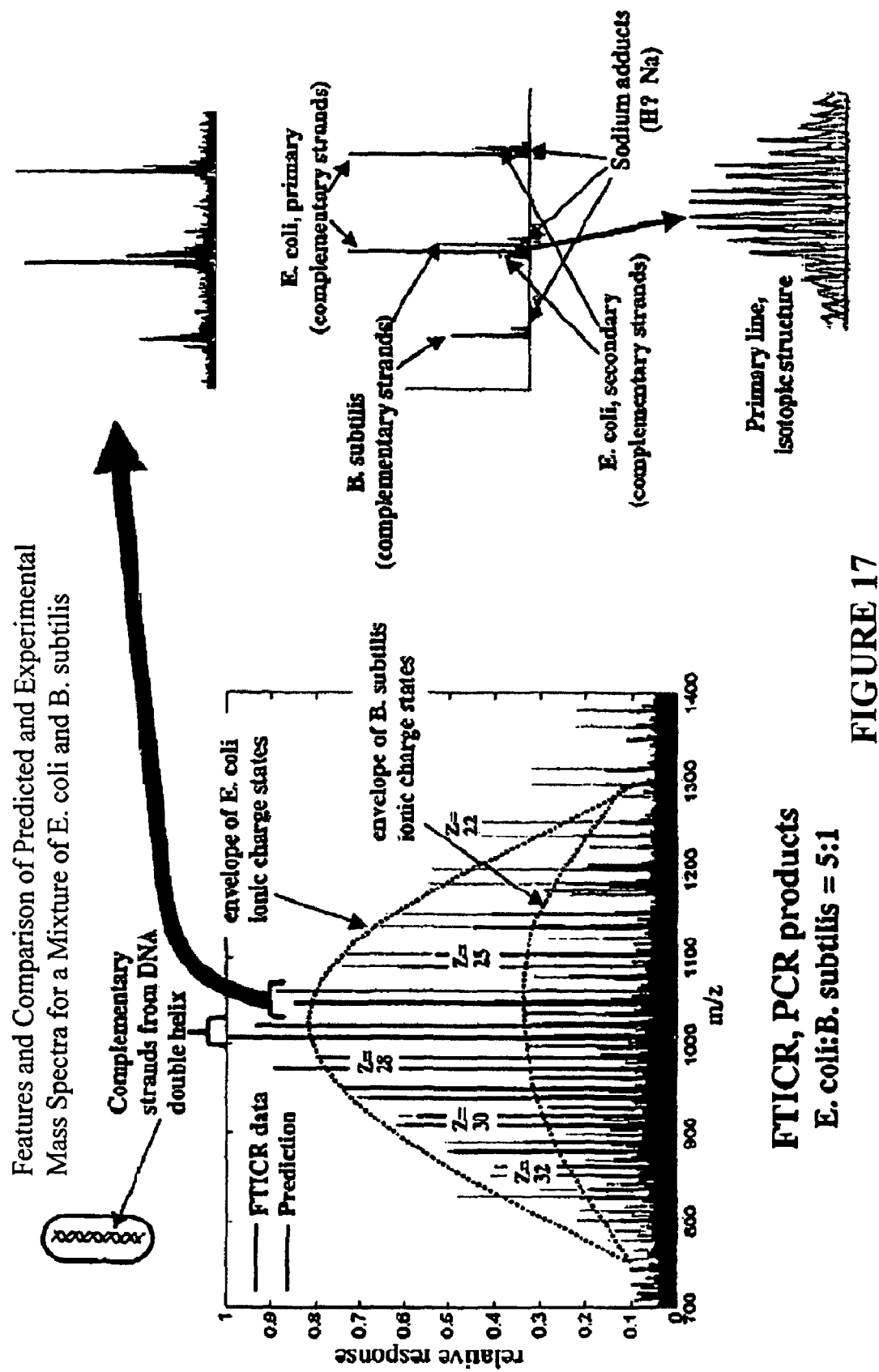
FIG. 17 is an illustrative comparison of predicted and experimental mass spectra for a mixture of bio-agents in accordance with at least one aspect of the invention.
Figure 18:
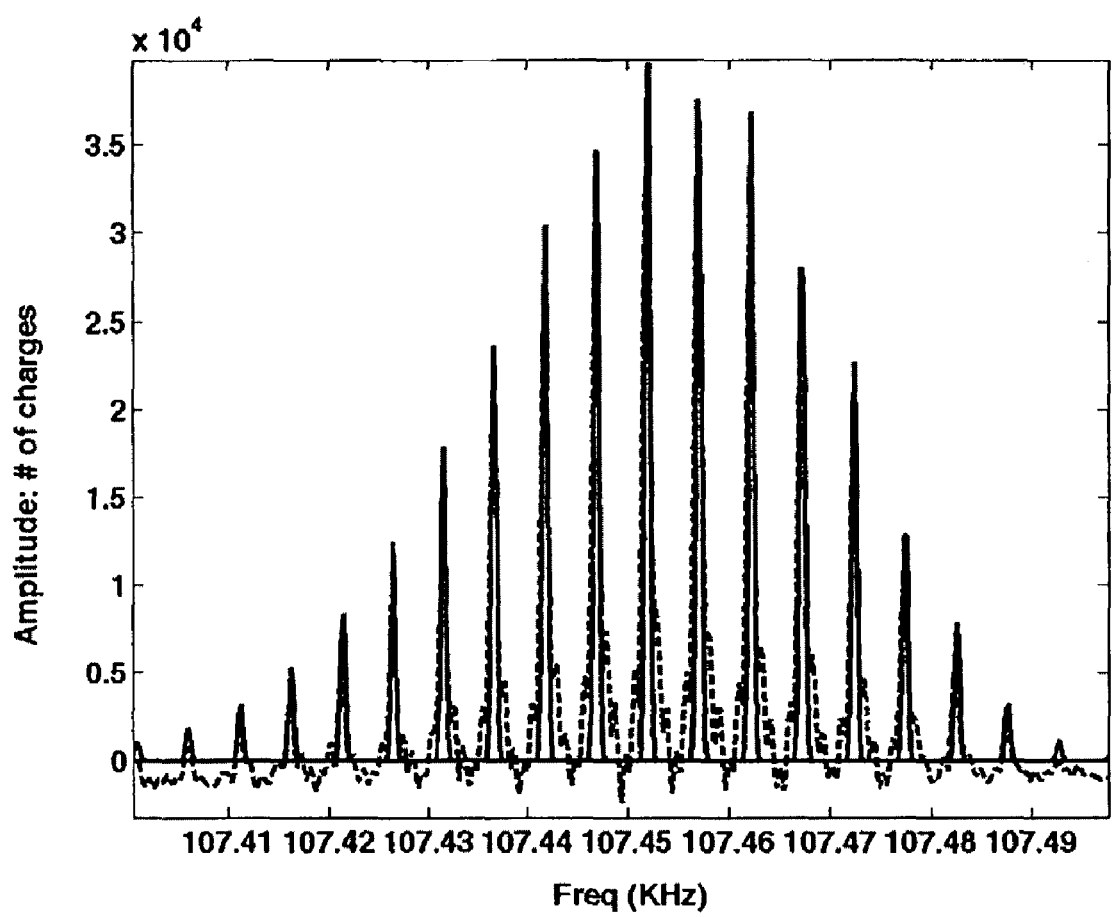
FIG. 18 is an illustrative comparison of predicted and observed isotopic lines in a mass spectrum.
Figure 19:
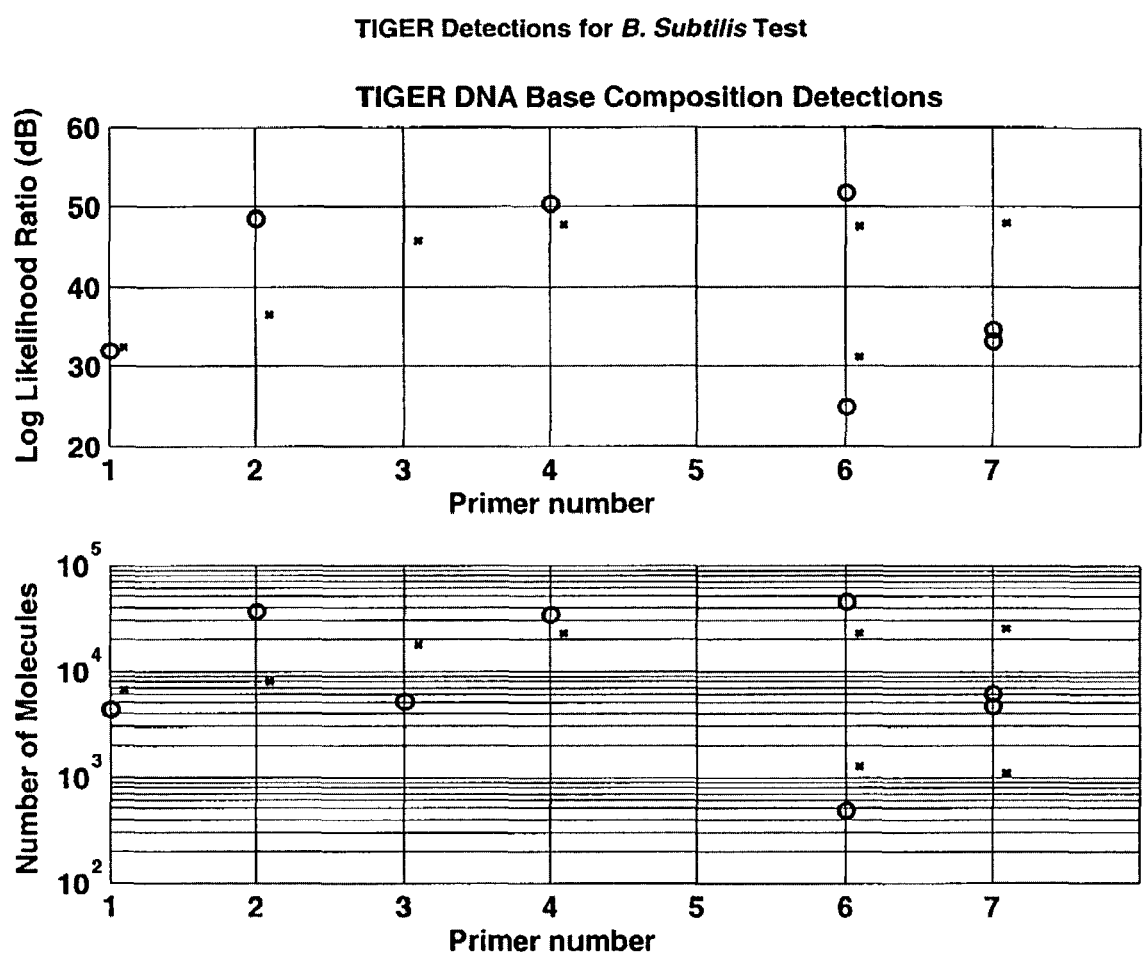
FIG. 19 is an illustrative, graphical representation of detection schemes according to one aspect of the invention.

Once the excitation phase is removed, the data can be expected to be essentially real-valued and positive-definite (except perhaps for frequency sidelobe). An example of such processed mass spectra data for the amplicon produced from *B. subtilis* and a primer pair "23_EC__1826__1924" is shown in FIG. 14-C.

The genetic evaluation system may include one or more storage devices, called herein signal model storage A04, for storing one or more signal models. An example of a signal model is shown in FIG. 14-B. The signal models may each be an estimation or other hypothesis of mass spectra for a particular hypothesized amplicon. The signal models may be in any units desired, and may have an amplitude of, e.g., concentration of units of discrete charge, and may be in the frequency or m/z domain. Some or all of the signal models may further be based on prior actual mass spectra measurements of amplicons.

The signal model storage A04 may be any storage device or collection of storage devices (such as one or more hard drives, memories, disk drives, tape drives, and the like) and may be configured as a database. The signal model storage A04 may be continuously updated as more information about mass spectra for various amplicons becomes known.

The signal model storage A04 may further associate each of the signal models with one or more of a plurality of base counts or mass distributions, and/or associate each of a plurality of base counts or mass distributions with one or more signal models. Such association may be direct or indirect, e.g., within a same database or between a plurality of cross-indexed databases. For example, a hypothesized amplicon may contain 26 adenine, 32 guanine, 24 cytosine, and 17 thymidine nucleotides. The base count for such an amplicon may be expressed herein as [26 32 24 17], or alternatively as $A_{26}G_{32}C_{24}T_{17}$. In the signal model storage A04, the base count(s) associated with each of the signal models may be those base counts of hypothesized amplicons that are expected to produce those signal models from a mass spectrometer. Thus, for example, base count [26 32 24 17] may be associated in the signal model storage A04 with one or more signal models that are predicted to be produced by a mass spectrometer were an amplicon with that base count measured by the mass spectrometer.

In one illustrative embodiment, the signal model storage A04 may store tens of thousands of different signal models and/or base counts, however any amount may be used. In an alternative illustrative embodiment, one or more of the signal models may be generated as needed in order to reduce storage requirements. For instance, certain parameters or other data may be stored and associated with base counts, and utilized to dynamically generate signal models from the associated base counts as required.

The more accurate the signal models, the more likely the genetic evaluation system will be able to correctly analyze the amplicons. The signals generated by a mass spectrometer are primarily determined by the mass distribution, or equivalently the base count, of the amplicons that are measured. However, estimation of the mass distribution is complicated by the fact that the number of negative charges (i.e., electrons) adhering to each DNA strand varies in a known statistical manner. These mass distributions are further complicated by the fact that the nucleotides employed in the PCR reactions are normally not monoisotopic. Rather, they contain the known natural abundances of the several isotopes of hydrogen, carbon, nitrogen, oxygen, and phosphorus. The combinations of these two distributions cause the mass spectra from a specific amplicon to appear as a sequence of spectral lines occurring at predictable discrete values of the mass-to-charge ratio. The specific form of these probability distributions, which are expected to be approximately binomial, determines the relative molecular amounts that appear at each peak. It is preferable that the predicted shapes of these envelopes also match the observations.

Some or all of the signal models retrieved from the signal model storage A04 and/or the processed mass spectra from the mass spectrometer may be calibrated (A03) to further increase the accuracy of the genetic evaluation system A00. In one illustrative embodiment, the relationship between the predicted mass-to-charge ratios and the observed frequencies of the spectral peaks in the data are determined by one or more calibration coefficients, such as two coefficients. Values for these coefficients, which may be independent of the total amplicon mass, may be estimated from the mass spectra data collected for a known low-mass calibrant molecule that is added to each sample analyzed by the mass spectrometer A01. Any calibrant molecule may be used, such a 12-mer oligonucleotide ($A_1G_6C_3T_2$) that has monoisotopic spectral lines in the vicinity of m/z ratios 739.122, 924.154, and 1,232.542, which may correspond to frequencies of 146,277.930, 116,988.280, and 87,714.374 Hz for a nominal seven Tesla (for example) static magnetic field that may be used in an FTICR mass spectrometer. The mass spectra for the calibrant molecule may include a plurality of calibrant lines that appear as a set of large amplitude lines. The calibrant lines may be sparsely spaced in frequency. By adjusting the calibration coefficients, the errors between the predicted and observed frequency locations of the calibrant spectral peaks may be reduced or even minimized.

The adjusted calibration coefficients may then be applied to one, some, or all of the signal models such that the frequency peaks of any measured amplicon are aligned, or at least as closely aligned as possible (such as within a threshold) with their corresponding prediction in the signal database. FIG. 14-C shows an example of the processed mass spectra data of FIG. 14-A overlaid with a calibrated version of the signal model of FIG. 14-B. As can be seen, the positions of the spectral lines of the processed mass spectra data closely align with those of the calibrated signal model.

Once the measured mass spectra and/or signal models are calibrated, they may be converted to the frequency domain (A03).

The number of molecules appearing in the measured data may be estimated (A06) for each member of a set of hypothesized bioagents. Such estimates may be made in parallel among a plurality of signal models and/or a plurality of PCR primer pairs. When maximum-likelihood processing is performed to simultaneously consider a plurality of signal models over a single primer pair, the calculations involved are referred to herein as a "joint hypothesis." Where maximum-likelihood processing is performed simultaneously taking into account not only a plurality of signal models but also a plurality of primer pairs, such calculations are referred to herein as a "mega hypothesis." Such mega hypotheses, which are associated with candidate bioagent strains, may be considered two-dimensional signal distributions, because they cover multiple primer pairs.

Maximum Likelihood Processing: Combine-and-Detect

Analysis of Mass Spectra to Identify Any Bacterial or Viral Organism: Approach using High Resolution FTICR Mass Spectrometer Once optimum sets of PCR primer pairs have been selected by the procedures described above, the remaining critical task is to identify any bacterial or viral organism present in a sample by analysis of the mass spectra of the amplicons produced by the use of each primer pair to amplify a portion of the sample. The overall block diagram of the maximum-likelihood processor that optimally accomplishes this task is shown in FIG. 1. The functions performed within each block are described in the following (denoted by bold text) for the case of a FTICR mass spectrometer.

As shown in FIG. 1, the input to the maximum-likelihood processor (cf. block labeled as FTICR/TOF Mass Spec Data) is a digitized time series of the signal recorded in response to the chirp excitation applied to the ions in the cell. The first step in the processing (FTICR Data Prep) is to take the Fourier transform of the data with appropriate weighting for sidelobe control to form the coherent frequency response of the excited ions. If the effects due to both ion-neutral collisions and non-linear interactions between charged ions are negligible, then the phase of this complex-valued response is determined by the phase of the excitation chirp waveform. This phase, which is described by a second-order polynomial, is estimated using the strongest observed spectral lines and removed from the data. Once the excitation phase is removed, the data should be essentially real-valued and positive-definite (except for frequency sidelobes).

The maximum-likelihood processor operates by comparing hypothesized mass spectra for the strands of DNA expected for each species amplified by each pair of PCR primers. In order for this procedure to be successful, it is important to have a database (Signal Data Base) of pre-computed signal predictions that accurately match the measurements. The signals for a mass spectrometer are primarily determined by their mass or equivalently their base count. The later quantity is determined by the total number of each of the four nucleotides in the amplicon; i.e., the number of adenine, guanine, cytosine and thymine bases. The expected mass distributions, however, are complicated by the fact that the number of negative charges (electrons) adhering to each DNA strand varies in a known statistical manner. In addition, these distributions are complicated by the fact that the nucleotides employed in the PCR reactions are normally not monoisotopic. Rather, they contain the known natural abundances of the several isotopes of hydrogen, carbon, nitrogen, oxygen, and phosphorus. The combinations of these two distributions cause the signal from a specific amplicon to appear as a sequence of spectral lines occurring at predictable discrete values of the mass-to-charge ratio. The specific form of these probability distributions, which are expected to be approximately binomial, determines the relative molecular amounts that appear at each peak. It is important that the predicted shape of these envelopes also match the observations.

The next step (Signal Calibration) required to prepare the signal predictions for the maximum likelihood processor is frequency calibration. The relationship between the predicted mass-to-charge ratios and the observed frequencies of the spectral peaks in the data are determined by two calibration coefficients. Values for these coefficients, which are independent of the total amplicon mass, are estimated from the data collected for a known low-mass calibrant molecule that is added to each sample sprayed into the mass spectrometer. The calibrant lines appear as a set of large amplitude lines that are sparsely spaced in frequency. By adjusting the calibration coefficients, the errors between the predicted and observed frequency locations of the calibrant spectral peaks are minimized. The resulting coefficients are then applied to the entire database of pre-calculated signatures so that the frequency peaks of any measured amplicon are aligned with their corresponding prediction in the signal database.

The maximum-likelihood processor estimates the molecular amount appearing in the measured data for each member of set of hypothesized organisms. These 'mega-hypotheses', which are associated with candidate organism strains, are two-dimensional signal distributions since they cover multiple primer sets. The processor forms these hypotheses (Predict Signal Hypotheses) by extracting from the signal database the corresponding frequency distribution for the associated amplicon base count at each primer pair.

The base count information needed for each organism is obtained from a genomics database. That database (Genomics Data Base) is formed from either observations or predictions of PCR results on all known bacterial strains or viruses for each primer pair. In general, this information includes the base counts for each operon and the number of copies that appear within the genome. It may also be known that a particular strain fails to prime for a particular primer pair. In that case, there would be no signal expected for that primer pair. In addition, to detect new strain variations or virus mutations small shifts from the expected base counts are also added to the list of hypothesized organisms. The allowed shifts are determined from data tables that quantify the probability of them occurring for each primer pair.

In order to form the organism hypotheses over multiple primer pairs, it is also necessary to account for variations in PCR gains that may occur. That is, the number of DNA dimers obtained from a common organism sample may differ between primer pairs. This information may be obtained from a database of PCR gains (PCR Data Base). Real-time, adaptive gain calibration, can also be enhanced by inclusion of PCR calibrants in every PCR reaction, which not only provide gains, but provide a quality control function to identify failed reactions. Furthermore, in general, the amplicons from the forward and reverse strands do not always occur in equal amounts and additional single-strand PCR by-products can occur. The later includes both non-blunt end products (e.g., additional adenines attached to some fraction of the strands) and partially digested amplicons (missing bases at the 3' end to some fraction of the strands). This information, which depends on the primer pair and the polymerase selected for PCR, is also needed to accurately predict the signatures observed in the mass spectrometer. This should also appear in this database.

The final piece of information needed to implement the maximum likelihood processor is an estimate of the background noise (Noise Estimate). This includes the effects of both electronic noise (expected to be a zero-mean Gaussian process) and chemical ion noise (associated with Poisson fluctuations). In general, both noise components vary with frequency. The chemical noise, which is characterized by a non-zero mean and variance, appears as a sequence of low-amplitude frequency peaks. This noise may be estimated from data sets that do not contain genomic material.

The molecular amounts for the hypothesized organisms are obtained by determining the scale factors that produce the 'best' statistical fit of the mega-hypotheses to the data (Max Likelihood Estimates). An iterative algorithm, which maximizes the likelihood that the measurements are consistent with the signal statistics, is used to calculate these amounts. This algorithm, which bears a strong resemblance to a least-squares algorithm, minimizes the whitened residual between the measured data and the estimated signals. The whitener normalizes the calculated residual power at each frequency bin by the expected noise variance. This includes effects of electronic noise, chemical noise and also signal noise (associated with Poisson sampling fluctuations). The molecular amounts are estimated jointly in order to account for any correlations that occur between different organism hypotheses. In addition, the estimated amounts are also constrained to be non-negative as is required for them to be physically sensible.

The next block of the processor (Detect Pathogens) determines if any member of a list (may depend on type of collection) of biological pathogens is present. A Generalized Likelihood Ratio Test (GLRT) is used to make that decision. This test replaces, in the likelihood ratio, the unknown organism amounts by their maximum likelihood estimates. This includes estimates for both the pathogen and all additional background organisms. The GLRT decides that a pathogen is present if the likelihood ratio (defined for the individual pathogen relative to the background) exceeds a selected threshold. A separate test is performed for each pathogen in the list. The actual value of the threshold depends on both the desired false alarm rate and the background characteristics. Finally, the detected hypotheses may not uniquely identify an organism. For example, it may be possible to associate a detected hypothesis with strain variations from multiple species. In such a case, posterior probabilities, which are determined from the biological probability tables in the genomics database, are calculated for each of the ambiguous organisms. These indicate the probability that each candidate species is consistent with the achieved detection.

The detection capabilities of this processor can be improved by exploiting a priori information (A Priori Information) about the expected clutter and pathogens. That is, the expected background organisms and pathogens depend on the nature of the collected samples. As an example, for clinical applications these can depend on the type of sample (i.e., blood, urine, etc.), patient group, time of year and geographical location. Information about background organisms can also obtained by monitoring the results acquired from common locations and times. This data, which is quantified as a table of priori probabilities for each organism, can be used in the processor in variety of ways. In particular, a priori probabilities can be included in the calculation of the posterior probabilities to improve the association of detections with species. Furthermore, a priori information can be used to minimize the number of hypotheses since there is no need to test signals that have zero probability of appearing in the analyzed sample.

The final processing block (Test Unknowns) determines if any unrecognized species are present in the collected sample. This is achieved by examining the residuals, which are obtained by subtracting the identified signals from the measurements, to determine if they are above the system noise floor. In such a case, the residual data can be examined to determine if its characteristics are consistent with signals associated with non-hypothesized base counts. The primary tool for this analysis is a mass deconvolution algorithm, which identifies additional, unhypothesized masses in the spectrum and then associates their mass to a set of possible base counts based on mass resolution of the spectrometer. These residual, additional basecounts at the single primer step, can then be analyzed with output of the other primers and mapped to a phylogenetic tree for possible identification. If it is decided that additional unknown organisms may be present then additional tests can be requested. Once the characteristics of a new signal are verified, then it would be added to the signal database for all subsequent tests.

It may further be determined whether any unrecognized species are present in the collected sample. This may be achieved by examining the residual, which may be obtained by subtracting the identified signals from the measurements, to determine if the residual is above the system noise floor. Where the residual is above the noise floor, the residual may be examined to determine if its characteristics are consistent with signals associated with non-hypothesized base counts. If it is decided that additional unknown bioagents may be present in the residual then additional tests may be requested. Once the characteristics of a new signal are verified, then it may be added to the signal database A04 for subsequent tests.

While illustrative systems and methods as described herein embodying various aspects of the present invention are shown by way of example, it will be understood, of course, that the invention is not limited to these embodiments. Modifications may be made by those skilled in the art, particularly in light of the foregoing teachings. For example, each of the elements of the aforementioned embodiments may be utilized alone or in combination with elements of the other embodiments. Although the invention has been defined using the appended claims, these claims are exemplary in that the invention is intended to include the elements and steps described herein in any combination or sub combination. Accordingly, there are any number of alternative combinations for defining the invention, which incorporate one or more elements from the specification, including the description, claims, and drawings, in various combinations or sub combinations. It will be apparent to those skilled in the relevant technologies, in light of the present specification, that alternate combinations of aspects of the invention, either alone or in combination with one or more elements or steps defined herein; may be utilized as modifications or alterations of the invention or as part of the invention. It is intended that the written description of the invention contained herein covers all such modifications and alterations.

All patents, patent applications, and references cited in this disclosure are incorporated by reference herein in their entirety.

Example 1

Modifications to Account for Biologically Likely Species Variants ("Cloud Algorithm")

Base count blurring can be carried out as follows. "Electronic PCR" can be conducted on nucleotide sequences of the desired bioagents to obtain the different expected base counts that could be obtained for each primer pair. In one illustrative embodiment, one or more spreadsheets, such as Microsoft Excel workbooks contains a plurality of worksheets. First in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet, "Sheet1" that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains. One of ordinary skill in the art may understand additional pathways for obtaining similar table differences without undo experimentation.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by taking the most abundant strain's base type composition and adding it to the reference set and then the next most abundant strain's base type composition is added until the threshold is met or exceeded. The current set of data was obtained using a threshold of 55%, which was obtained empirically.

For each base count not included in the reference base count set for that bioagent, the script then proceeds to determine the manner in which the current base count differs from each of the base counts in the reference set. This difference may be represented as a combination of substitutions, $S_i = X_i$, and insertions, $I_i = Y_i$, or deletions, $D_i = Z_i$. If there is more than one reference base count, then the reported difference is chosen using rules that aim to minimize the number of changes and, in instances with the same number of changes, minimize the number of insertions or deletions. Therefore, the primary rule is to identify the difference with the minimum sum $(X_i + Y_i)$ or $(X_i + Z_i)$, e.g., one insertion rather than two substitutions. If there are two or more differences with the minimum sum, then the one that will be reported is the one that contains the most substitutions.

Differences between a base count and a reference composition are categorized as either one, two, or more substitutions, one, two, or more insertions, one, two, or more deletions, and combinations of substitutions and insertions or deletions. Tables 1-8 illustrate these changes. The number of possible changes within each category is termed the complexity and is shown in Table 9.

The workbook contains a worksheet for each primer pair; the tables in each worksheet summarize the frequency of the types of base count changes. One worksheet can show the mean and standard deviation for each base count change type over the ten primer pairs.

The results of the above described procedure are presented in tables 1 through 10.

TABLE 1

Single Substitutions

| | |
|---|---|
| A → C | transversion |
| A → G | transition |
| A → T | transversion |
| C → A | transversion |
| C → G | transversion |
| C → T | transition |
| G → A | transition |
| G → C | transversion |
| G → T | transversion |
| T → A | transversion |
| T → C | transition |
| T → G | transversion |

TABLE 2

Two Substitutions

| | |
|---|---|
| AA →CC | 2 transversions |
| AA →CG | transition and transversion |
| AA →CT | 2 transversions |
| AG →CC | 2 transversions |
| AG →CT | 2 transversions |
| AT →CC | transition and transversion |
| AA →GG | 2 transitions |
| AA →GT | transition and transversion |
| AC →GG | transition and transversion |
| AC →GT | 2 transitions |
| AT →GC | 2 transitions |
| AT →GG | transition and transversion |
| AA →TT | 2 transversions |
| AC →TT | transition and transversion |
| AG →TT | 2 transversions |
| CC →AA | 2 transversions |
| CC →AG | 2 transversions |
| CC →AT | transition and transversion |
| CG →AA | transition and transversion |
| CG →AT | 2 transitions |
| CT →AA | 2 transversions |
| CT →AG | 2 transversions |
| CC →GG | 2 transversions |
| CC →GT | transition and transversion |
| CT →GG | 2 transversions |
| CC →TT | 2 transitions |
| CG →TT | transition and transversion |
| GG →AA | 2 transitions |
| GG →AC | transition and transversion |
| GG →AT | transition and transversion |
| GT →AA | transition and transversion |
| GT →AC | 2 transitions |
| GG →CC | 2 transversions |
| GG →CT | 2 transversions |
| GT →CC | transition and transversion |
| GG →TT | 2 transversions |
| TT →AA | 2 transversions |
| TT →AC | transition and transversion |
| TT →AG | 2 transversions |
| TT →CC | 2 transitions |
| TT →CG | transition and transversion |
| TT →GG | 2 transversions |

TABLE 3

Single Insertion

| |
|---|
| →A |
| →C |
| →G |
| →T |

TABLE 4

Two Insertions

→ AA
→ AC
→ AG
→ AT
→ CC
→ CG
→ CT
→ GG
→ GT
→ TT

TABLE 5

Single Deletion

A →
C →
G →

TABLE 6

Two Deletions

AA →
AC →
AG →
AT →
CC →
CG →
CT →
GG →
GT →

TABLE 7

One Substitution and One Insertion

A → CC
A → CG
A → CT
A → GG
A → GT
A → TT
C → AA
C → AG
C → AT
C → GG
C → GT
C → TT
G → AA
G → AC
G → AT
G → CC
G → CT
G → TT
T → AA
T → AC
T → AG
T → CC
T → CG
T → GG

TABLE 8

One Substitution and One Deletion

AA → C
AA → G
AA → T

TABLE 8-continued

One Substitution and One Deletion

AC → G
AC → T
AG → C
AG → T
AT → C
AT → G
CC → A
CC → G
CC → T
CG → A
CG → T
CT → A
CT → G
GG → A
GG → C
GG → T
GT → A
GT → C
TT → A
TT → C
TT → G

TABLE 9

Complexity of base count changes

| Type of base composition change | Comp |
|---|---|
| Single Substitution | Purine → Purine |
| | Purine → Pyrimidine |
| | Pyrimidine → Purine |
| | Pyrimidine → Pyrimidine |
| | Single Transition |
| | Single Transversion |
| Two Substitutions | Two Transitions |
| | One Transition & One Transversion |
| | Two Transversions |
| Three Substitutions | Single Purine |
| One Insertion | Single Pyrimidine |
| Two Insertions | Two Purines |
| | One Purine & One Pyrimidine |
| | Two Pyrimidines |
| Three Insertions | Single Purine |
| One Deletion | Single Pyrimidine |
| Two Deletions | Two Purines |
| | One Purine & One Pyrimidine |
| | Two Pyrimidines |
| Three Deletions | Purine → TwoPurines |
| One Insertion & One Substitution | Purine → One Purine & One Pyrimidine |
| | Purine → TwoPyrimidines |
| | Pyrimidine → TwoPurines |
| | Pyrimidine → One Purine & One Pyrimidine |
| | Pyrimidine → TwoPyrimidines |
| | Single Transition & One Purine Insertion |
| | Single Transition & One Pyrimidine Insertion |
| | Single Transversion & One Purine Insertion |
| | Single Transversion & One Pyrimidine Insertion |
| One Deletion & One Substitution | Two Purines → Purine |
| | One Purine & One Pyrimidine → Purine |
| | Two Pyrimidines → Purine |
| | Two Purines → Pyrimidine |
| | One Purine & One Pyrimidine → Pyrimidine |
| | Two Pyrimidines → Pyrimidine |
| | Single Transition & One Purine Deletion |
| | Single Transition & One Pyrimidine Deletion |
| | Single Transversion & One Purine Deletion |
| | Single Transversion & One Pyrimidine Deletion |

TABLE 10

Average Frequencies of Various Base Composition Changes
Deduced from Electronic PCR of 16S Ribosomal Data

| Strain Threshold = 55% | Strains Average | Strains Std. Dev. | Strains/Complexity Average | Strains/Complexity Std. Dev. | Base Compositions Average | Base Compositions Std. Dev. | Base Compositions/Complexity Average | Base Compositions/Complexity Std. Dev. |
|---|---|---|---|---|---|---|---|---|
| No Changes | 85.9% | 5.7% | 85.9% | 5.7% | 41.8% | 7.6% | 41.8% | 7.6% |
| All Changes | 14.1% | 5.7% | | | 58.2% | 7.6% | | |
| Single Substitution | 7.5% | 3.1% | 0.63% | 0.3% | 29.5% | 2.5% | 2.5% | 0.21% |
| Purine -> Purine | 2.6% | 1.6% | 1.29% | 0.8% | 8.5% | 2.5% | 4.3% | 1.23% |
| Purine -> Pyrimidine | 1.0% | 0.5% | 0.24% | 0.1% | 5.4% | 2.3% | 1.4% | 0.58% |
| Pyrimidine -> Purine | 1.1% | 0.4% | 0.28% | 0.1% | 5.8% | 2.0% | 1.5% | 0.50% |
| Pyrimidine -> Pyrimidine | 2.9% | 1.2% | 1.44% | 0.6% | 9.7% | 2.1% | 4.9% | 1.03% |
| Single Transition | 5.5% | 2.5% | 1.36% | 0.6% | 18.2% | 2.5% | 4.6% | 0.63% |
| Single Transversion | 2.1% | 0.7% | 0.26% | 0.1% | 11.2% | 2.2% | 1.4% | 0.27% |
| Two Substitutions | 2.5% | 1.2% | 0.06% | 0.0% | 9.7% | 2.9% | 0.2% | 0.07% |
| Two Transitions | 1.2% | 0.9% | 0.17% | 0.1% | 3.7% | 1.1% | 0.5% | 0.16% |
| One Transition & One Transversion | 0.6% | 0.4% | 0.04% | 0.0% | 2.8% | 1.7% | 0.2% | 0.11% |
| Two Transversions | 0.7% | 0.6% | 0.04% | 0.0% | 3.2% | 1.7% | 0.2% | 0.09% |
| Three or More Substitutions | 1.0% | 1.0% | 0.01% | 0.0% | 4.5% | 3.2% | 0.0% | 0.03% |
| One Insertion | 1.0% | 1.0% | 0.26% | 0.2% | 3.8% | 2.5% | 0.9% | 0.62% |
| Single Purine | 0.6% | 0.5% | 0.28% | 0.2% | 2.1% | 1.1% | 1.1% | 0.57% |
| Single Pyrimidine | 0.5% | 0.8% | 0.24% | 0.4% | 1.6% | 1.5% | 0.8% | 0.77% |
| Two Insertions | 0.1% | 0.2% | 0.01% | 0.0% | 0.5% | 0.6% | 0.1% | 0.06% |
| Two Purines | 0.0% | 0.0% | 0.01% | 0.0% | 0.2% | 0.3% | 0.1% | 0.08% |
| One Purine & One Pyrimidine | 0.1% | 0.1% | 0.02% | 0.0% | 0.2% | 0.3% | 0.1% | 0.08% |
| Two Pyrimidines | 0.0% | 0.0% | 0.01% | 0.0% | 0.1% | 0.2% | 0.0% | 0.06% |
| Three or More Insertions | 0.1% | 0.1% | 0.00% | 0.0% | 0.5% | 0.5% | 0.0% | 0.03% |
| One Deletion | 0.6% | 0.4% | 0.15% | 0.1% | 3.2% | 1.8% | 0.8% | 0.44% |
| Single Purine | 0.3% | 0.2% | 0.17% | 0.1% | 1.7% | 0.9% | 0.9% | 0.43% |
| Single Pyrimidine | 0.3% | 0.3% | 0.13% | 0.1% | 1.5% | 1.3% | 0.7% | 0.66% |
| Two Deletions | 0.1% | 0.2% | 0.01% | 0.0% | 0.9% | 1.0% | 0.1% | 0.10% |
| Two Purines | 0.0% | 0.1% | 0.02% | 0.0% | 0.4% | 0.5% | 0.1% | 0.15% |
| One Purine & One Pyrimidine | 0.1% | 0.1% | 0.02% | 0.0% | 0.3% | 0.6% | 0.1% | 0.14% |
| Two Pyrimidines | 0.0% | 0.0% | 0.01% | 0.0% | 0.2% | 0.3% | 0.1% | 0.08% |
| Three or More Deletions | 0.1% | 0.1% | 0.00% | 0.0% | 0.4% | 0.4% | 0.0% | 0.02% |
| One Insertion & One Substitution | 0.1% | 0.1% | 0.00% | 0.0% | 0.7% | 0.5% | 0.0% | 0.02% |
| Purine -> Two Purines | 0.0% | 0.0% | 0.00% | 0.0% | 0.0% | 0.0% | 0.0% | 0.00% |
| Purine -> One Purine & One Pyrimidine | 0.0% | 0.0% | 0.00% | 0.0% | 0.1% | 0.2% | 0.0% | 0.05% |
| Purine -> Two Pyrimidines | 0.0% | 0.0% | 0.00% | 0.0% | 0.2% | 0.2% | 0.0% | 0.03% |
| Pyrimidine -> Two Purines | 0.0% | 0.0% | 0.00% | 0.0% | 0.2% | 0.3% | 0.0% | 0.04% |
| Pyrimidine -> One Purine & One Pyrimidine | 0.0% | 0.0% | 0.01% | 0.0% | 0.2% | 0.3% | 0.0% | 0.07% |
| Pyrimidine -> Two Pyrimidines | 0.0% | 0.0% | 0.00% | 0.0% | 0.0% | 0.0% | 0.0% | 0.00% |
| One Deletion & One Substitution | 0.2% | 0.2% | 0.01% | 0.0% | 1.1% | 0.9% | 0.0% | 0.04% |
| Two Purines -> Purine | 0.0% | 0.0% | 0.00% | 0.0% | 0.0% | 0.0% | 0.0% | 0.00% |
| One Purine & One Pyrimidine -> Purine | 0.0% | 0.0% | 0.01% | 0.0% | 0.4% | 0.4% | 0.1% | 0.11% |
| Two Pyrimidines -> Purine | 0.0% | 0.1% | 0.01% | 0.0% | 0.1% | 0.2% | 0.0% | 0.04% |
| Two Purines -> Pyrimidine | 0.0% | 0.0% | 0.00% | 0.0% | 0.2% | 0.3% | 0.0% | 0.05% |
| One Purine & One Pyrimidine -> Pyrimidine | 0.0% | 0.1% | 0.01% | 0.0% | 0.2% | 0.3% | 0.1% | 0.08% |
| Two Pyrimidines -> Pyrimidine | 0.0% | 0.0% | 0.01% | 0.0% | 0.1% | 0.3% | 0.1% | 0.13% |
| >=1 Insertions/Deletions & >=1 Substitutions | 0.8% | 1.3% | | | 3.5% | 3.7% | | |

We claim:

1. A system, comprising:
   a) a mass spectrometer for obtaining a mass spectrum signal of a nucleic acid amplification product of an unknown bioagent, wherein said mass spectrum signal corresponds to a molecular mass of said nucleic acid amplification product, and wherein said nucleic acid amplification product is delineated by a primer set;
   b) a signal processor for:
      i) converting said mass spectrum signal to a base composition wherein said base composition identifies the number of, but not the nucleic acid gene sequence order of, A residues, C residues, T residues, and G residues in said amplification product,
      ii) comparing said base composition of said nucleic acid amplification product of said unknown bioagent with a plurality of base compositions of virtual nucleic acid amplicons of known bioagents, wherein said virtual nucleic acid amplicons are delineated by said primer set, and wherein said base compositions of said virtual nucleic acid amplicons of known bioagents identify the number of, but not the nucleic acid gene sequence order of, A residues, C residues, T residues, and G residues in said virtual nucleic acid amplicons of known bioagents, and
      iii) detecting a match of said base composition of said nucleic acid amplification product of said unknown bioagent with a base composition from said plurality of base compositions of virtual nucleic acid amplicons of known bioagents;
   wherein said signal processor generates a report identifying said unknown bioagent based on said match.

2. The system of claim 1 wherein said signal processor estimates said one or more parameters and detects said match using a maximum likelihood detection algorithm.

3. The system of claim 2 wherein said maximum likelihood detection algorithm is configured to simultaneously consider a plurality of base compositions generated from virtual nucleic acid amplicons with a single primer pair.

4. The system of claim 2 wherein said maximum likelihood detection algorithm is configured to simultaneously consider a plurality of base compositions generated from virtual nucleic acid amplicons with a plurality of primer pairs.

5. The system of claim 4 wherein said plurality of primer pairs is five or more primer pairs.

6. The system of claim 1 further comprising a means for transferring one or more amplification products to said mass spectrometer.

7. The system of claim 1 further comprising a genomics database and a signal hypothesis predictor configured for transferring genomics data from said genomics database to said signal hypothesis predictor for prediction of said base compositions and transfer of said base compositions to said signal processor.

8. The system of claim 7 further comprising a signal model storage database configured for receiving said base composition from said signal hypothesis predictor, storing said base compositions and transferring said base compositions to said signal processor.

9. The system of claim 1 further comprising a noise estimator configured for processing noise from mass spectrometer data obtained from said mass spectrometer, producing a noise estimate and transferring said noise estimate to said signal processor and incorporated into said means for estimating said one or more parameters for said mass spectrum signal and detecting a match of said base composition with a base composition of said plurality of virtual nucleic acid amplicons.

10. The system of claim 1 wherein said signal processor comprises a generalized likelihood ratio test algorithm used to determine if a member of a list of pathogens is present in a sample comprising said amplification product.

11. The system of claim 1 wherein said signal processor comprises a mass deconvolution algorithm configured to identify unrecognized mass spectrum signals.

12. The system of claim 1 wherein said signal processor comprises a table of probabilities of detection of background organisms configured to identify probable background organisms in a sample comprising said nucleic acid amplification product.

13. The system of claim 1 wherein mass spectrum signal of said nucleic acid amplification product of said unknown bioagent comprises a real mass spectrum signal.

14. The system of claim 1 comprising a database of base counts corresponding to said plurality of virtual mass spectrum signals of virtual nucleic acid amplicons of known bioagents.

15. The system of claim 1 wherein said primer set comprises at least one primer pair that binds to nucleotide sequence regions that flank an intervening variable region.

16. The system of claim 15 wherein said nucleotide sequence regions comprise conserved regions.

* * * * *